US011384383B2

(12) United States Patent
Ouellet et al.

(10) Patent No.: US 11,384,383 B2
(45) Date of Patent: Jul. 12, 2022

(54) IN VITRO ISOLATION AND ENRICHMENT OF NUCLEIC ACIDS USING SITE-SPECIFIC NUCLEASES

(71) Applicant: DEPIXUS, Paris (FR)

(72) Inventors: Jimmy Ouellet, Lardy (FR); Jerôme Maluenda, Saint Michel S/Orge (FR)

(73) Assignee: DEPIXUS, Paris (FR)

( * ) Notice: Subject to any disclaimer, the term of this patent is extended or adjusted under 35 U.S.C. 154(b) by 181 days.

(21) Appl. No.: 16/637,586

(22) PCT Filed: Aug. 8, 2018

(86) PCT No.: PCT/EP2018/071557
§ 371 (c)(1),
(2) Date: Feb. 7, 2020

(87) PCT Pub. No.: WO2019/030306
PCT Pub. Date: Feb. 14, 2019

(65) Prior Publication Data

US 2020/0181683 A1 Jun. 11, 2020

(30) Foreign Application Priority Data

Aug. 8, 2017 (EP) .................................... 17306055

(51) Int. Cl.
*C12Q 1/6806* (2018.01)
*C12N 9/22* (2006.01)

(52) U.S. Cl.
CPC ............. *C12Q 1/6806* (2013.01); *C12N 9/22* (2013.01); *C12Q 2521/301* (2013.01)

(58) Field of Classification Search
CPC ... C12Q 1/6806; C12Q 2521/301; C12N 9/22
See application file for complete search history.

(56) References Cited

U.S. PATENT DOCUMENTS 10,081,829 B1 * 9/2018 Shuber .................. C12Q 1/701
2014/0356867 A1 * 12/2014 Peter .................... C12Y 301/00 435/6.11
2016/0017396 A1 * 1/2016 Cann ...................... C12Q 1/683 506/2
2016/0208241 A1 * 7/2016 Tsai ..................... C12Q 1/6869
2018/0356410 A1 12/2018 Shuber et al.

FOREIGN PATENT DOCUMENTS

WO 2011/147929 A1 12/2011
WO 2011/147931 A1 12/2011
WO 2013/093005 A1 6/2013
WO 2013/176772 A1 11/2013
WO 2014/093595 A1 6/2014
WO 2014/114687 A1 7/2014
WO 2015/071474 A9 5/2015
WO 2016/014409 A1 1/2016
WO 2016/100955 A2 6/2016
WO 2016/177808 A1 11/2016
WO 2018/231942 A1 12/2018
WO 2018/231945 A1 12/2018
WO 2018/231946 A1 12/2018
WO 2018/231952 A1 12/2018
WO 2018/231955 A1 12/2018
WO 2018/231957 A1 12/2018
WO 2018/231963 A1 12/2018
WO 2018/231965 A1 12/2018
WO 2018/231967 A2 12/2018
WO 2018/231985 A1 12/2018
WO 2019/005806 A1 1/2019

OTHER PUBLICATIONS

Gahan, Int J Womens Health. "Circulating nucleic acids in plasma and serum: applications in diagnostic techniques for noninvasive prenatal diagnosis" 2013, 5: 177-186.
Ghorbian and Ardekani, "Non-Invasive Detection of Esophageal Cancer using Genetic Changes in Circulating Cell-Free DNA" Avicenna J Med Biotech. 2012, 4(1): 3-13.
Karvelis et al., "Rapid characterization of CRISPR-Cas9 protospacer adjacent motif sequence elements" Genome Biology, 2015, 16:253.
Mertes et al., "Targeted enrichment of genomic DNA regions for next-generation sequencing" Brief Funct Genomics, 2011, 10(6): 374-86.
Pingoud and Jeltsch, "Structure and function of type II restriction endonucleases," Nucleic Acids Res, 2001, 29(18): 3705-3727.
Slaymaker et al., "Rationally engineered Cas9 nucleases with improved specificity" Science, 2015, 351(6268): 84-86.
Strohkendl et al., "Kinetic Basis for DNA Target Specificity of CRISPRCas12a" Molecular Cell, 2018, 71:816-824.
Wojno et al., "Reduced Rate of Repeated Prostate Biopsies Observed in ConfirmMDx Clinical Utility Field Study" American health & drug benefits, 2014, 7(3): 129.
Zhang et al., "Optimizing the specificity of nucleic acid hybridization" Nat Chem, 2012, 4(3):208-214.
Jinek et al. "A Programmable Dual-RNA-Guided DNA Endonuclease in Adaptive Bacterial Immunity" 2012, Science, 337(6096): 816-821.

(Continued)

*Primary Examiner* — Cynthia B Wilder
(74) *Attorney, Agent, or Firm* — Arrigo, Lee, Guttman & Mouta-Bellum LLP

(57) ABSTRACT

The present invention relates to a method for the isolation of a target nucleic acid region. In particular, said method comprises the steps of contacting a population of nucleic acid molecules with at least one Type II Cas protein-gRNA complex, wherein said gRNA comprises a guide segment that is complementary to the sequence comprised in the target region of at least one nucleic acid molecule, thereby forming a Type II Cas protein-gRNA-nucleic acid complex, contacting the population of nucleic acid molecules with at least one enzyme having exonuclease activity, and isolating the target nucleic acid region from the Type II Cas protein-gRNA-nucleic acid complex.

20 Claims, 24 Drawing Sheets

Figure 1B:
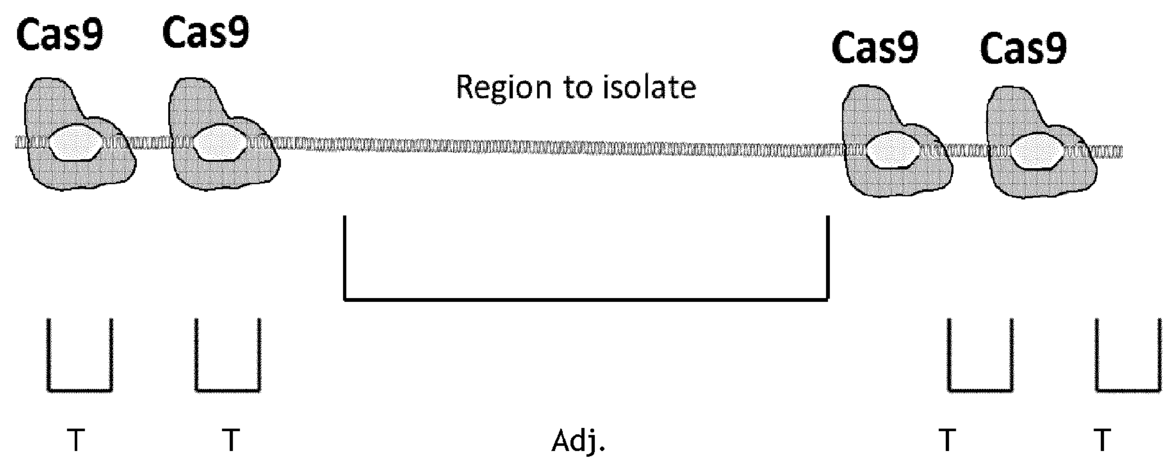

Specification includes a Sequence Listing.

(56) References Cited

OTHER PUBLICATIONS

Zetsche et al., "Cpf1 is a single RNA-guided endonuclease of a Class 2 CRISPR-Cas system" Cell, 2015, 163(3): 759-771.
Hsieh et al., "Electrochemical DNA Detection via Exonuclease and Target-Catalyzed Transformation of Surface-Bound Probes" 2010, Langmuir, 26(12):10392-10396.
Pattanayak et al., "High-throughput profiling of off-target DNA cleavage reveals RNA-programmed Cas9 nuclease specificity" 2013, Nat Biotechnol., 31(9):839-43.
Hsu et al., "DNA targeting specificity of RNA-guided Cas9 nucleases" 2013, Nature Biotechnol., 31:827-832.
Wang et al., "Genetic screens in human cells using the CRISPR/Cas9 system" 2014, Science, 343(6166):80-4.
Kozarewa et al., "Overview of Target Enrichment Strategies" 2015, Curr Protoc Mol Biol,112:7.21.
Sternberg, et al., "DNA interrogation by the CRISPR RNA-guided endonuclease Cas9" 2014, Nature, 507, 62-67.
Mamanova et al., "Target-enrichment strategies for nextgeneration sequencing" 2010, Nature Methods, 7(2), 111-118.

* cited by examiner

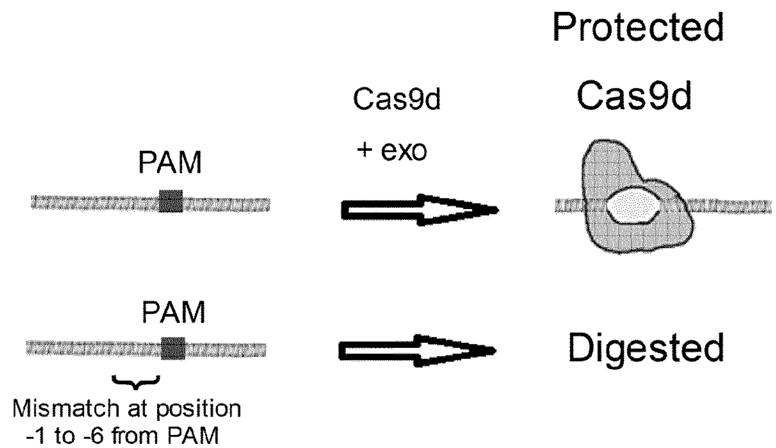

Guide RNA sequence PAM

```
Wild type  5' attgtgcctcgcgctcagtcagactgcgctactttgaac CGG aaatgtcgtgtggg 3'
MM-1       5' attgtgcctcgcgctcagtcagactgcgctactttgaaa CGG aaatgtcgtgtggg 3'
MM-2       5' attgtgcctcgcgctcagtcagactgcgctactttgacc CGG aaatgtcgtgtggg 3'
MM-3       5' attgtgcctcgcgctcagtcagactgcgctactttgcac CGG aaatgtcgtgtggg 3'
MM-4       5' attgtgcctcgcgctcagtcagactgcgctactttcaac CGG aaatgtcgtgtggg 3'
MM-5       5' attgtgcctcgcgctcagtcagactgcgctacttcgaac CGG aaatgtcgtgtggg 3'
MM-6       5' attgtgcctcgcgctcagtcagactgcgctactctgaac CGG aaatgtcgtgtggg 3'
```

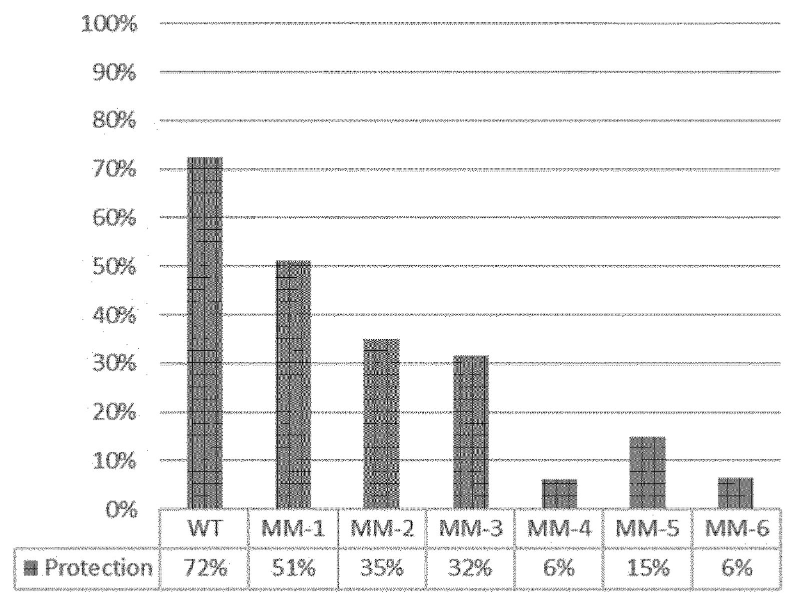

Fig. 1A

| Condition | Concentration | Efficiency |
|---|---|---|
| untreated | 2.63 nmol/L | - |
| 1:1:1 | 0.21 nmol/L | 8% |
| 1:2:5 | 0.35 nmol/L | 13% |
| 1:5:10 | 0.85 nmol/L | 32% |
| 1:10:10 | 1.72 nmol/L | 65% |
| 1:10:20 | 1.84 nmol/L | 70% |
| 1:10:50 | 2.32 nmol/L | 88% |

| Site | Expected | Experimental | Difference |
|---|---|---|---|
| CAAG | 4468 | 4477 | -9 |
| CAAG | 4345 | 4352 | -7 |
| CAAG | 3999 | 3989 | 10 |
| CAAG | 3944 | 3940 | 4 |
| CAAG | 3788 | 3782 | 6 |
| CAAG | 3782 | | |
| CAAG | 2488 | 2504 | -16 |
| CAAG | 2380 | 2385 | -5 |
| CAAG | 1917 | 1942 | -25 |
| CAAG | 1301 | 1298 | 3 |
| CAAG | 1292 | | |
| CAAG | 1024 | 1015 | 9 |
| CAAG | 722 | 702 | 20 |
| CAAG | 587 | 605 | -18 |
| CAAG | 341 | 333 | 8 |

* Extra peak

| Site | Expected | Experimental | Difference |
|---|---|---|---|
| CAAG | 1173 | 1085 | -12 |
| CAAG | 1062 | 1051 | 11 |
| CAAG | 1043 | 1026 | 17 |
| CAAG | 811 | 811 | 0 |
| CAAG | 558 | 571 | -13 |
| CAAG | 411 | 395 | 16 |
| CAAG | 328 | 329 | -1 |
| CAAG | 266 | 271 | -5 |
| CAAG | 203 | 187 | 16 |

| Site | Expected |
|---|---|
| CAAG | 930* |
| CAAG | 829* |
| CAAG | 778* |
| CAAG | 771* |
| CAAG | 353 |
| CAAG | 262 |

*Positions depend on the number of repeats

| Gene | Target | Disease | Chr | Start | End | Target Size |
|---|---|---|---|---|---|---|
| FMR1 | GCC-repeat | Fragile X syndrome | X | 147911033 | 147912743 | 1710 |
| C9orf72 | CpG+GGGGCC-repeat | amyotrophic lateral sclerosis | 9 | 27572678 | 27574118 | 1440 |
| SEPT9.1 | CpG | colorectal cancer | 17 | 77372516 | 77374810 | 2294 |
| SEPT9.2 | CpG | colorectal cancer | 17 | 77450851 | 77451948 | 1097 |
| CNRIP1 | CpG | colorectal cancer | 2 | 68319021 | 68320292 | 1271 |
| FBN1 | CpG | colorectal cancer | 15 | 48644393 | 48646658 | 2265 |
| INA | CpG | colorectal cancer | 10 | 103276677 | 103278492 | 1815 |
| MAL | CpG | colorectal cancer | 2 | 95024889 | 95026822 | 1933 |
| SNCA | CpG | colorectal cancer | 4 | 89836537 | 89837940 | 1403 |
| SPG20 | CpG | colorectal cancer | 13 | 36345467 | 36347222 | 1755 |
| HTT | CpG+CAG-repeat | huntington | 4 | 3073479 | 3075121 | 1642 |
| EGFR | CpG | lung cancer | 7 | 55018205 | 55020556 | 2351 |
| NDRG4.1 | CpG | myofibromatosis | 16 | 58462874 | 58465447 | 2573 |
| NDRG4.2 | CpG | myofibromatosis | 16 | 58500516 | 58501908 | 1392 |
| DMPK | CTG-repeat | Myotonic dystrophy | 19 | 45770028 | 45772277 | 2249 |

Fig. 13A

| Target | Cpf1-crRNA#1 | Cpf1-crRNA#2 | Cas9-gRNA#1 | Cas9-gRNA#2 | Cas9-gRNA#3 | Cas9-gRNA#4 |
|---|---|---|---|---|---|---|
| C9orf72 | 97% | 93% | 90% | 87% | 95% | 73% |
| SEPT9.1 | 97% | 90% | 80% | 32% | 80% | 90% |
| SEPT9.2 | 100% | 100% | 90% | 80% | 85% | 75% |
| CNRIP1 | 100% | 100% | 80% | 20% | 15% | 56% |
| FBN1 | 100% | 100% | 88% | 90% | 85% | 90% |
| INA | 98% | 95% | 60% | 72% | 90% | 83% |
| MAL | 90% | 100% | 78% | 71% | 75% | 95% |
| SNCA | 97% | 100% | 91% | 75% | 88% | 75% |
| SPG20 | 87% | 94% | 70% | 90% | 72% | 90% |
| HTT | 88% | 100% | 51% | 88% | 77% | 48% |
| EGFR | 97% | 100% | 75% | 73% | 60% | 35% |
| NDRG4.1 | 100% | 100% | 80% | 92% | 87% | 82% |
| NDRG4.2 | 100% | 100% | 40% | 50% | 40% | 50% |
| DMPK | 95% | 100% | 80% | 80% | 90% | 80% |

*grey = cleavage less than 70%

Fig. 13C

SEQUENCE LISTING

<160> NUMBER OF SEQ ID NOS: 240

<210> SEQ ID NO 1
<211> LENGTH: 4071
<212> TYPE: DNA
<213> ORGANISM: Artificial
<220> FEATURE:
<223> OTHER INFORMATION: 4 kb plasmid pPS009 comprising the FrmI region

<400> SEQUENCE: 1

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgaat tgtaatacga ctcactatag ggcgaatgga gacgagctcc    660

accgcggtgg cggccgctct agaactagtg gatccgtaga cgcctcacct tctgcctcta    720

cgggtcacaa aagcctgggt caccctggtt gccactgttc ctagttcaaa gtcttcttct    780

gtctaatcct tcacccctat tctcgccttc cactccacct cccgctcagt cagactgcgc    840

tactttgaac cggaccaaac caaaccaaac caaaccaaac caaaccagac cagacacccc    900

ctcccgcgga atcccagaga ggccgaactg ggataaccgg atgcatttga tttcccacgc    960

cactgagtgc acctctgcag aaatgggcgt tctggccctc gcgaggcagt gcgacctgtc   1020

accgcccttc agccttcccg ccctccacca agcccgcgca cgcccggccc gcgcgtctgt   1080

ctttcgaccc ggcaccccgg ccggttccca gcagcgcgca tgcgcgcgct cccaggccac   1140

ttgaagagag agggcggggc cgaggggctg agcccgcggg gggagggaac agcgttgatc   1200

acgtgacgtg gtttcagtgt ttacacccgc agcgggccgg gggttcggcc tcagtcaggc   1260

gctcagctcc gtttcggttt cacttccggt ggagggccgc ctctgagcgg gcggcgggcc   1320

gacggcgagc gcgggcggcg gcggtgacgg aggcgccgct gccagggggc gtgcggcagc   1380

gcggcggcgg cggcggcggc ggcggcggcg gaggcggcgg cggcggcggc ggcggcggcg   1440

gctgggcctc gagcgcccgc agcccacctc tcgggggcgg gctcccggcg ctagcagggc   1500

tgaagagaag atggaggagc tggtggtgga agtgcggggc tccaatggcg ctttctacaa   1560

ggtacttggc tctagggcag gccccatctt cgcccttcct tccctccctt ttcttcttgg   1620

tgtcggcggg aggcaggccc ggggccctct tcccgagcac cgcgcctggg tgccagggca   1680

cgctcggcgg gatgttgttg ggagggaagg actggacttg gggcctgttg gaagcccctc   1740

tccgactccg agaggcccta gcgcctatcg aaatgagaga ccagcgagga gagggttctc   1800

tttcggcgcc gagaattcga tatcaagctt atcgataccg tcgacctcga ggggggggcc   1860

ggtaccgtct cagcttttgt tccctttagt gagggttaat ttcgagcttg gcgtaatcat   1920

ggtcatagct gtttcctgtg tgaaattgtt atccgctcac aattccacac aacatacgag   1980

ccggaagcat aaagtgtaaa gcctggggtg cctaatgagt gagctaactc acattaattg   2040
```

```
cgttgcgctc actgcccgct ttccagtcgg gaaacctgtc gtgccagctg cattaatgaa   2100

tcggccaacg cgcggggaga ggcggtttgc gtattgggcg ctcttccgct tcctcgctca   2160

ctgactcgct gcgctcggtc gttcggctgc ggcgagcggt atcagctcac tcaaaggcgg   2220

taatacggtt atccacagaa tcaggggata acgcaggaaa gaacatgtga gcaaaaggcc   2280

agcaaaaggc caggaaccgt aaaaaggccg cgttgctggc gtttttccat aggctccgcc   2340

cccctgacga gcatcacaaa aatcgacgct caagtcagag gtggcgaaac ccgacaggac   2400

tataaagata ccaggcgttt ccccctggaa gctccctcgt gcgctctcct gttccgaccc   2460

tgccgcttac cggatacctg tccgcctttc tcccttcggg aagcgtggcg ctttctcata   2520

gctcacgctg taggtatctc agttcggtgt aggtcgttcg ctccaagctg ggctgtgtgc   2580

acgaaccccc cgttcagccc gaccgctgcg ccttatccgg taactatcgt cttgagtcca   2640

acccggtaag acacgactta tcgccactgg cagcagccac tggtaacagg attagcagag   2700

cgaggtatgt aggcggtgct acagagttct tgaagtggtg gcctaactac ggctacacta   2760

gaaggacagt atttggtatc tgcgctctgc tgaagccagt taccttcgga aaaagagttg   2820

gtagctcttg atccggcaaa caaaccaccg ctggtagcgg tggttttttt gtttgcaagc   2880

agcagattac gcgcagaaaa aaaggatctc aagaagatcc tttgatcttt tctacggggt   2940

ctgacgctca gtggaacgaa aactcacgtt aagggatttt ggtcatgaga ttatcaaaaa   3000

ggatcttcac ctagatcctt ttaaattaaa aatgaagttt taaatcaatc taaagtatat   3060

atgagtaaac ttggtctgac agttaccaat gcttaatcag tgaggcacct atctcagcga   3120

tctgtctatt tcgttcatcc atagttgcct gactccccgt cgtgtagata actacgatac   3180

gggagggctt accatctggc cccagtgctg caatgatacc gcgagaccca cgctcaccgg   3240

ctccagattt atcagcaata aaccagccag ccggaagggc cgagcgcaga agtggtcctg   3300

caactttatc cgcctccatc cagtctatta attgttgccg ggaagctaga gtaagtagtt   3360

cgccagttaa tagtttgcgc aacgttgttg ccattgctac aggcatcgtg gtgtcacgct   3420

cgtcgtttgg tatggcttca ttcagctccg gttcccaacg atcaaggcga gttacatgat   3480

cccccatgtt gtgcaaaaaa gcggttagct ccttcggtcc tccgatcgtt gtcagaagta   3540

agttggccgc agtgttatca ctcatggtta tggcagcact gcataattct cttactgtca   3600

tgccatccgt aagatgcttt tctgtgactg gtgagtactc aaccaagtca ttctgagaat   3660

agtgtatgcg gcgaccgagt tgctcttgcc cggcgtcaat acgggataat accgcgccac   3720

atagcagaac tttaaaagtg ctcatcattg gaaaacgttc ttcggggcga aaactctcaa   3780

ggatcttacc gctgttgaga tccagttcga tgtaacccac tcgtgcaccc aactgatctt   3840

cagcatcttt tactttcacc agcgtttctg ggtgagcaaa aacaggaagg caaaatgccg   3900

caaaaaaggg aataagggcg acacggaaat gttgaatact catactcttc ctttttcaat   3960

attattgaag catttatcag ggttattgtc tcatgagcgg atacatattt gaatgtattt   4020

agaaaaataa acaaataggg gttccgcgca catttccccg aaaagtgcca c             4071
```

<210> SEQ ID NO 2
<211> LENGTH: 1118
<212> TYPE: DNA
<213> ORGANISM: Homo sapiens

<400> SEQUENCE: 2

```
gtagacgcct caccttctgc ctctacgggt cacaaaagcc tgggtcaccc tggttgccac     60
```

tgttcctagt tcaaagtctt cttctgtcta atccttcacc cctattctcg ccttccactc 120
cacctcccgc tcagtcagac tgcgctactt tgaaccggac caaaccaaac caaaccaaac 180
caaaccaaac cagaccagac acccccctccc gcggaatccc agagaggccg aactgggata 240
accggatgca tttgatttcc cacgccactg agtgcacctc tgcagaaatg ggcgttctgg 300
ccctcgcgag gcagtgcgac ctgtcaccgc ccttcagcct tcccgccctc caccaagccc 360
gcgcacgccc ggcccgcgcg tctgtctttc gacccggcac cccggccggt tcccagcagc 420
gcgcatgcgc gcgctcccag gccacttgaa gagagagggc ggggccgagg ggctgagccc 480 gcgggggggag ggaacagcgt tgatcacgtg acgtggtttc agtgtttaca cccgcagcgg 540
gccgggggtt cggcctcagt caggcgctca gctccgtttc ggtttcactt ccggtggagg 600
gccgcctctg agcgggcggc gggccgacgg cgagcgcggg cggcggcggt gacggaggcg 660
ccgctgccag gggcgtgcg gcagcgcggc ggcggcggcg gcggcggcgg cggcggaggc 720
ggcggcggcg gcggcggcgg cggcggctgg gcctcgagcg cccgcagccc acctctcggg 780
ggcgggctcc cggcgctagc agggctgaag agaagatgga ggagctggtg gtggaagtgc 840
ggggctccaa tggcgctttc tacaaggtac ttggctctag ggcaggcccc atcttcgccc 900
ttccttccct cccttttctt cttggtgtcg gcgggaggca ggcccggggc cctcttcccg 960
agcaccgcgc ctgggtgcca gggcacgctc ggcgggatgt tgttgggagg gaaggactgg 1020
acttggggcc tgttggaagc ccctctccga ctccgagagg ccctagcgcc tatcgaaatg 1080
agagaccagc gaggagaggg ttctctttcg gcgccgag 1118

<210> SEQ ID NO 3
<211> LENGTH: 20
<212> TYPE: RNA
<213> ORGANISM: Artificial
<220> FEATURE:
<223> OTHER INFORMATION: Target specific sequence of the Cas9 gRNA-FrmI#1

<400> SEQUENCE: 3
cagacugcgc uacuuugaac 20

<210> SEQ ID NO 4
<211> LENGTH: 20
<212> TYPE: RNA
<213> ORGANISM: Artificial
<220> FEATURE:
<223> OTHER INFORMATION: Target specific sequence of the Cas9 gRNA-FrmI#2

<400> SEQUENCE: 4
gcgcuagggc cucucggagu 20

<210> SEQ ID NO 5
<211> LENGTH: 20
<212> TYPE: RNA
<213> ORGANISM: Artificial
<220> FEATURE:
<223> OTHER INFORMATION: Target specific sequence of the Cas9 gRNA-Frm1#3

<400> SEQUENCE: 5
gcgcagucug acugagcggg 20

<210> SEQ ID NO 6
<211> LENGTH: 20
<212> TYPE: RNA

<213> ORGANISM: Artificial
<220> FEATURE:
<223> OTHER INFORMATION: Target specific sequence of the Cas9 gRNA-Ecoli#1

<400> SEQUENCE: 6
caucagugac auccuaucac 20

<210> SEQ ID NO 7
<211> LENGTH: 20
<212> TYPE: RNA
<213> ORGANISM: Artificial
<220> FEATURE:
<223> OTHER INFORMATION: Target specific sequence of the Cas9 gRNA-Ecoli#2

<400> SEQUENCE: 7
uuucgauaaa guucauccgg 20

<210> SEQ ID NO 8
<211> LENGTH: 24
<212> TYPE: RNA
<213> ORGANISM: Artificial
<220> FEATURE:
<223> OTHER INFORMATION: Target specific sequence of the Cpf1 gRNA-Ecoli#2

<400> SEQUENCE: 8
acgggcggcu uaacaagcuc acca 24

<210> SEQ ID NO 9
<211> LENGTH: 24
<212> TYPE: RNA
<213> ORGANISM: Artificial
<220> FEATURE:
<223> OTHER INFORMATION: Target specific sequence of the Cpf1 gRNA-Ecoli#3

<400> SEQUENCE: 9
gauaaaguuc auccggcgga auau 24

<210> SEQ ID NO 10
<211> LENGTH: 20
<212> TYPE: RNA
<213> ORGANISM: Artificial
<220> FEATURE:
<223> OTHER INFORMATION: Target specific sequence of the gRNA-Ecoli#3

<400> SEQUENCE: 10
ccggagauaa ucgagaucgg 20

<210> SEQ ID NO 11
<211> LENGTH: 20
<212> TYPE: RNA
<213> ORGANISM: Artificial
<220> FEATURE:
<223> OTHER INFORMATION: Target specific sequence of the gRNA-Ecoli#4

<400> SEQUENCE: 11
gaacgugcgc gucugcugac 20

<210> SEQ ID NO 12
<211> LENGTH: 26
<212> TYPE: DNA
<213> ORGANISM: Artificial
<220> FEATURE:
<223> OTHER INFORMATION: PS189 with 5' phosphate group

<400> SEQUENCE: 12
aatggcactg agcttttgct cagtgc 26

<210> SEQ ID NO 13
<211> LENGTH: 26
<212> TYPE: DNA
<213> ORGANISM: Artificial
<220> FEATURE:
<223> OTHER INFORMATION: PS359 with 5' phosphate group

<400> SEQUENCE: 13
gcttgcactg agatttttct cagtgc 26

<210> SEQ ID NO 14
<211> LENGTH: 26
<212> TYPE: DNA
<213> ORGANISM: Artificial
<220> FEATURE:
<223> OTHER INFORMATION: PS137 with 5' phosphate group

<400> SEQUENCE: 14
attcgcactg agcttttgct cagtgc 26

<210> SEQ ID NO 15
<211> LENGTH: 452
<212> TYPE: DNA
<213> ORGANISM: Artificial
<220> FEATURE:
<223> OTHER INFORMATION: PCR product with 3' FITC

<400> SEQUENCE: 15
ttgtaaaacg acggccagtg aattgtaata cgactcacta tagggcgaat ggagacgagc 60
tccaccgcgg tggcggccgc tctagaacta gtggatccgt agacgcctca ccttctgcct 120
ctacgggtca caaaagcctg ggtcaccctg gttgccactg ttcctagttc aaagtcttct 180
tctgtctaat ccttcacccc tattctcgcc ttccactcca cctcccgctc agtcagactg 240
cgctactttg aaccggacca aaccaaacca aaccaaacca aaccaaacca gaccagacac 300
cccctcccgc ggaatcccag agaggccgaa ctgggataac cggatgcatt tgatttccca 360
cgccactgag tgcacctctg cagaaatggg cgttctggcc ctcgcgaggc agtgcgacct 420
gtcaccgccc ttcaggtgat taacatcatc ag 452

<210> SEQ ID NO 16
<211> LENGTH: 19
<212> TYPE: DNA
<213> ORGANISM: Artificial
<220> FEATURE:
<223> OTHER INFORMATION: Primer PS553

<400> SEQUENCE: 16
ttgtaaaacg acggccagt 19

<210> SEQ ID NO 17
<211> LENGTH: 35
<212> TYPE: DNA
<213> ORGANISM: Artificial
<220> FEATURE:
<223> OTHER INFORMATION: Primer PS554

<400> SEQUENCE: 17
gtctgaggtc tcgtcacctg aagggcggtg acagg 35

<210> SEQ ID NO 18
<211> LENGTH: 17
<212> TYPE: DNA
<213> ORGANISM: Artificial
<220> FEATURE:
<223> OTHER INFORMATION: PS495 with a 3' FITC

<400> SEQUENCE: 18
gtgattaaca tcatcag 17

<210> SEQ ID NO 19
<211> LENGTH: 13
<212> TYPE: DNA
<213> ORGANISM: Artificial
<220> FEATURE:
<223> OTHER INFORMATION: PS556

<400> SEQUENCE: 19
ctgatgatgt taa 13

<210> SEQ ID NO 20
<211> LENGTH: 26
<212> TYPE: DNA
<213> ORGANISM: Artificial
<220> FEATURE:
<223> OTHER INFORMATION: PS421 with 5' phosphate group

<400> SEQUENCE: 20
taaagcactg agatttttct cagtgc 26

<210> SEQ ID NO 21
<211> LENGTH: 50
<212> TYPE: DNA
<213> ORGANISM: Artificial
<220> FEATURE:
<223> OTHER INFORMATION: PS422

<400> SEQUENCE: 21
aggcccattc tgtaaggtca gtgtgattaa catcatcagt gacatcctat 50

<210> SEQ ID NO 22
<211> LENGTH: 106
<212> TYPE: DNA
<213> ORGANISM: Artificial
<220> FEATURE:
<223> OTHER INFORMATION: PS599, with a 5' phosphate group

<400> SEQUENCE: 22
caaagtagcg cagtctgact gagcgggagg tggagtggaa ggcgagaata ggggtgaagg 60
attagacaga gacagatatc gcgcttcctc ctactttgaa tgctat 106

<210> SEQ ID NO 23
<211> LENGTH: 35
<212> TYPE: DNA
<213> ORGANISM: Artificial
<220> FEATURE:
<223> OTHER INFORMATION: PS598, with a 5' biotin

<400> SEQUENCE: 23
catcgatctg atgcatctgt ctaatccttc acccc 35

<210> SEQ ID NO 24
<211> LENGTH: 42
<212> TYPE: RNA
<213> ORGANISM: Artificial

<220> FEATURE:
<223> OTHER INFORMATION: Generic crRNA sequence for Cas9
<220> FEATURE:
<221> NAME/KEY: misc_feature
<222> LOCATION: (1)..(20)
<223> OTHER INFORMATION: n is a, c, g, or u

<400> SEQUENCE: 24
nnnnnnnnnn nnnnnnnnnn guuuuagagc uaugcuguuu ug 42

<210> SEQ ID NO 25
<211> LENGTH: 89
<212> TYPE: RNA
<213> ORGANISM: Artificial
<220> FEATURE:
<223> OTHER INFORMATION: Generic tracrRNA sequence for Cas9

<400> SEQUENCE: 25
guuggaacca uucaaaacag cauagcaagu uaaaauaagg cuaguccguu aucaacuuga 60
aaaaguggca ccgagucggu gcuuuuuuu 89

<210> SEQ ID NO 26
<211> LENGTH: 94
<212> TYPE: RNA
<213> ORGANISM: Artificial
<220> FEATURE:
<223> OTHER INFORMATION: Generic single guide RNA for Cas9
<220> FEATURE:
<221> NAME/KEY: misc_feature
<222> LOCATION: (1)..(20)
<223> OTHER INFORMATION: n is a, c, g, or u

<400> SEQUENCE: 26
nnnnnnnnnn nnnnnnnnnn guuuuagagc uagaaaguua aaauaaggcu aguccguuau 60
caacuugaaa aaguggcacc gagucggugc uuuu 94

<210> SEQ ID NO 27
<211> LENGTH: 61
<212> TYPE: DNA
<213> ORGANISM: Artificial
<220> FEATURE:
<223> OTHER INFORMATION: PS645 with 5' Biotin

<400> SEQUENCE: 27
ttcggttccc gtgtgtcttt tggtctttct ggtgctcttc taggacttcg gtttgcgaat 60
c 61

<210> SEQ ID NO 28
<211> LENGTH: 37
<212> TYPE: DNA
<213> ORGANISM: Artificial
<220> FEATURE:
<223> OTHER INFORMATION: PS647 with 5' phosphate group

<400> SEQUENCE: 28
cgtgactcgt tttcgagtca cgcggtctga tgaaagc 37

<210> SEQ ID NO 29
<211> LENGTH: 19
<212> TYPE: DNA
<213> ORGANISM: Artificial
<220> FEATURE:
<223> OTHER INFORMATION: PS340

<400> SEQUENCE: 29
tgcttcagca gacagttcc 19

<210> SEQ ID NO 30
<211> LENGTH: 20
<212> TYPE: DNA
<213> ORGANISM: Artificial
<220> FEATURE:
<223> OTHER INFORMATION: PS860

<400> SEQUENCE: 30
gcatcaacga tcgcaatatg 20

<210> SEQ ID NO 31
<211> LENGTH: 6660
<212> TYPE: DNA
<213> ORGANISM: Escherichia coli

<400> SEQUENCE: 31
gcatcaacga tcgcaatatg ctgttgataa ctaacgttgt tatgttcgtg cagtgcctga 60
tcggtaaccg ttgggcgtgc ggcaataagc cagtcgagca gggcaacgtg gatcgccatg 120
aagattgggt taccggggat ctccgccagc acgcggtgga aatcaacgtc tgaacgaatg 180
aatgccgcgt tgttatccag cgactgactg ttgatttcca gtgcttttgc cagcaaatcg 240
atttgctcat cggtggcatg ttcagccgca tagcgcacca gactggattc aaagaacaga 300
cgtaattgtt cgaaatgggc aatcccaccg ggatgagaaa ggaaatcttt cgccatgccg 360
gaaagctcac cgatgatagt gtccgcagaa ggacgcgaga cgcgagcgcg ttcgccgttg 420
tttatttgca ccagaccttt gcgttttaac gctgccagcg cttcacgcac cgaaggacgc 480
ccgacgttaa agaacgccat cagttcgcgt tcagacggta attgttcacc ttcgccaaat 540
tcacgacggc ggatcatctg ttccagctct tcttccacca tttcggagag ttttttacgc 600
gccagcgggc ggctacgcaa gttgcgacca attgcaggtg aagaatcttc ggtttgcgaa 660
tcaaatgcgt tcataaggcc cattctgtaa ggtcagtgtg attaacatca tcagtgacat 720
cctatcacag gattgaaagt aggggaaaat ggcagggttt tctctttgtg cctcatcatt 780
accataatta acggaataat taactattgc gaaaaattaa tgtaacgcag ataaaaacat 840
cccgtttgaa ttatttataa gactattcac gagcattatg aatattatga atgtgttctt 900
acaaaataat cataagcgca tattttttaa tgaaaaatca cctcacctac aattaaaaac 960
acgacatccg caccataaat agccttgcaa aaaatataac atcgttgttt tcaatctgcc 1020
gtttatggga ttgaccgttt tcttttgaca cggagttcaa caatgttcgg cataattata 1080
tctgtcatcg tattaattac gatgggctat ttgatcctga aaaactacaa acctcaggtg 1140
gtgctggctg ccgcaggtat cttcctgatg atgtgcggtg tctggttagg gttcggtggt 1200
gtactcgatc ccaccaaaag cagcggctac ttgatcgtcg atatttataa tgaaatcctg 1260
cgcatgctgt ccaaccgcat tgccggattg gggctgtcga ttatggcggt gggcggttat 1320
gcccgctaca tggagcgcat aggggccagt cgcgcgatgg tgagcttgtt aagccgcccg 1380
ttaaaactca ttcgctcgcc gtatattatt ctgtcggcaa cttacgtcat cggccaaatc 1440
atggcgcagt ttattaccag cgcctccggt ctgggtatgt tgctgatggt caccttattt 1500
ccgacgctgg tgagtctggg agtaagtcgt ctctctgcgg tggcagttat cgcaaccacg 1560
atgtccattg agtgggggat tctggaaacg aactccattt ttgctgccca ggtagcggga 1620
atgaaaattg ccacatactt cttccactac cagcttccgg tcgcctcttg cgtcattatc 1680
tcggtggcga tctcccactt tttcgtgcaa cgcgcttttg acaaaaaaga taaaaatatc 1740

-continued

```
aatcacgaac aggcagagca aaaagctctc gataatgtcc cgccgctcta ttacgccatt   1800
ttacctgtga tgccgttaat cctgatgctc ggctcgctgt tcctcgccca cgtcgggctg   1860
atgcagtcag aactgcatct ggtggtggtg atgttactga gtttgactgt gacgatgttt   1920
gttgagttct tccgcaagca taacttgcgc gaaacaatgg acgatgtgca ggcgtttttt   1980
gacggcatgg gtacgcagtt tgccaacgtg gtaacgctgg tggtcgcggg tgaaatattt   2040
gcgaaaggct taacgacgat tggcactgtc gatgcggtta tcagggggc ggagcattct   2100
ggtctgggcg gtattggcgt gatgattatt atggcgctgg tcattgccat ttgtgccatt   2160
gtgatgggct ctggcaatgc gccgtttatg tcatttgcca gtcttattcc gaatatcgca   2220
gccggactac atgtaccagc ggttgtaatg attatgccga tgcattttgc cacgacgcta   2280
gcgcgcgcgg tttcgccgat tactgcggtg gtggtcgtta cgtcaggaat tgcaggcgtt   2340
tcgccttttg cggtggtgaa gcggacagcg atccccatgg cagtcggttt cgtggtgaat   2400
atgattgcca caatcacgct attttattaa gtcattaaaa agacaaaaca ggccgcctgg   2460
gcctgttttg tattacttca caacgcgtaa tgccggtcga ccaccgcgtg gtggctgcgg   2520
aggttcatcg tcaggatgag tgtcatcatc gtgatctggc ttgtcgccat caataaccga   2580
cataacggtt tcgttgtctg ccgatgcctc ttcatcattc atgatgctgg tatcttcatc   2640
gtaggcagct tcaggctcaa acatcgtgcc tgcgccattt tcacgggcgt agatagccag   2700
cacggcagcc agcggcacag aaacctgacg cggaatgcca ccaaagcgcg cgttaaagcg   2760
cacctcatca ttcgccagtt ccagattgcc gacagcacgc ggcgcaatgt tgagtacgat   2820
ttgcccgtca cgcgcatatt ccataggaac ctgcacgcca gggagcgtca catccaccac   2880
caggtgcggc gtgagctggt tatccagcaa ccactcatag aatgcacgca gcagataggg   2940
acgacgtggt gttagctgtg acaaatccat acagattaac tccggcccag acgcatttca   3000
cgttctgctt cagttaaaga agcaaggaaa gagtcacgct caaagacgcg ggtcatatag   3060
cctttcagct ctttcgcacc cgggccgctg aactcgatgc ccagttgcgg cagacgccac   3120
agcagcggag caagatagca atcgaccagg ctgaactcat cgctcaggaa gtacggcttc   3180
tgaccgaaga ccggcgcaat cgccagcagt tcttcgcgca gttgcttacg tgcggcatct   3240
gcttcagaag ctgaaccgtt gatgatggtg ttcatcagcg tgtaccagtc tttttcgatg   3300
cgatgcatgt acagacggct ttcaccgcga gctaccgggt aaacaggcat cagtggcgga   3360
tgcgggaaac gctcatccag atattccata atgatgcgag attcccacag ggtcagctca   3420
cgatccacca gggtcggaac gctctgattc gggttgaggt caatcagatc ctgaggcgga   3480
ttgtcctttt ccacgtgttc gatctcgaaa cttacacctt tctcagccag cacaatgcgg   3540
acctgatggc tatagatgtc agtaggaccg gaaaacagcg tcattaccga acgtttgttg   3600
gcagcgacag ccatgaaaac ctccaggtat agtcagaatt tttactgcta ccagccacca   3660
ggtggccagt cagaagttgt gttacccaat aaggaacgac tctctttgtt cgaaaatcaa   3720
acaaaaaatg agcaataccc gacatttggg cagaaaattg gatgatagtt taccagattt   3780
tgcgaccatt gtggtgagtc gatgccggaa atggggaaaa agagatgcgc tttagtctga   3840
aatagttgac ttagtccctt attggcgatg tggtttttgt tttacctgtc tgtcaggtgg   3900
cagcaaaaag caactttcca gtttttacgc tgattcagat tttagctata aaaaaacccg   3960
ccgaagcggg tttttttcgaa aattgttttc tgccggagca gaagccaatt aacgtttgga   4020
gaactgcgga cgacgacgtg ctttacgcag accgactttc ttacgttcaa cctgacgagc   4080
```

```
gtcacgagta acgaagccag ctttacgcag ttcagaacgc agggactcgt cgtattccat   4140
cagagcgcgg gtgataccgt gacggatcgc accagcctga ccagagatac caccaccttt   4200
aacggtgatg tacaggtcca gtttctcaac catgtcgacc agttccagcg gctgacgaac   4260
taccatgcgg gcagtttcac gaccgaagta ctgttccaga gaacgttggt tgattacgat   4320
tttaccgttg cccggtttga tgaaaacgcg agctgcggaa cttttgcggc gaccagtgcc   4380
gtagtattga ttttcagcca ttgcctataa tcccgattag atgtcaagaa cttgcggttg   4440
ctgtgccgcg tggttgtgct cgttacccgc gtaaactttc agtttacgga acatagcacg   4500
acccagcggg ccttttggca acatgccttt aaccgcgatt tcaatcacac gctcaggacg   4560
gcgagcaatc atctcttcaa aggtcgcttg tttgatacca ccgatgtggc cggtgtggtg   4620
atagtacact ttgtcagtac gcttgttgcc ggttacagca actttgtcag cgttcagaac   4680
gatgatgtaa tcaccggtat ctacgtgcgg agtgtattcc gctttgtgct taccgcgcag   4740
gcgacgagcc agttcagtag ccagacggcc cagagtttta ccggtcgcgt caacaacata   4800
ccagtcgcgt tttacggttt ctggtttagc tgtaaaagtt ttcattaaaa gcttacccaa   4860
taaatagtta cacgttggtg aacacccaaa cgtcttcaat tgttgaggtt cacacgacaa   4920
agtccggcaa acctacccct tcgaatagcc tatgccagca cacaaaaagt tttgggaaaa   4980
aaactttctt gtaacgtggg gtcgcaggat tatagagaag tcggggtcaa agatcgaccc   5040
ctttttgtga tttgtgacag gttttaaccc gccaaatgct cgcgcttcag atactcttcg   5100
ctttgcatct cttgcagacg tgacaggcaa cgctggaact caaacttcag ccgatcgccc   5160
tgataaattt catacagcgg cacttctgca ctcaccacta atttgacatg gcgctcgtaa   5220
aactcatcca ccagcgcaat aaagcgccgc gcttcgctct ccatcaaccg cgtcataact   5280
ggtacatcaa acaacatgac cgtatgaaag agacgtgaga gcgcaatata gtcatgctga   5340
ctgcgggcgt cgacgcacag cgtagtaaaa gagaccgcca gcgtctggtt ctcgacgccc   5400
attgttgcta atggccgatg gttgatttct aacgtcggtg aattttctcg tttccccccc   5460
gccagcgcca accatagttt atccatttgc gcccgggttt catcgtgaag tggcgaaagc   5520
cacagatgcg cctgagtgag tgtacgcaga cgataatcaa caccagcgtc cacgttcatt   5580
acatcacaat gctgtttaat ggcatcgatt gcaggcagaa aacgcgcacg ttgcaggcca   5640
tttcgataaa gttcatccgg cggaatattt gacgtcgcta ccagggtaat accgcgagcg   5700
aacagggctt tcatcagacc gccaagtagc atggcatcgg taatatcaga aacaaaaaat   5760
tcgtcaaaac agagcacgtc agtttcggct ttaaagcgat cggcaataat ttccagcgga   5820
tcggtctgcc cctgtaaggc agttagctct tcatgcaccc gcagcataaa acggtgaaag   5880
tgcaggcgct gtttccgctc tcccggcagg ctttgataga aaaggtccat cagccaggtt   5940
ttcccgcgtc ctacaccgcc ccacatatat aagccacgca ctggcgtatg ctttgtgtct   6000
tcgcgtttac cccacagctt accgacccgc gccattagcc cactcgtcct gggggctggt   6060
ggcgtgctat tgatgagttc ctgataaata atttccaggc ggctgacggc ctctttttga   6120
acgtcgtcgg gttgatggct gccttcatta agcgccttca ggtattgcga tgttggggta   6180
acgctttgca tgatcttatt gttattcctt gaataatcgg tgcgccgttg ttcacggttg   6240
acgaaaaaaa ggccgttcta cactacgcga tatgcagtcg ggattccact tctgtggaat   6300
taacggttat agtggcataa tcagccgcag gcatggagcc tgaagccaac accctacgga   6360
aacaaaagac aacgggagat gttcatgacc tgggaatatg cgctaattgg gttagtcgtc   6420
ggcatcatta ttggtgctgt ggccatgcgt tttggtaatc gtaaactacg ccagcaacag   6480
```

gcgttgcagt acgaactgga aaagaataaa gctgaactgg acgagtatcg cgaagagctg 6540
gttagccact ttgcccgcag cgcggaatta ctggatacca tggcgcacga ctatcgccag 6600
ctgtatcagc acatggcaaa aagctccagc agcctgctgc cggaactgtc tgctgaagca 6660

<210> SEQ ID NO 32
<211> LENGTH: 61
<212> TYPE: DNA
<213> ORGANISM: Artificial
<220> FEATURE:
<223> OTHER INFORMATION: PS648 with 5' biotin

<400> SEQUENCE: 32
ttcggttccc gtgtgtcttt tggtctttct ggtgctcttc taggagtagg tcagcactgc 60
c 61

<210> SEQ ID NO 33
<211> LENGTH: 44
<212> TYPE: RNA
<213> ORGANISM: Artificial
<220> FEATURE:
<223> OTHER INFORMATION: Generic single guide RNA for Cpf1
<220> FEATURE:
<221> NAME/KEY: misc_feature
<222> LOCATION: (21)..(44)
<223> OTHER INFORMATION: n is a, c, g, or u

<400> SEQUENCE: 33
uaauuucuac ucuuguagau nnnnnnnnnn nnnnnnnnnn nnnn 44

<210> SEQ ID NO 34
<211> LENGTH: 2262
<212> TYPE: DNA
<213> ORGANISM: Escherichia coli

<400> SEQUENCE: 34
gatcgctgtt gccggaattg gctcgaggat catgccgaca atcattgcca caaacacagc 60
gaagtaatgc catgcctgcg gcggcatacc gtcggggaca gggataagaa acatgacacc 120
catcaccacc agtggggcca atagtttcca tatattatct tttgctaaag acatacgggt 180
tctccgaaaa ttaatatttc caaatttatc aagtgcttaa ataattaaat ctgtgctaaa 240
aaccaggtaa ggatcagtag gtcagcactg ccgcctggac tgagatttcg ttcgatacac 300
tccctgtcga actgccggag ataatcgaga tcggcggggg ttcgaatgcc cccttttttgc 360 aataatgttt gcgcctcgcg ctgtagccag cgcaggcccc cctcgccacc gcgcgatgca 420
acgttggtat cgccgttgat cgccatcagt aggagcaagg tatcgagcaa tgccagttca 480
ggatctaacc cctgatccag cagagtgagg taatgcggca aggcgtgatt gatcaccagt 540
ggataacccg cttcggcttc accgcgtgcg ccggtaaggc caagctgttg gtacaaccgt 600
tgacctgccg tcagttgtga attattggta cgcagttcgc gatcggtcag gccacggcag 660
aaacttgccg ccgtagaaca aacggttgtt ggcgttaccg gttggttgag ttgaagcaaa 720
cggccaattg ccgcacatag cagccctaaa gaaaaaatgc tgcctttatg cgtgtttacg 780
cccgcagtgg cgcggaacat atcaccttcg caagccatac caattgggcg taatccgtgg 840
agtaccgctt ctggtgccat ttccgcacta caggcaccaa attcaatgaa acggggtagc 900
cagccctgaa tcgccagcgc gctgcggtgg aaatcttcca gcgccatatc tttgtgcgca 960
ccgcagttaa tgcgatccac gaggcctggt ttcggtgaca gattgacttc agtcagcatg 1020

```
gcgcgccagc ccagcagggc gtactcatcg attaatgacg tcgcaagctt tgtggtttta   1080

gttgacgttg caggcatcga catcgttcag cagtgcctcc atgcggttga gtaaatcggt   1140

cagttgatgg gtttttccac gcgcgcagac ggctgcgctt tgttcgcaca acaggcagcg   1200

gcgaggcggc agtgaatagt cgcggcggga gagaatttcg ccttcgggcg tcaggacatc   1260

gatatcccat aaccgcccga gaggatgact atgttcaagc tcaatggtgg cgagcttgag   1320

gtcgcgagcc ggggcggcaa tgctcaacat gccctccggc ccgctggcgg aaaccagtgc   1380

agcctgctcc tgaatttgcc agccctgttt tgcggctaag gcacgcaagg ctgtcacgcc   1440

atgattaaaa attcggcgtg tgacctcgct gtctttaatc ggcccaggcg caaccacggt   1500

aaaggagacc agtggaacag gatggcgctt gagccagacg tgttgccgtg cttgcctttc   1560

atcccggctg acgagcagct cgggaattga taccgcatgg tggctggcga gttcaggaag   1620

caggtgcatg gcttattcct tcacctgatg cacaacatcg atcaccgagc catcgcggta   1680

acgcacaacg gcaacgacgc ggtctgtgaa ttcaatcggc tgtggttcac cggtcagcag   1740

acgcgcacgt tcgcgcagcc actcaatgga aaccacttta atgcccgctt cctgcagacg   1800

ttctgccagt tccggacgtg ccgggttaac tgcgataccg tggtctgtga ccagaatatc   1860

gacactggag cctggggtga tgcaggtcag tacgttatcc accagagtcg gaatacgacc   1920

gcgtaccagc ggcgcgacga tgatggaaag cgcagaggca atcgcggtat cgcagtgacc   1980

accggaagca ccacgcagta cgccgtcaga gccggtcagc acgttaacgt tgaactgggt   2040

gtcaatttcc agcgcgctca gtaccaccac gtcgagacga tcaaccgatg cgcctttcga   2100

accccagtta gcgtactggt tggcgctgat ttcgatgtga ttggggttac gggccagcga   2160

ttgcgcagca tggctgtcaa agctctgcac atccagcagt ttgcggatca gacctttttc   2220

gtgcaggtca accatcgtcg cggtaatacc gccaagggcg aa                       2262
```

```
<210> SEQ ID NO 35
<211> LENGTH: 24
<212> TYPE: RNA
<213> ORGANISM: Artificial
<220> FEATURE:
<223> OTHER INFORMATION: Target specific sequence of the Cpf1 grRNA #1
      (Cpf1 crRNA-FMR1#1 (FMR1))

<400> SEQUENCE: 35

aaccggacca aaccaaacca aacc                                             24


<210> SEQ ID NO 36
<211> LENGTH: 24
<212> TYPE: RNA
<213> ORGANISM: Artificial
<220> FEATURE:
<223> OTHER INFORMATION: Target specific sequence of the Cpf1
      crRNA-009#2 (pPS009)

<400> SEQUENCE: 36

ccagucacga cguuguaaaa cgac                                             24


<210> SEQ ID NO 37
<211> LENGTH: 19
<212> TYPE: DNA
<213> ORGANISM: Artificial
<220> FEATURE:
<223> OTHER INFORMATION: Forward qPCR primer

<400> SEQUENCE: 37

tgtcgtgtgg gtagttgtg                                                   19
```

<210> SEQ ID NO 38
<211> LENGTH: 20
<212> TYPE: DNA
<213> ORGANISM: Artificial
<220> FEATURE:
<223> OTHER INFORMATION: Reverse qPCR primer

<400> SEQUENCE: 38
ctccgaagtc ccaatgctag 20

<210> SEQ ID NO 39
<211> LENGTH: 17
<212> TYPE: DNA
<213> ORGANISM: Artificial
<220> FEATURE:
<223> OTHER INFORMATION: Reverse qPCR primer

<400> SEQUENCE: 39
gcccagaaca gtggagc 17

<210> SEQ ID NO 40
<211> LENGTH: 208
<212> TYPE: DNA
<213> ORGANISM: Artificial
<220> FEATURE:
<223> OTHER INFORMATION: 208 bp fragment protected by the completely complementary Fmr1#1 gRNA

<400> SEQUENCE: 40
agtgaattcg tcaagactac agtacattgt gcctcgcgct cagtcagact gcgctacttt 60
gaaccggaaa tgtcgtgtgg gtagttgtgc aagatgaacc agcagacgta gtatactgta 120
tcaaggagcc aaaggagacc tgaagccctc ttgaagtagt actgatccgc gcaactaatc 180
tagcattggg acttcggagg gatccgtt 208

<210> SEQ ID NO 41
<211> LENGTH: 208
<212> TYPE: DNA
<213> ORGANISM: Artificial
<220> FEATURE:
<223> OTHER INFORMATION: 208 bp fragmentwith a mismatch for the Fmr1#1 gRNA (MM-1)

<400> SEQUENCE: 41
agtgaattcg tcaagactac agtacattgt gcctcgcgct cagtcagact gcgctacttt 60
gaaacggaaa tgtcgtgtgg gtagttgtgc aagatgaacc agcagacgta gtatactgta 120
tcaaggagcc aaaggagacc tgaagccctc ttgaagtagt actgatccgc gcaactaatc 180
tagcattggg acttcggagg gatccgtt 208

<210> SEQ ID NO 42
<211> LENGTH: 208
<212> TYPE: DNA
<213> ORGANISM: Artificial
<220> FEATURE:
<223> OTHER INFORMATION: 208 bp fragmentwith a mismatch for the Fmr1#1 gRNA (MM-2)

<400> SEQUENCE: 42
agtgaattcg tcaagactac agtacattgt gcctcgcgct cagtcagact gcgctacttt 60
gacccggaaa tgtcgtgtgg gtagttgtgc aagatgaacc agcagacgta gtatactgta 120
tcaaggagcc aaaggagacc tgaagccctc ttgaagtagt actgatccgc gcaactaatc 180

```
tagcattggg acttcggagg gatccgtt                                    208


<210> SEQ ID NO 43
<211> LENGTH: 208
<212> TYPE: DNA
<213> ORGANISM: Artificial
<220> FEATURE:
<223> OTHER INFORMATION: 208 bp fragmentwith a mismatch for the Fmr1#1
      gRNA (MM-3)

<400> SEQUENCE: 43

agtgaattcg tcaagactac agtacattgt gcctcgcgct cagtcagact gcgctacttt     60

gcaccggaaa tgtcgtgtgg gtagttgtgc aagatgaacc agcagacgta gtatactgta    120

tcaaggagcc aaaggagacc tgaagccctc ttgaagtagt actgatccgc gcaactaatc    180

tagcattggg acttcggagg gatccgtt                                       208


<210> SEQ ID NO 44
<211> LENGTH: 208
<212> TYPE: DNA
<213> ORGANISM: Artificial
<220> FEATURE:
<223> OTHER INFORMATION: 208 bp fragmentwith a mismatch for the Fmr1#1
      gRNA (MM-4)

<400> SEQUENCE: 44

agtgaattcg tcaagactac agtacattgt gcctcgcgct cagtcagact gcgctacttt     60

caaccggaaa tgtcgtgtgg gtagttgtgc aagatgaacc agcagacgta gtatactgta    120

tcaaggagcc aaaggagacc tgaagccctc ttgaagtagt actgatccgc gcaactaatc    180

tagcattggg acttcggagg gatccgtt                                       208


<210> SEQ ID NO 45
<211> LENGTH: 208
<212> TYPE: DNA
<213> ORGANISM: Artificial
<220> FEATURE:
<223> OTHER INFORMATION: 208 bp fragmentwith a mismatch for the Fmr1#1
      gRNA (MM-5)

<400> SEQUENCE: 45

agtgaattcg tcaagactac agtacattgt gcctcgcgct cagtcagact gcgctacttc     60

gaaccggaaa tgtcgtgtgg gtagttgtgc aagatgaacc agcagacgta gtatactgta    120

tcaaggagcc aaaggagacc tgaagccctc ttgaagtagt actgatccgc gcaactaatc    180

tagcattggg acttcggagg gatccgtt                                       208


<210> SEQ ID NO 46
<211> LENGTH: 208
<212> TYPE: DNA
<213> ORGANISM: Artificial
<220> FEATURE:
<223> OTHER INFORMATION: 208 bp fragmentwith a mismatch for the Fmr1#1
      gRNA (MM-6)

<400> SEQUENCE: 46

agtgaattcg tcaagactac agtacattgt gcctcgcgct cagtcagact gcgctactct     60

gaaccggaaa tgtcgtgtgg gtagttgtgc aagatgaacc agcagacgta gtatactgta    120

tcaaggagcc aaaggagacc tgaagccctc ttgaagtagt actgatccgc gcaactaatc    180

tagcattggg acttcggagg gatccgtt                                       208
```

<210> SEQ ID NO 47
<211> LENGTH: 1747
<212> TYPE: DNA
<213> ORGANISM: Escherichia coli

<400> SEQUENCE: 47
gcgactacgg ctccagtaca gacggcatcc ccggcgcaaa ccacagcaac acccgctgct 60
ggggcgaaga ccgcaggtaa tgttggttcg ttgaaatcgg caccgtccag ccattacact 120
ctgcagctga gcagttcctc taactacgac aacctgaacg gttgggcgaa gaaagagaat 180
ctgaaaaact acgttgtcta tgaaacgacg cgtaatggtc agccgtggta tgtcctggtt 240
tctggcgtgt acgcttcgaa agaagaggcg aaaaaagcgg tatctacatt gccagcagat 300
gtccaggcca aaaacccgtg ggcgaaaccg ctgcgtcagg tacaggccga tctgaagtaa 360
tcaaggttat ctcccgcaat ggtttatcgt tgcgggagtt gcctgaagcg ctggatgctg 420
tcggagcttt ctccacagcc ggagaaggtg taattagtta gtcagcatga agaaaaatcg 480 cgctttttg aagtgggcag ggggcaagta tcccctgctt gatgatatta aacggcattt 540
gcccaagggc gaatgtctgg ttgagccttt tgtaggtgcc gggtcggtgt ttctcaacac 600
cgacttttct cgttatatcc ttgccgatat caatagcgac ctgatcagtc tctataacat 660
tgtgaagatg cgtactgatg agtacgtaca ggccgcacgc gagctgtttg ttcccgaaac 720
aaattgcgcc gaggtttact atcagttccg cgaagagttc aacaaaagcc aggatccgtt 780
ccgtcgggcg gtactgtttt tatatttgaa ccgctacggt tacaacggcc tgtgtcgtta 840
caatctgcgc ggtgagttta acgtgccgtt cggccgctac aaaaaaccct atttcccgga 900
agcagagttg tatcacttcg ctgaaaaagc gcagaatgcc tttttctatt gtgagtctta 960
cgccgatagc atggcgcgcg cagatgatgc atccgtcgtc tattgcgatc cgccttatgc 1020
accgctgtct gcgaccgcca actttacggc gtatcacaca aacagtttta cgcttgaaca 1080
acaagcgcat ctggcggaga tcgccgaagg tctggttgag cgccatattc cagtgctgat 1140
ctccaatcac gatacgatgt taacgcgtga gtggtatcag cgcgcaaaat tgcatgtcgt 1200
caaagttcga cgcagtataa gcagcaacgg cggcacacgt aaaaaggtgg acgaactgct 1260
ggctttgtac aaaccaggag tcgtttcacc cgcgaaaaaa taattctcaa ggagaagcgg 1320
atgaaacagt atttgattgc cccctcaatt ctgtcggctg attttgcccg cctgggtgaa 1380
gataccgcaa aagccctggc agctggcgct gatgtcgtgc attttgacgt catggataac 1440
cactatgttc ccaatctgac gattgggcca atggtgctga aatccttgcg taactatggc 1500
attaccgccc ctatcgacgt acacctgatg gtgaaacccg tcgatcgcat tgtgcctgat 1560
ttcgctgccg ctggtgccag catcattacc tttcatccag aagcctccga gcatgttgac 1620
cgcacgctgc aactgattaa agaaaatggc tgtaaagcgg gtctggtatt taacccggcg 1680
acacctctga gctatctgga ttacgtgatg gataagctgg atgtgatcct gctgatgtcc 1740
gtcaacc 1747

<210> SEQ ID NO 48
<211> LENGTH: 1075
<212> TYPE: DNA
<213> ORGANISM: Escherichia coli

<400> SEQUENCE: 48
gaccacgcga tcgttttcga caataagatc ttcaaccgcc tgctggaaga tcatcaggtt 60
cggttggttc tccagcgccg tacgtaccgc ctgacggtag agcacacgat ccgcctgagc 120

```
tcgggtagcg cgaaccgccg gtcctttgct tgcgtttagt atcctaaact ggatacccgc    180

ctgatcgatc gctttcgcca tcagaccgcc gagtgcatcc acttctttta ccagatgtcc    240

cttcccaata ccgccgatcg ccgggttgca gctcatctgc cccagagtgt cgatattgtg    300

tgtcaaaagc agagtctgtt gacccatacg cgccgcggcc atcgcggcct cggtgcctgc    360

atgacccccg ccaatgatga tgacgtcaaa aggatccgga taaaacatgg tgattgcctc    420

gcataacgcg gtatgaaaat ggattgaagc ccgggccgtg gattctactc aactttgtcg    480

gcttgagaaa gacctgggat cctgggtatt aaaaagaaga tctatttatt tagagatctg    540

ttctattgtg atctcttatt aggatcgcac tgccctgtgg ataacaagga tccggctttt    600

aagatcaaca acctggaaag gatcattaac tgtgaatgat cggtgatcct ggaccgtata    660

agctgggatc agaatgaggg gttatacaca actcaaaaac tgaacaacag ttgttctttg    720

gataactacc ggttgatcca agcttcctga cagagttatc cacagtagat cgcacgatct    780

gtatacttat ttgagtaaat taacccacga tcccagccat tcttctgccg gatcttccgg    840

aatgtcgtga tcaagaatgt tgatcttcag tgtttcgcct gtctgttttg caccggaatt    900

tttgagttct gcctcgagtt tatcgatagc cccacaaaag gtgtcatatt cacgactgcc    960

aataccgatt gcgccaaagc ggactgcaga aagatcgggc ttctgttcct gcaatgcttc   1020

atagaaagga gaaaggttgt ccggaatatc tccggcaccg tgggtggagc tgata        1075
```

<210> SEQ ID NO 49
<211> LENGTH: 24
<212> TYPE: RNA
<213> ORGANISM: Artificial
<220> FEATURE:
<223> OTHER INFORMATION: Target specific sequence of the Cpf1 crRNA-Ecoli#4 (Target#1)

<400> SEQUENCE: 49

```
gcgaagguga acaauuaccg ucug                                            24
```

<210> SEQ ID NO 50
<211> LENGTH: 24
<212> TYPE: RNA
<213> ORGANISM: Artificial
<220> FEATURE:
<223> OTHER INFORMATION: Target specific sequence of the Cpf1 crRNA-Ecoli#5 (Target#1)

<400> SEQUENCE: 50

```
aucagaccgc caaguagcau ggca                                            24
```

<210> SEQ ID NO 51
<211> LENGTH: 24
<212> TYPE: RNA
<213> ORGANISM: Artificial
<220> FEATURE:
<223> OTHER INFORMATION: Target specific sequence of the Cpf1 crRNA-Ecoli#6 (Target#2)

<400> SEQUENCE: 51

```
ggagaacccg uaugucuuua gcaa                                            24
```

<210> SEQ ID NO 52
<211> LENGTH: 24
<212> TYPE: RNA
<213> ORGANISM: Artificial
<220> FEATURE:
<223> OTHER INFORMATION: Target specific sequence of the Cpf1 crRNA-Ecoli#7 (Target#2)

<400> SEQUENCE: 52
augcccgcuu ccugcagacg uucu 24

<210> SEQ ID NO 53
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#8 (Target #3, oriC)

<400> SEQUENCE: 53
ggauacuaaa cgcaagcaaa ggac 24

<210> SEQ ID NO 54
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#9 (Target #3, oriC)

<400> SEQUENCE: 54
ucgauagccc cacaaaaggu guca 24

<210> SEQ ID NO 55
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#10 (dam)

<400> SEQUENCE: 55
uucgcccaac cguucagguu gucg 24

<210> SEQ ID NO 56
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#11 (dam)

<400> SEQUENCE: 56
gcugccgcug gugccagcau cauu 24

<210> SEQ ID NO 57
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#12 (Target#1)

<400> SEQUENCE: 57
gcaucaaaga gcagguaauu acug 24

<210> SEQ ID NO 58
<211> LENGTH: 24
<212> TYPE: RNA
<213> ORGANISM: Artificial
<220> FEATURE:
<223> OTHER INFORMATION: Target specific sequence of the Cpf1
crRNA-Ecoli#13 (Target#1)

<400> SEQUENCE: 58
caucaucguc gcgccgcugg uacg 24

<210> SEQ ID NO 59
<211> LENGTH: 54
<212> TYPE: DNA
<213> ORGANISM: Artificial
<220> FEATURE:
<223> OTHER INFORMATION: PS1095 with 3' phosphate group (Target#1)

<400> SEQUENCE: 59
cagaagatga cagattagga agtgggcgtt cagacggtaa ttgttcacct tcgc 54

<210> SEQ ID NO 60
<211> LENGTH: 57
<212> TYPE: DNA
<213> ORGANISM: Artificial
<220> FEATURE:
<223> OTHER INFORMATION: PS1096 with 5' phosphate group (Target#1)

<400> SEQUENCE: 60
cagggcatga gcttttgctc atgccctgac cgatgccatg ctacttggcg gtctgat 57

<210> SEQ ID NO 61
<211> LENGTH: 24
<212> TYPE: RNA
<213> ORGANISM: Artificial
<220> FEATURE:
<223> OTHER INFORMATION: Target specific sequence of the Cpf1 crRNA-FMR1#2 (FMR1)

<400> SEQUENCE: 61
cauuccacug ugaaacaaac cuca 24

<210> SEQ ID NO 62
<211> LENGTH: 24
<212> TYPE: RNA
<213> ORGANISM: Artificial
<220> FEATURE:
<223> OTHER INFORMATION: Target specific sequence of the Cpf1 crRNA-FMR1#3 (FMR1)

<400> SEQUENCE: 62
cggucuagca uugggacuuc ggag 24

<210> SEQ ID NO 63
<211> LENGTH: 54
<212> TYPE: DNA
<213> ORGANISM: Artificial
<220> FEATURE:
<223> OTHER INFORMATION: PS1161 with 3' phosphate group (FMR1)

<400> SEQUENCE: 63
cagaagatga cagattagga agtggaaagt tgaggtttgt ttcacagtgg aatg 54

<210> SEQ ID NO 64
<211> LENGTH: 30
<212> TYPE: DNA
<213> ORGANISM: Artificial
<220> FEATURE:
<223> OTHER INFORMATION: PS601 with 5' Biotin (FMR1)

<400> SEQUENCE: 64
catcgatctg atgcacttca cccctattct 30

<210> SEQ ID NO 65
<211> LENGTH: 53
<212> TYPE: DNA
<213> ORGANISM: Artificial
<220> FEATURE:
<223> OTHER INFORMATION: PS1162 with 5' phosphate group (FMR1)

<400> SEQUENCE: 65
cagggcatga gcttttgctc atgccctgga gctctccgaa gtcccaatgc tag 53

<210> SEQ ID NO 66
<211> LENGTH: 2250
<212> TYPE: DNA
<213> ORGANISM: Homo sapiens

<400> SEQUENCE: 66
cccagagcag ggcgtcatgc acaagaaagc tttgcacttt gcgaaccaac gataggtggg 60
ggtgcgtgga ggatggaaca cggacggccc ggcttgctgc cttcccaggc ctgcagtttg 120
cccatccacg tcagggcctc agcctggccg aaagaaagaa atggtctgtg atccccccag 180
cagcagcagc agcagcagca gcagcagcag cagcagcagc agcagcagca gcagcagcat 240
tcccggctac aaggaccctt cgagccccgt tcgccggccg cggacccggc ccctccctcc 300
ccggccgcta gggggcgggc ccggatcaca ggactggagc tgggcggaga cccacgctcg 360
gagcggttgt gaactggcag gcggtgggcg cggcttctgt gccgtgcccc gggcactcag 420
tcttccaacg gggccccgga gtcgaagaca gttctagggt tcagggagcg cgggcggctc 480
ctgggcggcg ccagactgcg gtgagttggc cggcgtgggc caccaaccca atgcagccca 540
gggcggcggc acgagacaga acaacggcga acaggagcag ggaaagcgcc tccgataggc 600
caggcctagg gacctgcggg gagagggcga ggtcaacacc cggcatgggc ctctgattgg 660
ctcctgggac tcgccccgcc tacgcccata ggtgggcccg cactcttccc tgcgccccgc 720
ccccgcccca acagcctaca gctgttgtta gtccactcgc acgcctcgaa tcccgtccga 780
actcgtcatt ggctgcttcc tagcggcctg tgttgattgg ctgcccgaag atccgccctc 840
ctgccgtggg cccagccccg caaatgcgca gctaagcggg tggcaagggg cgggtggagc 900
gcggggcgcg acggcggagg ggggcgtggg cagccggacg taccctggca gggagcagca 960
ggtggcggcg gtgcatgggg cctggcccca ccagcgggca ctggcccaca gccacggccg 1020
gggggccatc tagctggaga gagaagggac aggtgacccg atcggagccc agcccagccc 1080
tcagcggtgg ggcgagagac agcgagggga atcgaggttg ggaggttat ctagggagat 1140 cccggaggga atctggtgag gcctgaacgg agggagatct ggggctgaat aaagggcttc 1200
tgccctctaa agtcgcaaag acgtagggtg agccctatat ctggacgggg agaccaggag 1260
ccagggaggg gatctgcaga atgggcagca ggtctgaggc aggggaaaga gaggggtctt 1320
acatgggaag gtggatccgt ggcccgggga ctggggaccc ccgtgacagc tggaaggaga 1380
agaaagaggc atagggcgcg tggaggggcg aaggagggcg gtggcgcggc gtgccccagc 1440
gtgggtccct tccctcctcc aggtgtctat acacgccccg cggagcagac ggcccacctc 1500
ctcccggtcc tccggggaag gggacacatg agggactcac ctgtggctcc ctctgcctgc 1560
agcaactcca tccgctcctg caactgccgg acgtgtgcct ctaggtcccg gttccgagcc 1620
tctgcctcgc gtagttgact gtggggaggt aaggacggtg agtccgtccg ggccggacga 1680
gaggggatgc caagggttgc caccggcccg catcccggcc ccggccccgg ccccgatccc 1740
gacctggcga agttctggtt gtccgtgcgg atggcctcca tctcccggct caggctctgc 1800

```
cgggtgagca cctcctcctc cagggcttcc tggagctccc gcagcgtcac ctcggcctca   1860
gcctctgccg cagggacagc cgctggaact gccacttcag cctgtgtatg gggaccaggc   1920
ttaaggctgc ctgtggctcc tggaagactc aggacttggg cactggttcc aggctaggaa   1980
tccttgttta tcccctactc ctccgtcccc tcaacatttc tggaatcccc atagctcctg   2040
caatgatcca agccccctcc cttccctacc tccctcagcc ccatccctga gtctggtcct   2100
ctaaatctac acagggacca gagggctggt gctcaaacac taacacaacc tatgtccctc   2160
tgctgctcaa aatccctcca gctccctaat gccctcacga caaaaggcct tgctgggttt   2220
tgtttcctgc tggcctctcc agccttctca                                     2250
```

<210> SEQ ID NO 67
<211> LENGTH: 1487
<212> TYPE: DNA
<213> ORGANISM: Homo sapiens

<400> SEQUENCE: 67

```
aatgcactta acagtgtctt acggtaaaaa caaaatttca tccaccaatt atgtgttgag     60
cgcccactgc ctaccaagca caaacaaaac cattcaaaac cacgaaatcg tcttcacttt    120
ctccagatcc agcagcctcc cctattaagg ttcgcacacg ctattgcgcc aacgctcctc    180
cagagcgggt cttaagataa aagaacagga caagttgccc cgccccattt cgctagcctc    240
gtgagaaaac gtcatcgcac atagaaaaca gacagacgta acctacggtg tcccgctagg    300
aaagagaggt gcgtcaaaca gcgacaagtt ccgcccacgt aaaagatgac gcttggtgtg    360
tcagccgtcc ctgctgcccg gttgcttctc ttttgggggc ggggtctagc aagagcaggt    420
gtgggtttag gaggtgtgtg tttttgtttt tcccaccctc tctccccact acttgctctc    480
acagtactcg ctgagggtga acaagaaaag acctgataaa gattaaccag aagaaaacaa    540
ggagggaaac aaccgcagcc tgtagcaagc tctggaactc aggagtcgcg cgctaggggc    600
cggggccggg gccggggcgt ggtcggggcg ggcccggggg cgggcccggg gcggggctgc    660
ggttgcggtg cctgcgcccg cggcggcgga ggcgcaggcg gtggcgagtg ggtgagtgag    720
gaggcggcat cctggcgggt ggctgtttgg ggttcggctg ccgggaagag gcgcgggtag    780
aagcgggggc tctcctcaga gctcgacgca tttttacttt ccctctcatt tctctgaccg    840
aagctgggtg tcgggctttc gcctctagcg actggtggaa ttgcctgcat ccgggccccg    900
ggcttcccgg cggcggcggc ggcggcggcg gcgcagggac aagggatggg gatctggcct    960
cttccttgct ttcccgccct cagtacccga gctgtctcct tcccggggac ccgctgggag   1020
cgctgccgct gcgggctcga gaaaagggag cctcgggtac tgagaggcct cgcctggggg   1080
aaggccggag ggtgggcggc gcgcggcttc tgcggaccaa gtcggggttc gctaggaacc   1140
cgagacggtc cctgccggcg aggagatcat gcgggatgag atgggggtgt ggagacgcct   1200
gcacaatttc agcccaagct tctagagagt ggtgatgact tgcatatgag ggcagcaatg   1260
caagtcggtg tgctccccat tctgtgggac atgacctggt tgcttcacag ctccgagatg   1320
acacagactt gcttaaagga agtgactatt gtgacttggg catcacttga ctgatggtaa   1380
tcagttgtct aaagaagtgc acagattaca tgtccgtgtg ctcattgggt ctatctggcc   1440
gcgttgaaca ccaccaggct ttgtattcag aaacaggagg gaggtcc                  1487
```

<210> SEQ ID NO 68
<211> LENGTH: 1272
<212> TYPE: DNA

<213> ORGANISM: Homo sapiens

<400> SEQUENCE: 68
aagcgagaat ggaggaatac aagccaaagg gaaggaaggg gacgaaggcg gacagggagt 60
gacctcttcc tccaaccccc gggcccgctg ggagcggcgc gaggccagag gcccttgaga 120
ggctcgggct gtcctggggg cctcagtcct ctgcctgtac cccatggggg accctgctgc 180
caccaggcgc cccgcactca ctcgacctgc agcgtgctgg gtttaatctt cacctcaacc 240
ttgtaggagg agccggtgag cagcttgatg gtgcggttct ggccgaagcg ctgcccgtcc 300
accttgtaaa agaccgggcc gtcattaggc tggatgcgca gcgcgatgga gaggcgcacg 360
aggcccggca ggtcccccat gtctgggcga gggtctggcg cggcggctcc ggggggcgga 420
ggacagcgcc ggctgcggcc gagtggctgg agcgcgaggg gcggagagga agcgcgggga 480
gggtgaggga ggtggtggag ctgaggctgc cgctaggaac ccgcgccgtc gccgccgtcc 540
gcccgggctt ttgaggagca gctccttagg ctgtggcccc cctccccact cggcgaggaa 600
gcgggcccaa gagacggctc caaggccgcg cgcttcccca tcccccgctc cagtgctgcg 660
ccctccacgc acccgaaggc tcgctctggc ccgcaggccg ccgcgcagat ccgcgcagct 720
gggggcgagg gagttaatcc tgtttacgca ccacaatccc cttcagctgg ggaagcggac 780
atttaggctc ctcctagaac agccccgggc aggaggagga gaggtttggg aggcactggg 840
aaggcgctgg agttaagcga ccactatgcc aaggagcgag acccccggaa tctggatacc 900
gcctcggcca gctacgtgag gtggacactg ctgctcgcgg atccggcgcc agccaggcgg 960
gaggaggctg aggggggta aagggaggcg ggaagggggg acaggaaacc gctagccggt 1020
gatttaaatt tcaggaaata tgagtctttc caaagcttag gggaaatggc cgaggaaagg 1080
cgcaattcca cgtgatggag ccacgctgga tgaggaatgg atgcaagagg aagaaaataa 1140
ccatattcaa ggagctacat cttcttgtgg gtgtacattt ccattatacg tatgctcgtc 1200
ccaaaaatga cacatacata aatatatgta atgaatcaca tatatttaca cagattttga 1260
agggtgagct at 1272

<210> SEQ ID NO 69
<211> LENGTH: 2352
<212> TYPE: DNA
<213> ORGANISM: Homo sapiens

<400> SEQUENCE: 69
gggcagtggg acacttagcc tctctaaaag cacctccacg gctgtttgtg tcaagccttt 60
attccaagag cttcactttt gcgaagtaat gtgcttcaca cattggcttc aaagtaccca 120
tggctggttg caataaacat taaggaggcc tgtctctgca cccggagttg ggtgccctca 180
tttcagatga tttcgagggt gcttgacaag atctgaagga ccctcggact ttagagcacc 240
acctcggacg cctggcaccc ctgccgcgcg ggcacggcga cctcctcagc tgccaggcca 300
gcctctgatc cccgagaggg tcccgtagtg ctgcagggga ggtggggacc cgaataaagg 360
agcagtttcc ccgtcggtgc cattatccga cgctggctct aaggctcggc cagtctgtct 420
aaagctggta caagtttgct ttgtaaaaca aaagaaggga aagggggaag gggaccctgg 480
cacagatttg gctcgacctg gacataggct gggcctgcaa gtccgcgggg accgggtcca 540
gaggggcagt gctgggaacg cccctctcgg aaattaactc ctcagggcac ccgctcccct 600
cccatgcgcc gccccactcc cgccggagac taggtcccgc gggggccacc gctgtccacc 660
gcctccggcg gccgctggcc ttgggtcccc gctgctggtt ctcctccctc ctcctcgcat 720

```
tctcctcctc ctctgctcct cccgatccct cctccgccgc ctggtccctc ctcctcccgc    780

cctgcctccc cgcgcctcgg cccgcgcgag ctagacgtcc gggcagcccc cggcgcagcg    840

cggccgcagc agcctccgcc ccccgcacgg tgtgagcgcc cgacgcggcc gaggcggccg    900

gagtcccgag ctagccccgg cggccgccgc cgcccagacc ggacgacagg ccacctcgtc    960

ggcgtccgcc cgagtccccg cctcgccgcc aacgccacaa ccaccgcgca cggcccccctg   1020

actccgtcca gtattgatcg ggagagccgg agcgagctct tcggggagca gcgatgcgac   1080

cctccgggac ggccggggca gcgctcctgg cgctgctggc tgcgctctgc ccggcgagtc   1140

gggctctgga ggaaaagaaa ggtaagggcg tgtctcgccg gctcccgcgc cgcccccgga   1200

tcgcgccccg gaccccgcag cccgcccaac cgcgcaccgg cgcaccggct cggcgcccgc   1260

gcccccgccc gtcctttcct gtttccttga gatcagctgc gccgccgacc gggaccgcgg   1320

gaggaacggg acgtttcgtt cttcggccgg gagagtctgg ggcgggcgga ggaggagacg   1380

cgtgggacac cgggctgcag gccaggcggg gaacggccgc cgggacctcc ggcgccccga   1440

accgctccca actttcttcc ctcactttcc ccgcccagct gcgcaggatc ggcgtcagtg   1500

ggcgaaagcc gggtgctggt gggcgcctgg ggccggggtc ccgcacgtgc gccccgcgct   1560

gtcttcccag ggcgcgacgg ggtcctggcg cgcacccgag gggcgggcgc tgcccacccg   1620

ccgagactgc actgtttagg gaagctgagg aaggaaccca aaaatacagc ctcccctcgg   1680

accccgcggg acaggcggct ttctgagagg acctccccgc ctccgccctc cgcgcaggtc   1740

tcaaactgaa gccggcgccc gccagcctgg ccccggcccc tctccaggtc cccgcgatcc   1800

tcgttcccca gtgtggagtc gcagcctcga cctgggagct gggagaactc gtctaccacc   1860

acctgcggct cccggggagg ggtggtgctg gcggcggtta gtttcctcgt tggcaaaagg   1920

caggtggggt ccgacccgcc ccttgggcgc agaccccggc cgctcgcctc gcccggtgcg   1980

ccctcgtctt gcctatccaa gagtgccccc cacctcccgg ggaccccagc tccctcctgg   2040

gcgcccgcgc cgaaagcccc aggctctcct tcgatggccg cctcgcggag acgtccgggt   2100

ctgctccacc tgcagccctt cggtcgcgcc tgggcttcgc ggtggagcgg gacgcggctg   2160

tccggccact gcaggggggg atcgcgggac tcttgagcgg aagccccgga agcagagctc   2220

atcctggcca acaccatggt gtttcaaaat ggggctcaca gcaaacttct cctcaaaacc   2280

cggagacttt ctttcttgga tgtctctttt tgctgtttga agaatttgag ccaaccaaaa   2340

tattaaacct gt                                                        2352
```

```
<210> SEQ ID NO 70
<211> LENGTH: 1711
<212> TYPE: DNA
<213> ORGANISM: Homo sapiens

<400> SEQUENCE: 70

tgaggtttgt ttcacagtgg aatgtaaagg gttgcaagga ggtgcatcgg cccctgtgga     60

caggacgcat gactgctaca cacgtgttca ccccaccctc tggcacaggg tgcacataca    120

gtaggggcag aaatgaacct caagtgctta acacaatttt taaaaaatat atagtcaagt    180

gaaagtatga aaatgagttg aggaaaggcg agtacgtggg tcaaagctgg gtctgaggaa    240

aggctcacat tttgagatcc cgactcaatc catgtccctt aaagggcaca gggtgtctcc    300

acagggccgc ccaaaatctg gtgagagagg gcgtagacgc ctcaccttct gcctctacgg    360

gtcacaaaag cctgggtcac cctggttgcc actgttccta gttcaaagtc ttcttctgtc    420
```

```
taatccttca cccctattct cgccttccac tccacctccc gctcagtcag actgcgctac    480

tttgaaccgg accaaaccaa accaaaccaa accaaaccaa accagaccag acacccccctc   540

ccgcggaatc ccagagaggc cgaactggga taaccggatg catttgattt cccacgccac    600

tgagtgcacc tctgcagaaa tgggcgttct ggccctcgcg aggcagtgcg acctgtcacc    660

gcccttcagc cttcccgccc tccaccaagc ccgcgcacgc ccggcccgcg cgtctgtctt    720

tcgacccggc accccggccg gttcccagca gcgcgcatgc gcgcgctccc aggccacttg    780

aagagagagg gcggggccga ggggctgagc ccgcgggggg agggaacagc gttgatcacg    840

tgacgtggtt tcagtgttta cacccgcagc gggccggggg ttcggcctca gtcaggcgct    900

cagctccgtt tcggtttcac ttccggtgga gggccgcctc tgagcgggcg gcgggccgac    960

ggcgagcgcg ggcggcggcg gtgacggagg cgccgctgcc agggggcgtg cggcagcgcg   1020

gcggcggcgg cggcggcggc ggcggcggag gcggcggcgg cggcggcggc ggcggcggct   1080

gggcctcgag cgcccgcagc ccacctctcg ggggcgggct cccggcgcta gcagggctga   1140

agagaagatg gaggagctgg tggtggaagt gcggggctcc aatggcgctt tctacaaggt   1200

acttggctct agggcaggcc ccatcttcgc ccttccttcc ctccctttttc ttcttggtgt  1260

cggcgggagg caggcccggg gccctcttcc cgagcaccgc gcctgggtgc cagggcacgc   1320

tcggcgggat gttgttggga gggaaggact ggacttgggg cctgttggaa gcccctctcc   1380

gactccgaga ggccctagcg cctatcgaaa tgagagacca gcgaggagag ggttctcttt   1440

cggcgccgag ccccgccggg gtgagctggg gatgggcgag ggccggcggc aggtactaga   1500

gccgggcggg aagggccgaa atcggcgcta agtgacggcg atggcttatt cccccctttcc  1560

taaacatcat ctcccagcgg gatccgggcc tgtcgtgtgg gtagttgtgg aggagcgggg   1620

ggcgcttcag ccgggccgcc tcctgcagcg ccaagagggc ttcaggtctc ctttggcttc   1680

tcttttccgg tctagcattg ggacttcgga g                                   1711
```

<210> SEQ ID NO 71
<211> LENGTH: 2266
<212> TYPE: DNA
<213> ORGANISM: Homo sapiens

<400> SEQUENCE: 71

```
aaccacgtcc tctcctttgg ggcagaaatc tctgggagta ggggcaaggt agtttaacca     60

cgaacggggt ggggactaaa caaccctagc acctctaagg tgcccccagg aggtcttgcc    120

aaggagtctt ccacagggag agtcatcctg cccgttgttc tggatcttga aacttgggag    180

acccacacca aaggagggaa ccggttcctt taccctttaa gcgcgtcgtg tcctccaccg    240

cctcttctct tggcccgact ggctctggtt tccttcacgt tcccagcctc caaattggcg    300

tccgccccat ggctcgtgta ggacgctaaa agcacggtaa atcccagggc gatctccagc    360

agacgccctc gacgcatgat gccgagccgc caccggctcc cgccgcctct tgccgcgccc    420

ggggctcggt ctgcggccgc cgctgcgccc tgaagcgcac cgcgccgccg gggtcccgct    480

atcccgccgc ccgtccccccg ggccgggctc ctcccgcctt ctccaggcgc tgctcccact   540

tcaggcggcc cctgccagct gcaacacaga gacaaatccc cgaggcgggg agactttcag    600

ggcatcggga tgctgaagcc tcgcggtccc cattcccaag cccaacccgt gcgccgcctg    660

cgcgtggcgc agttaatttg ggtaagggaa gaccgtttgg tccacagctg gctggaaagc    720

ccaggccccc ggcggcagca gccccggccg atccctcggc ctcccgggcc ccgccagaag    780

agcgcggcgc aaagtaccca tatccccagc ggtcctaagc cccgggcgag ctctctgggt    840
```

```
ttattttttt tagcggcacg aattgcgcgc gatgcgcgct ctgaacgccc cactcctcag    900

cctgccctct ccgccaggct ggaagccagc cgcgccgtcc ccgccgactc cgggcgatgc    960

caccgccccc cgaacatctg acgcggagcc cggcaccaag agccccgggc caggaagctg   1020

tcaggcaggg gagggccagc gccagctgtg gacgttccgg gacagcccct caccccagtc   1080

cctgtccctg ccctcggcgc ggcgcaaacg caaaagcctc cgtggccgca gctccagccc   1140

cggtggccgc ccgacccccg tcgggacccc ggctgcaccc actggagaag cggcggctcc   1200

gactcccgag gaggcggcgg cggctgctcc cagtcgtggc cgctacagcc actgctcggc   1260

tccgctcgca gctgtcccag ctgtggctcc tgtccgcttg tggcacccac agtctctgcc   1320

gcggctcccg cagccccctc ctttccccac ctcttcaagt atcgtccgcg cagcggtttc   1380

tcgcgagaga aatacttttt ttaaaaaaag aaagaaaaag aaaatgacac cccctccttc   1440

gtcgccctca tcaccacccc accccccggc cccatccatc ctccctttcc actccccttt   1500

gccagcctcc gcctcggtgc ggggcctctc gctcgcagga ttagcgcagt gggaggaggc   1560

agaggtgatc aggtcctgcc cggcctggga ctttttgtct tgaggtgggg aggggagaaa   1620

tgggaagagg tggagtagcg gttttagccc gctctgcggc tgcgaggttt agatccgaga   1680

ttaacctctc ccgcgatagg tgaagcccta ccggagcaga aagctgttcc acctgcacca   1740

agaatgcgcg ctggagacgg ttgccccgga ggccctggcc cgagagaaaa ccagtccccg   1800

ctgcccgcgc ctcccggtag cgcgctccct gcgcctctcc cgccggacac tcagcagacg   1860

ccggaggccg ggaggctaag actgggcgcg tcgcaggccg ggaccgcggc agaggctgct   1920

gtgccgaccg aggagagggc tctgccgccc ccacttgccc tgggtgtcga gagcccactc   1980

cagacgcggc tcttctgagg ctcaattcaa gccacccagg cctgaatcca gggtgctctc   2040

tctaagtcgg tgtccaaccc aggggcctgt aaatgttgga acctaggatg taggatggga   2100

gcggtgaagg gatggtcctc ttgcccagcc cagattaaga ctggggttca tctggaggac   2160

tctacttaca ccctcccggt cccctcgccc tcccccacac acagctgcct ctccccagga   2220

tatgcgcggc acagtgaatt tagtggcttt gaaaggtata gtattt                  2266
```

<210> SEQ ID NO 72
<211> LENGTH: 1643
<212> TYPE: DNA
<213> ORGANISM: Homo sapiens

<400> SEQUENCE: 72

```
ggtcagagca ggggtgcact cccataaaga aacgccccca ggtcgggact cattcctgtg     60

ggcggcatct tgtggccata gctgcttctc gctgcactaa tcacagtgcc tctgtgggca    120

gcaggcgctg accacccagg cctgccccag accctctcct cccttccggg gcgctgcgct    180

gggaccgatg gggggcgcca ggcctgtgga caccgccctg caggggcctc tccagctcac    240

tgggggtggg gtgggggtca cacttggggt cctcaggtcg tgccgaccac gcgcattctc    300

tgcgctctgc gcaggagctc gcccaccctc tccccgtgca gagagccccg cagctggctc    360

cccgcagggc tgtccgggtg agtatggctc tggccacggg ccagtgtggc gggagggcaa    420

accccaaggc cacctcggct cagagtccac ggccggctgt cgccccgctc caggcgtcgg    480

cgggggatcc tttccgcatg ggcctgcgcc cgcgctcggc gccccctcca cggccccgcc    540

ccgtccatgg ccccgtcctt catgggcgag cccctccatg gccctgcccc tccgcgcccc    600

acccctccct cgccccacct ctcaccttcc tgccccgccc ccagcctccc cacccctcac    660
```

```
cggccagtcc cctcccctat cccgctccgc ccctcagccg ccccgcccct cagccggcct    720

gcctaatgtc cccgtcccca gcatcgcccc gccccgcccc cgtctcgccc cgcccctcag    780

gcggcctccc tgctgtgccc cgccccggcc tcgccacgcc cctacctcac cacgcccccc    840

gcatcgccac gccccccgca tcgccacgcc tcccttacca tgcagtcccg ccccgtccct    900

tcctcgtccc gcctcgccgc gacacttcac acacagcttc gcctcacccc attacagtct    960

caccacgccc cgtcccctct ccgttgagcc ccgcgccttc gcccgggtgg ggcgctgcgc   1020

tgtcagcggc cttgctgtgt gaggcagaac ctgcgggggc aggggcgggc tggttccctg   1080

gccagccatt ggcagagtcc gcaggctagg gctgtcaatc atgctggccg gcgtggcccc   1140

gcctccgccg gcgcggcccc gcctccgccg gcgcagcgtc tgggacgcaa ggcgccgtgg   1200

gggctgccgg gacgggtcca agatggacgg ccgctcaggt tctgctttta cctgcggccc   1260

agagccccat tcattgcccc ggtgctgagc ggcgccgcga gtcggcccga ggcctccggg   1320

gactgccgtg ccgggcggga gaccgccatg gcgaccctgg aaaagctgat gaaggccttc   1380

gagtccctca agtccttcca gcagcagcag cagcagcagc agcagcagca gcagcagcag   1440

cagcagcagc agcagcaaca gccgccaccg ccgccgccgc cgccgccgcc tcctcagctt   1500

cctcagccgc cgccgcaggc acagccgctg ctgcctcagc cgcagccgcc cccgccgccg   1560

cccccgccgc cacccggccc ggctgtggct gaggagccgc tgcaccgacc gtgagtttgg   1620

gcccgctgca gctccctgtc ccg                                           1643
```

<210> SEQ ID NO 73
<211> LENGTH: 1816
<212> TYPE: DNA
<213> ORGANISM: Homo sapiens

<400> SEQUENCE: 73

```
ctctgcaggt cctcactgta actggaaaaa cacgacctcg ccctcgggaa ggctttctgt     60

gcgcctcacc tcaggatgag ggtgggtgta ggggacacct cccagaaacc cctaacctcc    120

cagtcggtta aagaagaggg gatagggtca agggatgcga cagagctgtg tggtttccgg    180

atgggaaacc tcagtcgttt aggcacccct ccgctcgagt cacttccgaa gcagtcgatt    240

cttggggaga agcgctgcgg aaaggggcga ctccgatgca gatggccctg tcccggcgcc    300

ccaggtcgtc gcgcgcgcag ctgcggtagt cactgcgcct ccccgccccc actcctggat    360

gccccccttc cctctcccgg ccagactctg agcaggagct ccgcccccag cgcgccgccc    420

cagccccggc gccttaaaag ccgggcgcac cgccccgccg cgccctgcct gccgcacctc    480

tcctttcttc tgtagctcgc gttgaagccg cacgtccggc cccgatcccg gcaccatgag    540

cttcggctcg gagcactacc tgtgctcctc ctcctcctac cgcaaggtgt tcggggatgg    600

ctctcgcctg tccgcccgcc tctctggggc cggcggcgcg ggcggcttcc gctcgcagtc    660

gctgtcccgc agcaatgtgg cctcctcggc cgcctgctcc tcggcctcgt cgctcggcct    720

cggcctggcc tatcgccggc cgccggcgtc cgacgggctg gacctgagcc aggcggcggc    780

gcgcaccaac gagtacaaga tcatccgcac caacgagaag gagcagctgc agggcctcaa    840

cgaccgcttc gccgtgttca tcgagaaggt gcatcagctg gagacgcaga accgcgcgtt    900

ggaggccgag ctggccgcgc tgcgacagcg ccacgctgag ccgtcgcgcg tcggcgagct    960

cttccagcgc gagctgcgcg acctgcgcgc gcagctggag gaggccagct cggctcgctc   1020

gcaggccctg ctggagcgcg acgggctggc ggaggaggtg cagcggctgc gggcgcgctg   1080

cgaggaggag agccgcggac gcgaaggcgc cgagcgcgcc ctgaaggcgc agcagcgcga   1140
```

```
cgtggacggc gccacgctgg cccgcctgga cctggagaag aaggtggagt cgctgctgga   1200

cgagctggcc ttcgtacgcc aggtgcacga cgaggaggta gccgagctgc tggccacgct   1260

gcaggcgtcg tcgcaggccg cggccgaggt ggacgtgact gtggctaaac cagacctgac   1320

ctcggctctg agggagatcc gcgcccagta tgagtccctg gccgctaaga acctgcagtc   1380

cgcggaagaa tggtacaagt ccaagtttgc caacctgaac gagcaggcgg cgcgcagcac   1440

cgaggccatc cgggccagcc gcgaggagat ccacgagtat cggcgccagc tgcaggcgcg   1500

caccatcgag atcgagggcc tgcgcggggc caacgagtcc ttggagaggc agatcctgga   1560

gctggaggag cggcacagtg ccgaggtagc tggctaccag gtaagggccg gggctgggcg   1620

tggggagggg tgccctgccc tcttccgcgc gtaccctctt cctctggtaa aactgggccc   1680

caggacttaa ggggagggca aaagagagga gagaagagcc gcggctggag gcgctggtta   1740

acaaaaaacc ctggagtctt taatgttaat tttagggaac gcccctcatt tatgtccctg   1800

ccccagccct tcaaac                                                   1816
```

<210> SEQ ID NO 74
<211> LENGTH: 1934
<212> TYPE: DNA
<213> ORGANISM: Homo sapiens

<400> SEQUENCE: 74

```
aaacaccggc agtcaacagg caggcaaaga acctgggggt gggggtagca gcggtcccac     60

cctcaaaagg cccgggctgc ccagaccaag agaaagcgat gaatctcttc tggtaacgtc    120

ccttcctgtc gcatggattc aaggccgacc tgccccagca ccaccaccag cagccttctg    180

ctggggccgg cacagctggg agcaacctcc tactctcagg cagacgcgca gcaccaagca    240

gagaggcccg gtgcaggatc ccagcgccga accagcgccg gctcagtgga cgcggaaggg    300

gccggcggcc gcggccggtc ccatccccca ctgcagaccc ccagcctgtg gcggtggtcc    360

agttccgcca ggaaaccgcc gcctggagct gtgggtcgcg cacattaacg catccagcgg    420

aaaaatgaag gagacccaaa ttcaaagtta aagtaatggt gacccgagag gtgccttgat    480

gagaaggttt ggggtcccgg ttactgatgg ttatcattct tacgagatgc tggtcaccta    540

cgaagggaga aaggcacgag gagcgcctga ccaaagtggt tttgccctgc ttcccgcaag    600

aggtggcacc cacggctgga acgcaggagt cagacccaca gtccccagct ctggacgccc    660

gcagcggggc ctcgaagagg ttcagggcgg tgcccgcggc gctcgggccg ggtctcccgg    720

ggcgtggggc ggggggcggg gttgggcggc ggccggggct cctccctctt ctgccccggg    780

ctcccctgct cttaacccgc gcgcgggggc gcccaggcca ctgggctccg cggagccagc    840

gagaggtctg cgcggagtct gagcggcgct cgtcccgtcc caaggccgac gccagcacgc    900

cgtcatggcc cccgcagcgg cgacgggggg cagcaccctg cccagtggct tctcggtctt    960

caccaccttg cccgacttgc tcttcatctt tgagtttgtg agtggctcct ggccggggaa   1020

gggacggggt gggctgagcc gtgcgctctc tcgggcgccc agcacagctg tcggacggga   1080

tccgctagct gcgcaggttc tgggagcatc ggggcagcag gcgcagggcg gggactaagc   1140

cagggaagtc ccctcccacc tccggtcctt tgtgcccttc tagaccaaca gaatgagggg   1200

aacagtctac aggactatgg aggaaaaact gggttcccaa ctggggtcag atgtaggcag   1260

cggggcaggg ggggacggct cttggttcgc tggtcccaaa gctgcgcgcg gggcccactt   1320

gacgcgcgca gcgccaccga agctcccgcc gcgctttgcg cggttgggta gaagtgcgca   1380
```

```
gcttttacaa gggagaaggt ttcgttaaaa aagaaaaaaa aatcagcaag agaaacatta    1440
gtattaccaa ccgagatttg gagatgagag ggagctgaat ccggtttatt ttcttctggc    1500
cttttaaagt ttctggcgag ggaacgtatt tgcgaccaat tcgatctgga aatgaggcca    1560
tcgtttgctt ggccgcagtc cttctgcccc gtgtgcgggg tgggggtgga ggagatgggg    1620
ggtggggggt ggggggtggc ggcgagagcg atccgcgcgc ctcgactgac cttgggcagg    1680
cccggggcct ctgcacctgc ggtcggtccc gccttgcacg cacggtctct gcctgaggct    1740
gcaggaaagc gcttcctact gagaactcct gataagcgct cacggtgtcg cgaagccgaa    1800
gtgacctccc tcagcctcaa ctccccgggg gccgctggcc ttcacctggg aggggtgtgc    1860
cctgtatgtc ctgtgggtgc ggtccgtcac cgcctgaggg acaccttttc cggcacccca    1920
ccctcagaag tgtc                                                      1934
```

```
<210> SEQ ID NO 75
<211> LENGTH: 2574
<212> TYPE: DNA
<213> ORGANISM: Homo sapiens

<400> SEQUENCE: 75

ctggagtggg acttcatctg ggaccaaagg agggctggtg aggggagtgg caggagggag      60
gagtgcctcg gggccccgag caggatgagc ctgaggaaga gacgggtccc catgttccct     120
ttcccgctca gataatggag gtgaattgag gggagcagag acctccccac cttcagggtg     180
ggaccctgag ggaccaggac acctttgcta ggggatgtcc ctcctcactc ctgcacaagt     240
tcctcaagga caccctcggg ctccgaaaac ggggggaggg ggacgacgcc ccagaggccc     300
ctgagcccct ggttcttccc gaccctaagg gcttttctcc ctcggttccc aggcggcgac     360
ggcgggtagc gcgaagcagc aggcgcaggg gcgctgggat ggggatgtct ctgcaggtct     420
aaggttcccc ttgggagtct aaacaaagac tacggcagcg ccgtcccctc ccccgggaac     480
ccgacgccgc gcggccacag ggggcctgga ggggcgggca gggcctcgca gcgcacccag     540
cacagtccgc gcggcggagc gggtgagaag tcggcggggg cgcggatcga ccggggtgtc     600
ccccaggctc cgcgtcgcgg tccccgctcg ccctcccgcc cgcccaccgg gcaccccagc     660
cgcgcagaag gcggaagcca cgcgcgaggg accgcggtcc gtccgggact agccccaggc     720
ccggcaccgc cccgcgggcc gagcgcccac acccgccaaa cccacgcggg cacgcccccg     780
cggcgcaccg cccccagccc ggcctccgcc cctgcagccg cgggcacgcg gaggggctcc     840
tggctgcccg cacctgcacc cgcgcgtcgg cggcgccgaa gccccgctcc ccgcctgcgc     900
gtctgtctcg tccgcatctc cgcggtgagt cggcggcgcc ctcgcccctg agcccagggc     960
cagcttctct cgccgccgcg gctgctgcgc gcgtccccgc ccagcccagc ccagccccga    1020
gcacgacccc agccccacgc acgaccctag ccccgcgagt cccgcaccga ctcgctcccg    1080
ccccatttcg cctccgcggg ggcggcgccc cctcctcccc gcggctcccg ctctccttcc    1140
tcgccttccc ggccgcgctg gggacccccca gccgccgtcc gcgacccccc accgcgacgc    1200
ccggaggcgg cggggtctct ttgttcgggc ggcgggcacg ggggaccacc tcccacggtg    1260
tcaccgcacc caccccgcgc ccttcctccg cctcctggag ttcaccggga ccaggtggcg    1320
gcgggtgcct ttttgggggt gcgcggccat gcaattggtg gatttttta aaccgttttg    1380
gagggggggag cgcggcgttg gggggcgggag agcgctcctg gctgtgagct gctcctgccg    1440
cttcgctccg cgctctcctg ccgctccgct ccgggtctcc cgcgctcctc tccccggctc    1500
ggccgagcgc gctgccccga cgccgccacc cagagccggg ccgcgccggg cgccgagatg    1560
```

```
aaggtgctgg gacaccggct ggagctgctc acaggtaccg cccgcctgcc ccgcagccgg   1620

ccgccacttt ccgagttgga gcggactccg ggcgcggcgg ccggggactg gggcggctcg   1680

ggtctgagca ggaaggggtg cggaccccaa ctaagtccta gttttgtgct acctgtttgt   1740

gtgcggagcc cagccccggg agaggacttg aggttgtggc gagtccctgg cgctggcgtc   1800

cgggctgcgg gagcaccggt caggggtgg ccccatgggg tctctgacca gcggagctcg   1860

gattaggacc ctgaaagcta gctcagggct cctgccctcc aatcagtgtc gcttgtcccc   1920

taagaaagga cccgtgggct tctggcagga cccgcgccat ggacctctta tttctgcgcc   1980

ctgtgacaat ctgagccgtc tttctctggg ggagaagttt cttgctggga gtggaggcga   2040

cgccaagtgg cctgggaagt gggaagccag attggaccct actgactggg gaccctcagc   2100

cttggggctc ctctggagaa gtgatcagtt gccctgctgg aaactcacat ccaggggggca   2160

gtggctggag agcaagagcg aacggtcagg aagaggaggt gggaaaggga gcagggacgg   2220

gggggaggat tcgaggagtg acttctgtgt tctccccggt gtggagagac ccagacagga   2280

ggaaaggaaa gcaacccggt ttcctccagc tctgggactt ataggtgctc catccgtgta   2340

tgtcagatga gcacagattc cagtaagtgt cctccgacac ctgggggagg gggctgatca   2400

ctgccttcca ggaccttaat gtccgatgag ggagcagagc cccggagccc tgttacaagg   2460

ctggaagggg cagccgtctg tgggtgcgct caggaaacgg tggaatccga gtcgggggca   2520

gcttttgaag acctcgaaaa acaatttttg ttaatgaaga aggaggtggc atta         2574
```

<210> SEQ ID NO 76
<211> LENGTH: 1393
<212> TYPE: DNA
<213> ORGANISM: Homo sapiens

<400> SEQUENCE: 76

```
ggggggtggg tgacatatct gcaggaaatg gaacgtggaa ggcactgtct gacttggctg     60

cattgcccgt gtggacccgg gcgctagtgc ctgcatgtcc ctctgaccgt gtgccctctg    120

gtgtgcgctt ggatggtgtc tgccttggtg atgcctgggg ccatcaggcc agggggcggg    180

ggtgtccttg gtgagccccc gaggctgtgt gcccagtgtg cgtgccgggt ctgtgcgtgc    240

aggggctgcc gtcccagtgg gcggccgtct agcttgtttg gatggctgcg ccagtgtgat    300

gggaaggaca ggcggcctct tccttaggag ccacctcaca gttcccaggg ctctgctgcg    360

ccagccgggc agaggcaagg aggtctgggc cacacaggaa tgacagcctt tcaggcaggg    420

gtccctgctg ggaggaacg aggaggggtt gcctgcctgc cttattttgt aggtggggga    480

aggcaacgct ggagccgtga agctggcagg gctaggggac cccaggtgga gcccagggca    540

cctcctctcg ccggggcatc aggtaccccg gccccattct tcctcaggag ggagaggcag    600

gggcagactc acccccaccc ccgggcccca cacgcctgcc ctgccggttc cgcagacgat    660

aggtcacccc gcacgcacgg aggtgacgac gtcagcacct gcccgcccat gcagaccctg    720

tcccctgaat tattgatgcg gctgacaggc cgaaccacag caccaccagc accaactccc    780

acaccggcgc aaagcccggc tcaaagcccc actcccctcc agtgctcaag gtcacaggcg    840

aggggagacg gaccgaccga gaggagccgc cacagccccc tcccctgctg ccgcagtgct    900

tcccgcctgc gcctacctgg aggcggggcc ggctctgacg tcacccagag ccaatgggag    960

tgctcggccc tgagggttgg gggcctcaga gtgcaccgcg ctgtggccct tgtggggctg   1020

cccttgcgca gcgctccaag ggacggggat gtttggcttc gatcaggctg aactgagtcc   1080
```

```
tgagctctcc gcagagggtg agagaaggcg ttagggaggt tcgcagcagg gttcagcgaa   1140

ggtcactgga cttcgtagga caggtagccc ggtgacgccc aggcccagcc ccagcccttc   1200

ccatcctggg agatgagccc tagtagagcc tgatcacgtc acctcagggg gatggggaca   1260

ggggcggcca caccagggct gggagaagac agtggggcct cctcagcagc agagagcaga   1320

cacccctcac acccctcagg cggacccgca cgctgcgggt ctgggtttgg aaggcaccgc   1380

cctgggctct cga                                                      1393
```

<210> SEQ ID NO 77
<211> LENGTH: 2295
<212> TYPE: DNA
<213> ORGANISM: Homo sapiens

<400> SEQUENCE: 77

```
ctccttcctt cacaccttcc ttcggaaacg tctgctcctg acaaggtcta cttcctgctc     60

tcaggaggcc cttattgtgg aggaagggag gcgtcgcccg tccctggctt ctctgacagc    120

cgtgttccat ccccgccctg tgccccttct cccggacagt gccttctcca gggctcaccc    180

aggagggtgc agcggtggcc cccggggcgg tggtcgtggt gggggtgtta gctgcagggg    240

tgccctcggt gggtgggagt tggtggcctc tcgctggtgc catgggactc gcatgttcgc    300

cctgcgcccc tcggctcttg agcccacagg ccgggatcct gcctgccagc cgcgtgcgct    360

gccgtttaac ccttgcaggc gcagagcgcg cggcggcggt gacagagaac tttgtttggc    420

tgcccaaata cagcctcctg cagaaggacc ctgcgcccgg ggaaggggag gaatctcttc    480

ccctctgggc gcccgccctc ctcgccatgg cccggcctcc acatccgccc acatctggcc    540

gcagcggggc gcccgggggg aggggctgag gccgcgtctc tcgccgtccc ctgggcgcgg    600

gccaggcggg gaggaggggg gcgctccggt cgtgtgccca ggactgtccc ccagcggcca    660

ctcgggcccc agccccccag gcctggcctt gacaggcggg cggagcagcc agtgcgagac    720

agggaggccg gtgcgggtgc gggaacctga tccgcccggg aggcgggggc ggggcggggg    780

cgcagcgcgc ggggaggggc cggcgcccgc cttcctcccc cattcattca gctgagccag    840

ggggcctagg ggctcctccg gcggctagct ctgcactgca ggagcgcggg cgcggcgccc    900

cagccagcgc gcagggcccg ggccccgccg ggggcgcttc ctcgccgctg ccctccgcgc    960

gacccgctgc ccaccagcca tcatgtcgga ccccgcggtc aacgcgcagc tggatgggat   1020

catttcggac ttcgaaggtg ggtgctgggc tggctgctgc ggccgcggac gtgctggaga   1080

ggaccctgcg ggtgggcctg gcgcgggacg ggggtgcgct gaggggagac gggagtgcgc   1140

tgaggggaga cgggacccct aatccaggcg ccctcccgct gagagcgccg cgcgcccccg   1200

gccccgtgcc cgcgccgcct acgtgggggga ccctgttagg ggcacccgcg tagaccctgc   1260

gcgccctcac aggaccctgt gctcgttctg cgcactgccg cctgggtttc cttcctttta   1320

ttgttgtttg tgtttgccaa gcgacagcga cctcctcgag ggctcgcgag gctgcctcgg   1380

aactctccag gacgcacagt ttcactctgg gaaatccatc ggtcccctcc ctttggctct   1440

ccccggcggc tctcgggccc cgcttggacc cggcaacggg atagggaggt cgttcctcac   1500

ctccgactga gtggacagcc gcgtcctgct cgggtggaca gccctcccct cccccacgcc   1560

agtttcgggg ccgccaagtt gtgcagcccg tgggccggga gcaccgaacg gacacagccc   1620

aggtcgtggc agggtctaga gtgggatgtc ccatggcccc catccaggcc tggggatatc   1680

ctcatccgcc tcccagaatc gggccgtggg ggacagaagg ggcctgcgtg cgggcaggga   1740

gagtattttg gctctctcct gtcttcgggg tttacaaagt gtgttgggac ttgcggggct   1800
```

```
gctctgtcca agcctgggtc tggcgtccgc gtctctgagc ctgtgagtgc gtgcgctttc   1860

ctgcgtcctc ttgactgccg gtgctggggc tctgcgtcct gcgtccgcgg gagtaaatac   1920

agcaggcgaa ggggaagctc acacaatggt ctccagcgct ctggggcagg gcttctgagg   1980

ggcgggcctg cctctgccgg gacctggagc cccgcccct cggagaggct cctaggctga   2040

cttgggcaga gccctctggt gggccgggag ggggaaaggc tgtgttgaaa tgagcaaact   2100

gtccaggtgt caggccaagc tgggaggtga ccagcctgag gtcctccccg ctccatggcc   2160

agaaccaggg ctgacatctg ggtgtcctga gcccagctgc ccacacggcc cacctggggt   2220

cagccctatc tgagtggggg aggcggggcc tcctggggga ccagaacttt ggctggacgc   2280

caagcagagt gccag                                                    2295
```

<210> SEQ ID NO 78
<211> LENGTH: 1098
<212> TYPE: DNA
<213> ORGANISM: Homo sapiens

<400> SEQUENCE: 78

```
agcaagcacc tggggtagag gggacaaacc caggtggctg tgttccagcc ctggctgcag     60

gtctgaatgg ctttctgggg tggctggcca tgctccctga gagcccagct gtggcgatgt    120

ctgagcaggt aggtggggga gcacctagga agcaggggtg tcaggcagag cacaaggaga    180

gagggtgtcc aggtcagttt caggacctgg ctgagaggag gggctcctc acgggcaccg    240

cctctggcaa gcacagggac aagggcaagg acggcatggc cagaggtccc tgggagcctc    300

ttcccctctc ttcttcctag cagctccccc tcactcttcc cagggaccct gtcactttcc    360

tttagcgtgt ggcagctcct tggcgtccct cccgtgcctt caggttgctt ctgcgccggg    420

cctgccgctg ggcgccccta tctctgcctg cccctcctc ctgctcccct cgccctgccc    480

ccttggagca attccccacc gagcctccct tcccaggcag tcgaggtccc tccctacctc    540

tgccccgcgc tctgggaggc tccttgttcc gcgaccacaa agcccctttg atcctctgct    600

cggctctgag ccatgtgacc cggtgggcgg gccgcggctc tcggcgcgtc cagcgcagcc    660

cgacgttccg ctgctggggt gagtcctgct cctttgttct tcccagcctt gcaccactgg    720

ctcgggggct ctcaggtggc gcggccgcga ggcggaccct gatggccatg gtggcggtgc    780

cgggagccac gctgtccctg ggccccggcc cgaggccggc aggaccgagc ggggtcccca    840

ggagaggggt ggcggggagc tcgatctcca cgcggggacc agattttcgg cctcaaaata    900

gaagaatagg gctttgtgtg gtcacagcta tctctttgta aatatttggc caactaagct    960

gagtggctaa gttctcctgc tgcccggagc ttcttggaac atgtttcctt ttcgcaaggg   1020

gtttccctgg cttccaggag ggccaggaag aaattcgaat tggccaccgc tttctctaaa   1080

atcactccgc tcaagtta                                                 1098
```

<210> SEQ ID NO 79
<211> LENGTH: 1404
<212> TYPE: DNA
<213> ORGANISM: Homo sapiens

<400> SEQUENCE: 79

```
agaagggaat atcagaagca ggacgaaagc caggtcaagt ctctttcctt aggctcccca     60

aagggacaag tactcacctc ccagagacct ggcccagcgg gtcctcatgg cagcaccacc    120

ccctcccggt gcccacgacc attcgtctcc catccggcgt tctccaggat ttccaaagac    180
```

```
gcccgtttag atccacaggt acttacctga gtccctctgc ttctccacaa ctccgactcc    240

tccccgcctc tctctttttt taaaaaaaaa atttaaacaa ttcccaaata atatttaata    300

ggaaagaaga aggaaaagga gcgcacagga agggcggagg cggcacccgg gggggactgt    360

ccccagagga ggccgctgtg agccggcgac gcgaggctgg gggagtggga ggcaaacccg    420

ctaacctgtc gtcgaatggc cactcccagt tctccgctca cgagggtgga aaggcagaag    480

gcttgaaggc aaggcgtgag ggagcgccca ggacgctctc ggaggggccg ggccggggtc    540

tgcgctgcag cccgcacgca cctcacttcc gcgtcgcggc gctcggtcgc tcgcccccctc    600

tcttgggccc cttctggtcg tcgccgtcct cctcctccta gtcctcctcc ttctccttct    660

cctcggctct ccgcccccac cgctgatttg tcagcgcttc tgcccgcccc tctcccggcg    720

ctcgctgctt tccctgcagc gtgctcctcg tccctatctc ggatggggat ggggcagggg    780

gcgcggggtg agccatcaac tccagccgcc tgcctggccg cgcaaggcgg gaaagtgggg    840

gcgcttttgc gcctcacgtt aagtttaggg tcacgagcac tcttgtggag atcgggagcg    900

gttgggctag ggatgatgcc tcttcctctt tccccttccc ctcccttctt gtccccgcct    960

ttcctctggg tcctcccggg gaccaccccc taccccctcgt cagagtcgcc ctgggagagc   1020

cgagggcctg agggtcgacc accaagggca gagcctatcc cttggggagc tgctggagga   1080

gacaggcagc gccgggaggt ggctcacacc gcaccgccga gagcgctttg ccctcgcatc   1140

gctgaaattt aatcacggtc acaggttaca acgttagggg tcgctttagt tcaaatatct   1200

tcaaggtttt cgtttgctct taatctagga agagccggaa agggtcctga gggtgaaagg   1260

gagactacta aggaagagtc acaggttgag gaggcaggag aaggctcagc aaatcctctt   1320

tccacgccac tatcaccatt ttcctttcca ccaatcagcg cctgccagac gctgattttc   1380

ccatcagtgg aacaaggaat aaat                                          1404
```

<210> SEQ ID NO 80
<211> LENGTH: 1756
<212> TYPE: DNA
<213> ORGANISM: Homo sapiens

<400> SEQUENCE: 80

```
caaaggctgt aacaacctgg aacgcaaatt cgttaaatta tgatacaata aggccaacct     60

cgaggatcct cggtggacta ctagcgcact tccttacaat tagaaagtga aaaactgggt    120

cagccctaga gtcacgcaat aatgctgcgt cacgaaactg cgcattccaa gagaaacttt    180

tctcaggccc agaattaagt cggagggatc cgccgcgcag ctcaatccct aggaagcatg    240

aaagaatgta ttgtaaagag taaaatcacg cgcaatccat cccaatataa ccgcagttgt    300

tcgtgggcct tcttgcagag aaaggctgcc caaccttgac ggggccatgg gcgctgcggg    360

agggcaaaag accacagaga tctgcgaagc caaagtaaac aacggggttg gggcggcgag    420

aatgatcaat agcgatgctc cgaaaggact ccgcgatagg aatcgagcgg gaaggattcc    480

ctccatccta acagtccatg ggttaagagg ccgaagcttc cctaaatacc acactcccgc    540

gagagaaggg actgagaaca acttctcaaa ctattctctc tcgaaatcgc tcccttcctc    600

gaaaattcca tctctgagac tcggatgagg tccccacccc ctccaccctt gtcccgtgac    660

cgtcgcccgc tcagcctccc agccgagtcc gcggggcctg gggcgcccac cccgcccacc    720

caagggaccg cgcaggggtg aactcccccg cgcccccacct gcgccttcca gacctcgggc    780

gccccggcgt tgcctcgaga gctccctgcg cggccgccgc ggcacggacc agctcccact    840

cccttacact gggcgccgct gcgctcgccg gggccggtc ccgaggttcc caaggcctcg     900
```

cgcgcgcgct tgccgtggca accaagacgt tccacgacgc gcgctctcga acgcttcgcg 960
tcacgcggcc gcgcggcccc gcccgtcggc ctcgctcccg ccacagagcc cgcagcacgc 1020
cgccgccgca gcctaggtca cgtgagtacc cacgcgcgcg tcttgccagc ggattcatca 1080
ccggcctgct cagactaggt tctgcccact ctgaccttct aaatggtacg tgggaggacg 1140
tccgtcccct tcggacccaa gagtcaccgt aacactctag aaggggagaa aaggagcgag 1200
ggcggcaggc gacagagaac ctcgcgagtc agcggccccg cgcagacccc cccaggcacg 1260
gtcccctgcg gccacgtcgg ctgctcggcg cctgcgcaat ctctttctct ccagcgaaac 1320
cgaggcctcc ggagagccta gtagagagtg tgggcagtga gcgcttgtag ccgctagagg 1380
gagcgctggg cacagtgcac gagagacaat aaaggctgat tatcccctca atgtctctgc 1440
agcctgagct ttgtgacttc tgtatccaga gcacagttaa tttccaaaag cccgcctgca 1500
ccacgtgttt taagtcttgg tgtgtgtgta aagtctatat cactatcata aaactgttag 1560
ttcctgattc cgggatacaa agagtaaaat caagatgaac atactttacc cttcttgaca 1620
agtgttttta aattagtaaa atattgtaga tgacagactc ttcaataggg ctgccttagg 1680
gaaaaaaaaa cagaaaaaag aaaaagcagt atgtacttgc ccggagcatt tagaaccagt 1740
tttgttgttg ttgtgt 1756

<210> SEQ ID NO 81
<211> LENGTH: 24
<212> TYPE: RNA
<213> ORGANISM: Artificial
<220> FEATURE:
<223> OTHER INFORMATION: Target specific sequence of the Cpf1-C9orf72-crRNA#1

<400> SEQUENCE: 81
ccguaagaca cuguuaagug cauu 24

<210> SEQ ID NO 82
<211> LENGTH: 24
<212> TYPE: RNA
<213> ORGANISM: Artificial
<220> FEATURE:
<223> OTHER INFORMATION: Target specific sequence of the Cpf1-C9orf72-crRNA#2

<400> SEQUENCE: 82
uauucagaaa caggagggag gucc 24

<210> SEQ ID NO 83
<211> LENGTH: 24
<212> TYPE: RNA
<213> ORGANISM: Artificial
<220> FEATURE:
<223> OTHER INFORMATION: Target specific sequence of the Cpf1-CNRIP1-crRNA#1

<400> SEQUENCE: 83
gcuuguauuc cuccauucuc gcuu 24

<210> SEQ ID NO 84
<211> LENGTH: 24
<212> TYPE: RNA
<213> ORGANISM: Artificial
<220> FEATURE:
<223> OTHER INFORMATION: Target specific sequence of the Cpf1-CNRIP1-crRNA#2

<400> SEQUENCE: 84
cacagauuuu gaagggugag cuau 24

<210> SEQ ID NO 85
<211> LENGTH: 24
<212> TYPE: RNA
<213> ORGANISM: Artificial
<220> FEATURE:
<223> OTHER INFORMATION: Target specific sequence of the Cpf1-DMPK-crRNA#1

<400> SEQUENCE: 85
uugugcauga cgcccugcuc uggg 24

<210> SEQ ID NO 86
<211> LENGTH: 24
<212> TYPE: RNA
<213> ORGANISM: Artificial
<220> FEATURE:
<223> OTHER INFORMATION: Target specific sequence of the Cpf1-DMPK-crRNA#2

<400> SEQUENCE: 86
cugcuggccu cuccagccuu cuca 24

<210> SEQ ID NO 87
<211> LENGTH: 24
<212> TYPE: RNA
<213> ORGANISM: Artificial
<220> FEATURE:
<223> OTHER INFORMATION: Target specific sequence of the Cpf1-EGFR-crRNA#1

<400> SEQUENCE: 87
gagaggcuaa gugucccacu gccc 24

<210> SEQ ID NO 88
<211> LENGTH: 24
<212> TYPE: RNA
<213> ORGANISM: Artificial
<220> FEATURE:
<223> OTHER INFORMATION: Target specific sequence of the Cpf1-EGFR-crRNA#2

<400> SEQUENCE: 88
agccaaccaa aauauuaaac cugu 24

<210> SEQ ID NO 89
<211> LENGTH: 24
<212> TYPE: RNA
<213> ORGANISM: Artificial
<220> FEATURE:
<223> OTHER INFORMATION: Target specific sequence of the Cpf1-FBN1-crRNA#1

<400> SEQUENCE: 89
ugccccaaag gagaggacgu gguu 24

<210> SEQ ID NO 90
<211> LENGTH: 24
<212> TYPE: RNA
<213> ORGANISM: Artificial
<220> FEATURE:
<223> OTHER INFORMATION: Target specific sequence of the Cpf1-FBN1-crRNA#2

<400> SEQUENCE: 90
guggcuuuga aagguauagu auuu 24

<210> SEQ ID NO 91
<211> LENGTH: 24
<212> TYPE: RNA
<213> ORGANISM: Artificial
<220> FEATURE:
<223> OTHER INFORMATION: Target specific sequence of the Cpf1-HTT-crRNA#1

<400> SEQUENCE: 91
ugggagugca ccccugcucu gacc 24

<210> SEQ ID NO 92
<211> LENGTH: 24
<212> TYPE: RNA
<213> ORGANISM: Artificial
<220> FEATURE:
<223> OTHER INFORMATION: Target specific sequence of the Cpf1-HTT-crRNA#2

<400> SEQUENCE: 92
ggcccgcugc agcucccugu cccg 24

<210> SEQ ID NO 93
<211> LENGTH: 24
<212> TYPE: RNA
<213> ORGANISM: Artificial
<220> FEATURE:
<223> OTHER INFORMATION: Target specific sequence of the Cpf1-INA-crRNA#1

<400> SEQUENCE: 93
caguuacagu gaggaccugc agag 24

<210> SEQ ID NO 94
<211> LENGTH: 24
<212> TYPE: RNA
<213> ORGANISM: Artificial
<220> FEATURE:
<223> OTHER INFORMATION: Target specific sequence of the Cpf1-INA-crRNA#2

<400> SEQUENCE: 94
ugucccugcc ccagcccuuc aaac 24

<210> SEQ ID NO 95
<211> LENGTH: 24
<212> TYPE: RNA
<213> ORGANISM: Artificial
<220> FEATURE:
<223> OTHER INFORMATION: Target specific sequence of the Cpf1-MAL-crRNA#1

<400> SEQUENCE: 95
ccugccuguu gacugccggu guuu 24

<210> SEQ ID NO 96
<211> LENGTH: 24
<212> TYPE: RNA
<213> ORGANISM: Artificial
<220> FEATURE:
<223> OTHER INFORMATION: Target specific sequence of the Cpf1-MAL-crRNA#2

<400> SEQUENCE: 96
cggcacccca cccucagaag uguc 24

<210> SEQ ID NO 97
<211> LENGTH: 24
<212> TYPE: RNA
<213> ORGANISM: Artificial
<220> FEATURE:
<223> OTHER INFORMATION: Target specific sequence of the Cpf1-NDRG4.1-crRNA#1

<400> SEQUENCE: 97
gucccagaug aagucccacu ccag 24

<210> SEQ ID NO 98
<211> LENGTH: 24
<212> TYPE: RNA
<213> ORGANISM: Artificial
<220> FEATURE:
<223> OTHER INFORMATION: Target specific sequence of the Cpf1-NDRG4.1-crRNA#2

<400> SEQUENCE: 98
uuaaugaaga aggagguggc auua 24

<210> SEQ ID NO 99
<211> LENGTH: 24
<212> TYPE: RNA
<213> ORGANISM: Artificial
<220> FEATURE:
<223> OTHER INFORMATION: Target specific sequence of the Cpf1-NDRG4.2-crRNA#1

<400> SEQUENCE: 99
cugcagauau gucacccacc cccc 24

<210> SEQ ID NO 100
<211> LENGTH: 24
<212> TYPE: RNA
<213> ORGANISM: Artificial
<220> FEATURE:
<223> OTHER INFORMATION: Target specific sequence of the Cpf1-NDRG4.2-crRNA#2

<400> SEQUENCE: 100
gaaggcaccg cccugggcuc ucga 24

<210> SEQ ID NO 101
<211> LENGTH: 24
<212> TYPE: RNA
<213> ORGANISM: Artificial
<220> FEATURE:
<223> OTHER INFORMATION: Target specific sequence of the Cpf1-SEPT9.1-crRNA#1

<400> SEQUENCE: 101
cgaaggaagg ugugaaggaa ggag 24

<210> SEQ ID NO 102
<211> LENGTH: 24
<212> TYPE: RNA
<213> ORGANISM: Artificial
<220> FEATURE:
<223> OTHER INFORMATION: Target specific sequence of the Cpf1-SEPT9.1-crRNA#2

<400> SEQUENCE: 102
gcuggacgcc aagcagagug ccag 24

<210> SEQ ID NO 103
<211> LENGTH: 24
<212> TYPE: RNA
<213> ORGANISM: Artificial
<220> FEATURE:
<223> OTHER INFORMATION: Target specific sequence of the Cpf1-SEPT9.2-crRNA#1

<400> SEQUENCE: 103
uccccucuac cccaggugcu ugcu 24

<210> SEQ ID NO 104
<211> LENGTH: 24
<212> TYPE: RNA
<213> ORGANISM: Artificial
<220> FEATURE:
<223> OTHER INFORMATION: Target specific sequence of the Cpf1-SEPT9.2-crRNA#2

<400> SEQUENCE: 104
ucuaaaauca cuccgcucaa guua 24

<210> SEQ ID NO 105
<211> LENGTH: 24
<212> TYPE: RNA
<213> ORGANISM: Artificial
<220> FEATURE:
<223> OTHER INFORMATION: Target specific sequence of the Cpf1-SNCA-crRNA#1

<400> SEQUENCE: 105
guccugcuuc ugauauuccc uucu 24

<210> SEQ ID NO 106
<211> LENGTH: 24
<212> TYPE: RNA
<213> ORGANISM: Artificial
<220> FEATURE:
<223> OTHER INFORMATION: Target specific sequence of the Cpf1-SNCA-crRNA#2

<400> SEQUENCE: 106
ccaucagugg aacaaggaau aaau 24

<210> SEQ ID NO 107
<211> LENGTH: 24
<212> TYPE: RNA
<213> ORGANISM: Artificial
<220> FEATURE:
<223> OTHER INFORMATION: Target specific sequence of the Cpf1-SPG20-crRNA#1

<400> SEQUENCE: 107
cguuccaggu uguuacagcc uuug 24

<210> SEQ ID NO 108
<211> LENGTH: 24
<212> TYPE: RNA
<213> ORGANISM: Artificial
<220> FEATURE:
<223> OTHER INFORMATION: Target specific sequence of the Cpf1-SPG20-crRNA#2

<400> SEQUENCE: 108
gaaccaguuu uguuguuguu gugu 24

<210> SEQ ID NO 109
<211> LENGTH: 20
<212> TYPE: DNA
<213> ORGANISM: Artificial
<220> FEATURE:
<223> OTHER INFORMATION: Oligonucleotide

<400> SEQUENCE: 109
gctgtgggga tgttgctaat 20

<210> SEQ ID NO 110
<211> LENGTH: 20
<212> TYPE: DNA
<213> ORGANISM: Artificial
<220> FEATURE:
<223> OTHER INFORMATION: Oligonucleotide

<400> SEQUENCE: 110
acttcatttc ccaggtgtgc 20

<210> SEQ ID NO 111
<211> LENGTH: 20
<212> TYPE: DNA
<213> ORGANISM: Artificial
<220> FEATURE:
<223> OTHER INFORMATION: Oligonucleotide

<400> SEQUENCE: 111
ctgatgggcg tgctactttt 20

<210> SEQ ID NO 112
<211> LENGTH: 20
<212> TYPE: DNA
<213> ORGANISM: Artificial
<220> FEATURE:
<223> OTHER INFORMATION: Oligonucleotide

<400> SEQUENCE: 112
agctgagaga agcgttctgg 20

<210> SEQ ID NO 113
<211> LENGTH: 20
<212> TYPE: DNA
<213> ORGANISM: Artificial
<220> FEATURE:
<223> OTHER INFORMATION: Oligonucleotide

<400> SEQUENCE: 113
ggacaggctc tgagacaagg 20

<210> SEQ ID NO 114
<211> LENGTH: 20
<212> TYPE: DNA
<213> ORGANISM: Artificial
<220> FEATURE:
<223> OTHER INFORMATION: Oligonucleotide

<400> SEQUENCE: 114
agccctcttc cctctcagac 20

<210> SEQ ID NO 115
<211> LENGTH: 20
<212> TYPE: DNA
<213> ORGANISM: Artificial
<220> FEATURE:
<223> OTHER INFORMATION: Oligonucleotide

<400> SEQUENCE: 115
catggaagct ggaggcttag 20

<210> SEQ ID NO 116
<211> LENGTH: 20
<212> TYPE: DNA
<213> ORGANISM: Artificial
<220> FEATURE:
<223> OTHER INFORMATION: Oligonucleotide

<400> SEQUENCE: 116
tccaaagggc agaccaatag 20

<210> SEQ ID NO 117
<211> LENGTH: 20
<212> TYPE: DNA
<213> ORGANISM: Artificial
<220> FEATURE:
<223> OTHER INFORMATION: Oligonucleotide

<400> SEQUENCE: 117 cccttcaga gacagcaaag 20

<210> SEQ ID NO 118
<211> LENGTH: 20
<212> TYPE: DNA
<213> ORGANISM: Artificial
<220> FEATURE:
<223> OTHER INFORMATION: Oligonucleotide

<400> SEQUENCE: 118
gcccaacaga tcacatgaag 20

<210> SEQ ID NO 119
<211> LENGTH: 20
<212> TYPE: DNA
<213> ORGANISM: Artificial
<220> FEATURE:
<223> OTHER INFORMATION: Oligonucleotide

<400> SEQUENCE: 119
cttgcagatc aaaaggcaca 20

<210> SEQ ID NO 120
<211> LENGTH: 20
<212> TYPE: DNA
<213> ORGANISM: Artificial
<220> FEATURE:
<223> OTHER INFORMATION: Oligonucleotide

<400> SEQUENCE: 120
atagaacccg agggcagact 20

<210> SEQ ID NO 121
<211> LENGTH: 20
<212> TYPE: DNA
<213> ORGANISM: Artificial
<220> FEATURE:
<223> OTHER INFORMATION: Oligonucleotide

<400> SEQUENCE: 121
acagggagtg gctctctgaa 20

<210> SEQ ID NO 122

<211> LENGTH: 20
<212> TYPE: DNA
<213> ORGANISM: Artificial
<220> FEATURE:
<223> OTHER INFORMATION: Oligonucleotide

<400> SEQUENCE: 122
acctttcacg ttttgccaac 20

<210> SEQ ID NO 123
<211> LENGTH: 20
<212> TYPE: DNA
<213> ORGANISM: Artificial
<220> FEATURE:
<223> OTHER INFORMATION: Oligonucleotide

<400> SEQUENCE: 123
atcctcagcg gtctcagaaa 20

<210> SEQ ID NO 124
<211> LENGTH: 20
<212> TYPE: DNA
<213> ORGANISM: Artificial
<220> FEATURE:
<223> OTHER INFORMATION: Oligonucleotide

<400> SEQUENCE: 124
ggttttgctt tttgggatga 20

<210> SEQ ID NO 125
<211> LENGTH: 20
<212> TYPE: DNA
<213> ORGANISM: Artificial
<220> FEATURE:
<223> OTHER INFORMATION: Oligonucleotide

<400> SEQUENCE: 125
ccctgttctg cttccaatgt 20

<210> SEQ ID NO 126
<211> LENGTH: 20
<212> TYPE: DNA
<213> ORGANISM: Artificial
<220> FEATURE:
<223> OTHER INFORMATION: Oligonucleotide

<400> SEQUENCE: 126
gaccttttgc aggtgagacc 20

<210> SEQ ID NO 127
<211> LENGTH: 20
<212> TYPE: DNA
<213> ORGANISM: Artificial
<220> FEATURE:
<223> OTHER INFORMATION: Oligonucleotide

<400> SEQUENCE: 127
cagctggtgg atcggttaat 20

<210> SEQ ID NO 128
<211> LENGTH: 20
<212> TYPE: DNA
<213> ORGANISM: Artificial
<220> FEATURE:
<223> OTHER INFORMATION: Oligonucleotide

<400> SEQUENCE: 128
cctcacaaag tgctgggatt 20

<210> SEQ ID NO 129
<211> LENGTH: 20
<212> TYPE: DNA
<213> ORGANISM: Artificial
<220> FEATURE:
<223> OTHER INFORMATION: Oligonucleotide

<400> SEQUENCE: 129
atcacagagc cgaccatctc 20

<210> SEQ ID NO 130
<211> LENGTH: 20
<212> TYPE: DNA
<213> ORGANISM: Artificial
<220> FEATURE:
<223> OTHER INFORMATION: Oligonucleotide

<400> SEQUENCE: 130
ccagcattag tgggtctggt 20

<210> SEQ ID NO 131
<211> LENGTH: 20
<212> TYPE: DNA
<213> ORGANISM: Artificial
<220> FEATURE:
<223> OTHER INFORMATION: Oligonucleotide

<400> SEQUENCE: 131
agtctcagca ctcctgcaca 20

<210> SEQ ID NO 132
<211> LENGTH: 20
<212> TYPE: DNA
<213> ORGANISM: Artificial
<220> FEATURE:
<223> OTHER INFORMATION: Oligonucleotide

<400> SEQUENCE: 132
gtcacattca ctcggggact 20

<210> SEQ ID NO 133
<211> LENGTH: 20
<212> TYPE: DNA
<213> ORGANISM: Artificial
<220> FEATURE:
<223> OTHER INFORMATION: Oligonucleotide

<400> SEQUENCE: 133
agaggtcgtg gcactgagat 20

<210> SEQ ID NO 134
<211> LENGTH: 20
<212> TYPE: DNA
<213> ORGANISM: Artificial
<220> FEATURE:
<223> OTHER INFORMATION: Oligonucleotide

<400> SEQUENCE: 134
gccttttctc gcttcctcct 20

<210> SEQ ID NO 135
<211> LENGTH: 20
<212> TYPE: DNA

<213> ORGANISM: Artificial
<220> FEATURE:
<223> OTHER INFORMATION: Oligonucleotide

<400> SEQUENCE: 135
gctagctcct cccagacctt 20

<210> SEQ ID NO 136
<211> LENGTH: 20
<212> TYPE: DNA
<213> ORGANISM: Artificial
<220> FEATURE:
<223> OTHER INFORMATION: Oligonucleotide

<400> SEQUENCE: 136
attctgtctc cctccccact 20

<210> SEQ ID NO 137
<211> LENGTH: 20
<212> TYPE: RNA
<213> ORGANISM: Artificial
<220> FEATURE:
<223> OTHER INFORMATION: Target specific sequence of the Cas9-CNRIP1-crRNA#1

<400> SEQUENCE: 137
cuccaacccc cgggcccgcu 20

<210> SEQ ID NO 138
<211> LENGTH: 20
<212> TYPE: RNA
<213> ORGANISM: Artificial
<220> FEATURE:
<223> OTHER INFORMATION: Target specific sequence of the Cas9-CNRIP1-crRNA#2

<400> SEQUENCE: 138
ccucugccug uaccccaugg 20

<210> SEQ ID NO 139
<211> LENGTH: 20
<212> TYPE: RNA
<213> ORGANISM: Artificial
<220> FEATURE:
<223> OTHER INFORMATION: Target specific sequence of the Cas9-CNRIP1-crRNA#3

<400> SEQUENCE: 139
ugggacgagc auacguauaa 20

<210> SEQ ID NO 140
<211> LENGTH: 20
<212> TYPE: RNA
<213> ORGANISM: Artificial
<220> FEATURE:
<223> OTHER INFORMATION: Target specific sequence of the Cas9-CNRIP1-crRNA#4

<400> SEQUENCE: 140
aaauuuaaau caccggcuag 20

<210> SEQ ID NO 141
<211> LENGTH: 20
<212> TYPE: RNA
<213> ORGANISM: Artificial
<220> FEATURE:
<223> OTHER INFORMATION: Target specific sequence of the Cas9-MALcrRNA#1

<400> SEQUENCE: 141
gggagcaacc uccuacucuc 20

<210> SEQ ID NO 142
<211> LENGTH: 20
<212> TYPE: RNA
<213> ORGANISM: Artificial
<220> FEATURE:
<223> OTHER INFORMATION: Target specific sequence of the Cas9-MAL-crRNA#2

<400> SEQUENCE: 142
cugcuggggc cggcacagcu 20

<210> SEQ ID NO 143
<211> LENGTH: 20
<212> TYPE: RNA
<213> ORGANISM: Artificial
<220> FEATURE:
<223> OTHER INFORMATION: Target specific sequence of the Cas9-MAL-crRNA#3

<400> SEQUENCE: 143
cagcggcccc cggggaguug 20

<210> SEQ ID NO 144
<211> LENGTH: 20
<212> TYPE: RNA
<213> ORGANISM: Artificial
<220> FEATURE:
<223> OTHER INFORMATION: Target specific sequence of the Cas9-MAL-crRNA#4

<400> SEQUENCE: 144
cgacaccgug agcgcuuauc 20

<210> SEQ ID NO 145
<211> LENGTH: 20
<212> TYPE: RNA
<213> ORGANISM: Artificial
<220> FEATURE:
<223> OTHER INFORMATION: Target specific sequence of the Cas9-HTT-crRNA#1

<400> SEQUENCE: 145
gcgcugcgcu gggaccgaug 20

<210> SEQ ID NO 146
<211> LENGTH: 20
<212> TYPE: RNA
<213> ORGANISM: Artificial
<220> FEATURE:
<223> OTHER INFORMATION: Target specific sequence of the Cas9-HTT-crRNA#2

<400> SEQUENCE: 146
acuaaucaca gugccucugu 20

<210> SEQ ID NO 147
<211> LENGTH: 20
<212> TYPE: RNA
<213> ORGANISM: Artificial
<220> FEATURE:
<223> OTHER INFORMATION: Target specific sequence of the Cas9-HTT-crRNA#3

<400> SEQUENCE: 147
agcagcggcu gugccugcgg 20

<210> SEQ ID NO 148
<211> LENGTH: 20
<212> TYPE: RNA
<213> ORGANISM: Artificial
<220> FEATURE:
<223> OTHER INFORMATION: Target specific sequence of the Cas9-HTT-crRNA#4

<400> SEQUENCE: 148
acagccgggc cggguggcgg 20

<210> SEQ ID NO 149
<211> LENGTH: 20
<212> TYPE: RNA
<213> ORGANISM: Artificial
<220> FEATURE:
<223> OTHER INFORMATION: Target specific sequence of the Cas9-SNCA-crRNA#1

<400> SEQUENCE: 149
agacgcccgu uuagauccac 20

<210> SEQ ID NO 150
<211> LENGTH: 20
<212> TYPE: RNA
<213> ORGANISM: Artificial
<220> FEATURE:
<223> OTHER INFORMATION: Target specific sequence of the Cas9-SNCA-crRNA#2

<400> SEQUENCE: 150
ccuggcccag cggguccuca 20

<210> SEQ ID NO 151
<211> LENGTH: 20
<212> TYPE: RNA
<213> ORGANISM: Artificial
<220> FEATURE:
<223> OTHER INFORMATION: Target specific sequence of the Cas9-SNCA-crRNA#3

<400> SEQUENCE: 151
ggugauagug gcguggaaag 20

<210> SEQ ID NO 152
<211> LENGTH: 20
<212> TYPE: RNA
<213> ORGANISM: Artificial
<220> FEATURE:
<223> OTHER INFORMATION: Target specific sequence of the Cas9-SNCA-crRNA#4

<400> SEQUENCE: 152
uucacccuca ggacccuuuc 20

<210> SEQ ID NO 153
<211> LENGTH: 20
<212> TYPE: RNA
<213> ORGANISM: Artificial
<220> FEATURE:
<223> OTHER INFORMATION: Target specific sequence of the Cas9-EGFR-crRNA#1

<400> SEQUENCE: 153
cugucucugc acccggaguu 20

<210> SEQ ID NO 154
<211> LENGTH: 20
<212> TYPE: RNA
<213> ORGANISM: Artificial
<220> FEATURE:
<223> OTHER INFORMATION: Target specific sequence of the Cas9-EGFR-crRNA#2

<400> SEQUENCE: 154
cauuggcuuc aaaguaccca 20

<210> SEQ ID NO 155
<211> LENGTH: 20
<212> TYPE: RNA
<213> ORGANISM: Artificial
<220> FEATURE:
<223> OTHER INFORMATION: Target specific sequence of the Cas9-EGFR-crRNA#3

<400> SEQUENCE: 155
agccccauuu ugaaacacca 20

<210> SEQ ID NO 156
<211> LENGTH: 20
<212> TYPE: RNA
<213> ORGANISM: Artificial
<220> FEATURE:
<223> OTHER INFORMATION: Target specific sequence of the Cas9-EGFR-crRNA#4

<400> SEQUENCE: 156
caggaugagc ucugcuuccg 20

<210> SEQ ID NO 157
<211> LENGTH: 20
<212> TYPE: RNA
<213> ORGANISM: Artificial
<220> FEATURE:
<223> OTHER INFORMATION: Target specific sequence of the Cas9-C9orf72-crRNA#1

<400> SEQUENCE: 157
gcgccaacgc uccuccagag 20

<210> SEQ ID NO 158
<211> LENGTH: 20
<212> TYPE: RNA
<213> ORGANISM: Artificial
<220> FEATURE:
<223> OTHER INFORMATION: Target specific sequence of the Cas9-C9orf72-crRNA#2

<400> SEQUENCE: 158
uccagcagcc uccccuauua 20

<210> SEQ ID NO 159
<211> LENGTH: 20
<212> TYPE: RNA
<213> ORGANISM: Artificial
<220> FEATURE:
<223> OTHER INFORMATION: Target specific sequence of the Cas9-C9orf72-crRNA#3

<400> SEQUENCE: 159
cucggagcug ugaagcaacc 20

<210> SEQ ID NO 160
<211> LENGTH: 20
<212> TYPE: RNA
<213> ORGANISM: Artificial
<220> FEATURE:
<223> OTHER INFORMATION: Target specific sequence of the Cas9-C9orf72-crRNA#4

<400> SEQUENCE: 160
aggucauguc ccacagaaug 20

<210> SEQ ID NO 161
<211> LENGTH: 20
<212> TYPE: RNA
<213> ORGANISM: Artificial
<220> FEATURE:
<223> OTHER INFORMATION: Target specific sequence of the Cas9-INA-crRNA#1

<400> SEQUENCE: 161
gccucaccuc aggaugaggg 20

<210> SEQ ID NO 162
<211> LENGTH: 20
<212> TYPE: RNA
<213> ORGANISM: Artificial
<220> FEATURE:
<223> OTHER INFORMATION: Target specific sequence of the Cas9-INA-crRNA#2

<400> SEQUENCE: 162
agaagagggg auagggucaa 20

<210> SEQ ID NO 163
<211> LENGTH: 20
<212> TYPE: RNA
<213> ORGANISM: Artificial
<220> FEATURE:
<223> OTHER INFORMATION: Target specific sequence of the Cas9-INA-crRNA#3

<400> SEQUENCE: 163
cuggggccca guuuuaccag 20

<210> SEQ ID NO 164
<211> LENGTH: 20
<212> TYPE: RNA
<213> ORGANISM: Artificial
<220> FEATURE:
<223> OTHER INFORMATION: Target specific sequence of the Cas9-INA-crRNA#4

<400> SEQUENCE: 164
uuaaccagcg ccuccagccg 20

<210> SEQ ID NO 165
<211> LENGTH: 20
<212> TYPE: RNA
<213> ORGANISM: Artificial
<220> FEATURE:
<223> OTHER INFORMATION: Target specific sequence of the Cas9-SPG20-crRNA#1

<400> SEQUENCE: 165
caauuagaaa gugaaaaacu 20

<210> SEQ ID NO 166
<211> LENGTH: 20
<212> TYPE: RNA
<213> ORGANISM: Artificial
<220> FEATURE:
<223> OTHER INFORMATION: Target specific sequence of the Cas9-SPG20-crRNA#2

<400> SEQUENCE: 166
acaauuagaa agugaaaaac 20

<210> SEQ ID NO 167
<211> LENGTH: 20
<212> TYPE: RNA
<213> ORGANISM: Artificial
<220> FEATURE:
<223> OTHER INFORMATION: Target specific sequence of the Cas9-SPG20-crRNA#3

<400> SEQUENCE: 167
acaccaagac uuaaaacacg 20

<210> SEQ ID NO 168
<211> LENGTH: 20
<212> TYPE: RNA
<213> ORGANISM: Artificial
<220> FEATURE:
<223> OTHER INFORMATION: Target specific sequence of the Cas9-SPG20-crRNA#4

<400> SEQUENCE: 168
caggcugcag agacauugag 20

<210> SEQ ID NO 169
<211> LENGTH: 20
<212> TYPE: RNA
<213> ORGANISM: Artificial
<220> FEATURE:
<223> OTHER INFORMATION: Target specific sequence of the Cas9-FBN1-crRNA#1

<400> SEQUENCE: 169
acuugggaga cccacaccaa 20

<210> SEQ ID NO 170
<211> LENGTH: 20
<212> TYPE: RNA
<213> ORGANISM: Artificial
<220> FEATURE:
<223> OTHER INFORMATION: Target specific sequence of the Cas9-FBN1-crRNA#2

<400> SEQUENCE: 170
uaguuuaacc acgaacgggg 20

<210> SEQ ID NO 171
<211> LENGTH: 20
<212> TYPE: RNA
<213> ORGANISM: Artificial
<220> FEATURE:
<223> OTHER INFORMATION: Target specific sequence of the Cas9-FBN1-crRNA#3

<400> SEQUENCE: 171
ccgacuuaga gagagcaccc 20

<210> SEQ ID NO 172
<211> LENGTH: 20
<212> TYPE: RNA
<213> ORGANISM: Artificial
<220> FEATURE:
<223> OTHER INFORMATION: Target specific sequence of the Cas9-FBN1-crRNA#4

<400> SEQUENCE: 172
augaacccca gucuuaaucu 20

<210> SEQ ID NO 173
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#1

<400> SEQUENCE: 173
agaccucccc accuucaggg 20

<210> SEQ ID NO 174
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#2

<400> SEQUENCE: 174
cuuucccgcu cagauaaugg 20

<210> SEQ ID NO 175
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#3

<400> SEQUENCE: 175
gcaacugauc acuucuccag 20

<210> SEQ ID NO 176
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#4

<400> SEQUENCE: 176
cccccucccc caggugucgg 20

<210> SEQ ID NO 177
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#1

<400> SEQUENCE: 177
ccugcugggg aggaacgagg 20

<210> SEQ ID NO 178
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#2

<400> SEQUENCE: 178
gccaucaggc caggggcgg 20

<210> SEQ ID NO 179
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#3

<400> SEQUENCE: 179
cuagggcuca ucucccagga 20

<210> SEQ ID NO 180
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#4

<400> SEQUENCE: 180
gacgugauca ggcucuacua 20

<210> SEQ ID NO 181
<211> LENGTH: 20
<212> TYPE: RNA
<213> ORGANISM: Artificial
<220> FEATURE:
<223> OTHER INFORMATION: Target specific sequence of the Cas9-SEPT9.1-crRNA#1

<400> SEQUENCE: 181
ucaggaggcc cuuauugugg 20

<210> SEQ ID NO 182
<211> LENGTH: 20
<212> TYPE: RNA
<213> ORGANISM: Artificial
<220> FEATURE:
<223> OTHER INFORMATION: Target specific sequence of the Cas9-SEPT9.1-crRNA#2

<400> SEQUENCE: 182
agggaggcgu cgcccguccc 20

<210> SEQ ID NO 183
<211> LENGTH: 20
<212> TYPE: RNA
<213> ORGANISM: Artificial
<220> FEATURE:
<223> OTHER INFORMATION: Target specific sequence of the Cas9-SEPT9.1-crRNA#3

<400> SEQUENCE: 183
ggagccucuc cgaggggcgg 20

<210> SEQ ID NO 184
<211> LENGTH: 20
<212> TYPE: RNA
<213> ORGANISM: Artificial
<220> FEATURE:
<223> OTHER INFORMATION: Target specific sequence of the Cas9-SEPT9.1-crRNA#4

<400> SEQUENCE: 184
guucuggcca uggagcgggg 20

<210> SEQ ID NO 185
<211> LENGTH: 20
<212> TYPE: RNA
<213> ORGANISM: Artificial
<220> FEATURE:
<223> OTHER INFORMATION: Target specific sequence of the Cas9-SEPT9.2-crRNA#1

<400> SEQUENCE: 185
ggcaaggacg gcauggccag 20

<210> SEQ ID NO 186
<211> LENGTH: 20
<212> TYPE: RNA
<213> ORGANISM: Artificial
<220> FEATURE:
<223> OTHER INFORMATION: Target specific sequence of the Cas9-SEPT9.2-crRNA#2

<400> SEQUENCE: 186
gaugucugag cagguaggug 20

<210> SEQ ID NO 187
<211> LENGTH: 20
<212> TYPE: RNA
<213> ORGANISM: Artificial
<220> FEATURE:
<223> OTHER INFORMATION: Target specific sequence of the Cas9-SEPT9.2-crRNA#3

<400> SEQUENCE: 187
aaacauguuc caagaagcuc 20

<210> SEQ ID NO 188
<211> LENGTH: 20
<212> TYPE: RNA
<213> ORGANISM: Artificial
<220> FEATURE:
<223> OTHER INFORMATION: Target specific sequence of the Cas9-SEPT9.2-crRNA#4

<400> SEQUENCE: 188
cagggaaacc ccuugcgaaa 20

<210> SEQ ID NO 189
<211> LENGTH: 20
<212> TYPE: RNA
<213> ORGANISM: Artificial
<220> FEATURE:
<223> OTHER INFORMATION: Target specific sequence of the Cas9-DMPK-crRNA#1

<400> SEQUENCE: 189
gcaguuugcc cauccacguc 20

<210> SEQ ID NO 190

```
<211> LENGTH: 20
<212> TYPE: RNA
<213> ORGANISM: Artificial
<220> FEATURE:
<223> OTHER INFORMATION: Target specific sequence of the Cas9-DMPK-
      crRNA#2

<400> SEQUENCE: 190

uccacgucag ggccucagcc                                               20


<210> SEQ ID NO 191
<211> LENGTH: 20
<212> TYPE: RNA
<213> ORGANISM: Artificial
<220> FEATURE:
<223> OTHER INFORMATION: Target specific sequence of the Cas9-DMPK-
      crRNA#3

<400> SEQUENCE: 191

ggaucauugc aggagcuaug                                               20


<210> SEQ ID NO 192
<211> LENGTH: 20
<212> TYPE: RNA
<213> ORGANISM: Artificial
<220> FEATURE:
<223> OTHER INFORMATION: Target specific sequence of the Cas9-DMPK-
      crRNA#4

<400> SEQUENCE: 192

ugcgggccgg uggcaacccu                                               20


<210> SEQ ID NO 193
<211> LENGTH: 145
<212> TYPE: DNA
<213> ORGANISM: Artificial
<220> FEATURE:
<223> OTHER INFORMATION: Generic Loop adaptor with Barcode (central N
      region) and target specific region (3' N region)
<220> FEATURE:
<221> NAME/KEY: misc_feature
<222> LOCATION: (59)..(74)
<223> OTHER INFORMATION: n is a, c, g, or t
<220> FEATURE:
<221> NAME/KEY: misc_feature
<222> LOCATION: (121)..(145)
<223> OTHER INFORMATION: n is a, c, g, or t

<400> SEQUENCE: 193

gcatcctctc tcttttcctc ctcctccgtt gttgttgttg agagaggatg cgctgaggnn     60

nnnnnnnnnn nnnncccaat gtcgttagat tagggaagcc attgtcttat gaggcccagg    120

nnnnnnnnnn nnnnnnnnnn nnnnn                                          145


<210> SEQ ID NO 194
<211> LENGTH: 93
<212> TYPE: DNA
<213> ORGANISM: Artificial
<220> FEATURE:
<223> OTHER INFORMATION: Generic Loop adaptor with target specific
      region (N)
<220> FEATURE:
<221> NAME/KEY: misc_feature
<222> LOCATION: (69)..(93)
<223> OTHER INFORMATION: n is a, c, g, or t

<400> SEQUENCE: 194

gcatcctctc tcttttcctc ctcctccgtt gttgttgttg agagaggatg cgctgagggt     60
```

tcgtgtgtnn nnnnnnnnnn nnnnnnnnnn nnn 93

<210> SEQ ID NO 195
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FMR1-left)

<400> SEQUENCE: 195
aaagttgagg tttgtttcac agtgg 25

<210> SEQ ID NO 196
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (CNRIP1-left)

<400> SEQUENCE: 196
gagggaagcg agaatggagg aatac 25

<210> SEQ ID NO 197
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (MAL-left)

<400> SEQUENCE: 197
acatgaaaca ccggcagtca acagg 25

<210> SEQ ID NO 198
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (HTT-left)

<400> SEQUENCE: 198
cggaaggtca gagcaggggt gcact 25

<210> SEQ ID NO 199
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SNCA-left)

<400> SEQUENCE: 199
tgtggagaag ggaatatcag aagca 25

<210> SEQ ID NO 200
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (EGFR-left)

<400> SEQUENCE: 200
tacaggggca gtgggacact tagcc 25

<210> SEQ ID NO 201
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (C9orf72-left)

<400> SEQUENCE: 201
ttttgaatgc acttaacagt gtctt 25

<210> SEQ ID NO 202
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (INA-left)

<400> SEQUENCE: 202
gctcgctctg caggtcctca ctgta 25

<210> SEQ ID NO 203
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SPG20-left)

<400> SEQUENCE: 203
tatttcaaag gctgtaacaa cctgg 25

<210> SEQ ID NO 204
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FBN1-left)

<400> SEQUENCE: 204
catttaacca cgtcctctcc tttgg 25

<210> SEQ ID NO 205
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.1-left)

<400> SEQUENCE: 205
actccctgga gtgggacttc atctg 25

<210> SEQ ID NO 206
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.2-left)

<400> SEQUENCE: 206
tggttggggg gtgggtgaca tatct 25

<210> SEQ ID NO 207
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SEPT9.1-left)

<400> SEQUENCE: 207
cctagctcct tccttcacac cttcc 25

<210> SEQ ID NO 208
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SEPT9.2-left)

<400> SEQUENCE: 208
cagccagcaa gcacctgggg tagag 25

<210> SEQ ID NO 209
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (DMPK-left)

<400> SEQUENCE: 209
cgctccccag agcagggcgt catgc 25

<210> SEQ ID NO 210
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FMR1-right)

<400> SEQUENCE: 210
gagctctccg aagtcccaat gctag 25

<210> SEQ ID NO 211
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (CNRIP1-right)

<400> SEQUENCE: 211
ggttaatagc tcacccttca aaatc 25

<210> SEQ ID NO 212
<211> LENGTH: 25
<212> TYPE: DNA
<213> ORGANISM: Artificial
<220> FEATURE:
<223> OTHER INFORMATION: Target Specific sequence for oligo binding (20bp of the Cpf1-crRNA + 5bp) (MAL-right)

<400> SEQUENCE: 212
acgctgacac ttctgagggt ggggt 25

```
<210> SEQ ID NO 213
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (HTT-right)

<400> SEQUENCE: 213

cccgccggga cagggagctg cagcg                                          25


<210> SEQ ID NO 214
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (SNCA-right)

<400> SEQUENCE: 214

ggaatattta ttccttgttc cactg                                          25


<210> SEQ ID NO 215
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (EGFR-right)

<400> SEQUENCE: 215

gtaagacagg tttaatattt tggtt                                          25


<210> SEQ ID NO 216
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (C9orf72-right)

<400> SEQUENCE: 216

gtgcaggacc tccctcctgt ttctg                                          25


<210> SEQ ID NO 217
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (INA-right)

<400> SEQUENCE: 217

tctttgtttg aagggctggg gcagg                                          25


<210> SEQ ID NO 218
<211> LENGTH: 25
<212> TYPE: DNA
<213> ORGANISM: Artificial
<220> FEATURE:
<223> OTHER INFORMATION: Target Specific sequence for oligo binding
      (20bp of the Cpf1-crRNA + 5bp) (SPG20-right)

<400> SEQUENCE: 218

caaaaacaca acaacaacaa aactg                                          25


<210> SEQ ID NO 219
```

<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (FBN1-right)

<400> SEQUENCE: 219
gccacaaata ctataccttt caaag 25

<210> SEQ ID NO 220
<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (NDRG4.1-right)

<400> SEQUENCE: 220
acccataatg ccacctcctt cttca 25

<210> SEQ ID NO 221
<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (NDRG4.2-right)

<400> SEQUENCE: 221
agacgtcgag agcccagggc ggtgc 25

<210> SEQ ID NO 222
<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.1-right)

<400> SEQUENCE: 222
agccactggc actctgcttg gcgtc 25

<210> SEQ ID NO 223
<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.2-right)

<400> SEQUENCE: 223
ggtgataact tgagcggagt gattt 25

<210> SEQ ID NO 224
<211> LENGTH: 25
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (DMPK-right)

<400> SEQUENCE: 224
attcctgaga aggctggaga ggcca 25

<210> SEQ ID NO 225
<211> LENGTH: 16

<212> TYPE: DNA
<213> ORGANISM: Artificial
<220> FEATURE:
<223> OTHER INFORMATION: Sequence Barcode BC001

<400> SEQUENCE: 225
gcgcgatacg atgact 16

<210> SEQ ID NO 226
<211> LENGTH: 16
<212> TYPE: DNA
<213> ORGANISM: Artificial
<220> FEATURE:
<223> OTHER INFORMATION: Sequence Barcode BC002

<400> SEQUENCE: 226
gtacacgctg tgacta 16

<210> SEQ ID NO 227
<211> LENGTH: 16
<212> TYPE: DNA
<213> ORGANISM: Artificial
<220> FEATURE:
<223> OTHER INFORMATION: Sequence Barcode BC003

<400> SEQUENCE: 227
gcgtatatct catgcg 16

<210> SEQ ID NO 228
<211> LENGTH: 16
<212> TYPE: DNA
<213> ORGANISM: Artificial
<220> FEATURE:
<223> OTHER INFORMATION: Sequence Barcode BC004

<400> SEQUENCE: 228
gtacatatgc gtctgt 16

<210> SEQ ID NO 229
<211> LENGTH: 16
<212> TYPE: DNA
<213> ORGANISM: Artificial
<220> FEATURE:
<223> OTHER INFORMATION: Sequence Barcode BC005

<400> SEQUENCE: 229
ctcagtgtga cacatg 16

<210> SEQ ID NO 230
<211> LENGTH: 16
<212> TYPE: DNA
<213> ORGANISM: Artificial
<220> FEATURE:
<223> OTHER INFORMATION: Sequence Barcode BC006

<400> SEQUENCE: 230
gcgtagacag actaca 16

<210> SEQ ID NO 231
<211> LENGTH: 16
<212> TYPE: DNA
<213> ORGANISM: Artificial
<220> FEATURE:
<223> OTHER INFORMATION: Sequence Barcode BC007

<400> SEQUENCE: 231
catagagaga tagtat 16

<210> SEQ ID NO 232
<211> LENGTH: 16
<212> TYPE: DNA
<213> ORGANISM: Artificial
<220> FEATURE:
<223> OTHER INFORMATION: Sequence Barcode BC008

<400> SEQUENCE: 232
cacacgagat ctcatc 16

<210> SEQ ID NO 233
<211> LENGTH: 16
<212> TYPE: DNA
<213> ORGANISM: Artificial
<220> FEATURE:
<223> OTHER INFORMATION: Sequence Barcode BC009

<400> SEQUENCE: 233
gtctacgctc gtcgcg 16

<210> SEQ ID NO 234
<211> LENGTH: 16
<212> TYPE: DNA
<213> ORGANISM: Artificial
<220> FEATURE:
<223> OTHER INFORMATION: Sequence Barcode BC010

<400> SEQUENCE: 234
cgtagctcga gatgag 16

<210> SEQ ID NO 235
<211> LENGTH: 16
<212> TYPE: DNA
<213> ORGANISM: Artificial
<220> FEATURE:
<223> OTHER INFORMATION: Sequence Barcode BC011

<400> SEQUENCE: 235
gctgtgtgtg ctcgtc 16

<210> SEQ ID NO 236
<211> LENGTH: 16
<212> TYPE: DNA
<213> ORGANISM: Artificial
<220> FEATURE:
<223> OTHER INFORMATION: Sequence Barcode BC012

<400> SEQUENCE: 236
cgctagagat ctgcta 16

<210> SEQ ID NO 237
<211> LENGTH: 16
<212> TYPE: DNA
<213> ORGANISM: Artificial
<220> FEATURE:
<223> OTHER INFORMATION: Sequence Barcode BC013

<400> SEQUENCE: 237
ctctcgtaga cagata 16

<210> SEQ ID NO 238
<211> LENGTH: 16
<212> TYPE: DNA
<213> ORGANISM: Artificial

```
<220> FEATURE:
<223> OTHER INFORMATION: Sequence Barcode BC014

<400> SEQUENCE: 238

gtctcatcat gctgcg                                                16


<210> SEQ ID NO 239
<211> LENGTH: 16
<212> TYPE: DNA
<213> ORGANISM: Artificial
<220> FEATURE:
<223> OTHER INFORMATION: Sequence Barcode BC015

<400> SEQUENCE: 239

catcgtcaca gacata                                                16


<210> SEQ ID NO 240
<211> LENGTH: 16
<212> TYPE: DNA
<213> ORGANISM: Artificial
<220> FEATURE:
<223> OTHER INFORMATION: Sequence Barcode BC016

<400> SEQUENCE: 240

cgcgcgagta tctcgt                                                16
```

IN VITRO ISOLATION AND ENRICHMENT OF NUCLEIC ACIDS USING SITE-SPECIFIC NUCLEASES

INTRODUCTION

The present invention is related to methods of nucleic acid isolation and enrichment.

Sample isolation and enrichment are critical first steps in the study of nucleic acids, influencing both nucleic acid quantity and quality, which in turn directly impacts the quality of data obtained in downstream applications (e.g. sensitivity, coverage, robustness, and reproducibility). This is particularly important in applications in which only certain target nucleic acid regions are analysed from a more complex mixture, or in cases where a low amount of target nucleic acid is present. As an example, the human "exome" (regions coding for proteins) represents only about 1% of the total genome, yet harbours 85% of DNA variations known to be associated with genetic disease. Thus, isolation and enrichment are of particular interest in clinical applications associated with the exome, such as diagnostics and genetic risk assessment.

While whole-genome analyses may be used even when few target regions are of interest, it is often not feasible to sequence an entire genome, due to technical, economical, and/or time constraints. Furthermore, whole-genome sequencing requires vastly increased computing power and storage to analyse the large amount of data generated. Nucleic acid isolation is therefore desirable in order to limit analyses to a specific subset of nucleic acid molecules.

To date, the main approaches used to isolate a subset of specific nucleic acid fragments are based on hybrid capture and/or targeted amplification techniques (see, for example, Mertes et al., Brief Funct Genomics, 2011, 10(6): 374-86 and WO 2016/014409). However, hybrid capture has low enrichment efficiency and generally requires at least two rounds of selection. Nucleic acids must also be denatured prior to capture, thereby removing any information encoded via the complementarity of the two strands. Amplification is also often required to increase the amount of nucleic acid material. However, amplification generates bias depending on the AT:GC ratio and the secondary structure of the fragments being amplified and becomes less efficient as the length of the amplified fragments increases. Furthermore, the number of target regions that can be amplified in a multiplexed fashion is limited due to primer cross-reactivity. In addition, all chemical modifications (e.g. base modifications) present in the original sequence are lost during the amplification process.

Given these limitations, there is a need for new methods for isolation of nucleic acid target regions. In particular, there is a need for a method of nucleic acid isolation that conserves the characteristics of the original nucleic acid molecule of interest (e.g. chemical modifications, such as base modifications, and nucleic acid sequence information, such as mismatches or SNPs), and that is compatible with downstream analysis technologies, such as nucleic acid sequencing.

DETAILED DESCRIPTION

The present invention is directed to a novel method for the isolation of specific nucleic acid target regions. In contrast to current nucleic acid isolation methods, all characteristics of the target nucleic acid molecules (e.g. chemical modifications, mismatches) are conserved, as the original nucleic acid molecule remains intact in the method of the present invention. In addition, multiplex assays can be easily designed with no risk of primer interactions or cross-recognition. Small sample sizes and samples with low levels of target nucleic acid may also be used in the present method without target amplification, as the efficiency of nucleic acid target isolation is high and with good specificity. In the absence of amplification, bias is also reduced. Furthermore, as all steps can be performed in the same container, this method is simple, with reduced possibility for error, when compared to the methods of the prior art. Sample loss is further reduced due to the absence of material transfer between containers. Finally, the method of the invention is advantageous over current methods as it is quick and inexpensive, may be performed directly on samples, has few processing steps, and is compatible with existing downstream nucleic acid analysis platforms, including "third-generation" sequencing technologies, wherein single nucleic acid molecules are analysed within micro-structures, such as nanopores, zero-mode wave guides, or microwells. Notably, the present method provides isolated specific nucleic acid target regions that may comprise specific single-stranded nucleic acid overhangs on either or both ends, onto which various adaptors or linkers can be specifically ligated, providing flexibility for use of target regions in a wide variety of downstream analyses and applications.

The present invention more specifically provides a method of isolating a target region of a nucleic acid molecule from a sample based on the use of a site-specific nuclease, such as a Type II Cas protein-gRNA complex, which remains bound to a target nucleic acid of interest, thereby shielding it from external treatments, such as exonuclease digestion.

The Type II Cas protein is an RNA-guided DNA endonuclease. In order to have functional activity, the Type II Cas protein complexes with a "guide RNA," or "gRNA," to form a "Type II Cas protein-gRNA complex." This complex can then specifically recognize and bind to a nucleic acid target region. Binding specificity is determined by the gRNA, which comprises a "guide segment," whose sequence must be at least partially complementary to that of the target region. The guide sequence hybridizes with the target region. Binding of the Type II Cas protein-gRNA complex to the nucleic acid target region further requires the presence of a short, conserved sequence in the target nucleic acid molecule that is located immediately adjacent to the hybridized region. This sequence is known as the protospacer-associated motif or "PAM." Thus, Type II Cas protein-gRNA complex binding to a target region comprises both nucleic acid hybridization via the guide segment and interaction of the Type II Cas protein itself with the PAM. Following binding of the Type II Cas protein-gRNA complex to a target region, the Type II Cas protein cleaves the nucleic acid by breaking the phosphodiester bonds between two adjacent nucleotides in each of the strands of a double-stranded nucleic acid molecule. Specifically, one domain of the Type II Cas protein cleaves the nucleic acid strand that is hybridized with the gRNA, while a second domain of the Type II Cas protein cleaves the non-hybridized nucleic acid strand. These aspects are further detailed below.

In addition to the enzymatic activity of the Type II Cas protein described above, the inventors have surprisingly found that a Type II Cas protein-gRNA complex will remain bound to its nucleic acid target, even after the Type II Cas protein has enzymatically cleaved the nucleic acid. Even more surprisingly, the inventors have found that this interaction is extremely stable, and can last for up to several hours. Based on this property, the inventors have developed a novel method of nucleic acid isolation, wherein a Type II Cas protein-gRNA complex specifically binds a target nucleic acid region. Binding of the Type II Cas protein-gRNA complex to a target region thereby shields it from external treatments. As unbound nucleic acid molecules are not shielded from external treatments, the target region may be specifically isolated from a more complex sample comprising a population of nucleic acid molecules.

Thus, according to a first aspect of the invention, a method of isolating a target nucleic acid region is provided, said method comprising the step of:

a) contacting a population of nucleic acid molecules with at least one Type II Cas protein-gRNA complex, wherein said gRNA comprises a guide segment that is complementary to a sequence comprised in the target region of at least one nucleic acid molecule.

When the Type II Cas protein-gRNA complex binds to a target region, a Type II Cas protein-gRNA-nucleic acid complex is formed. As can be easily understood by the skilled person, when the nucleic acid population is contacted with more than one Type II Cas protein-gRNA complex in step a), more than one Type II Cas protein-gRNA-nucleic acid complex may be formed.

While the Type II Cas protein is the preferred site-specific nuclease of the invention, other site-specific nucleases, such as Type I or Type III Cas proteins, transcription activator-like effector nucleases (TALENs), or zinc-finger proteins that stably bind a nucleic acid target region are also included in the scope of the invention.

The terms "a," "an," and "the," as used herein include plural forms unless the content of the present application clearly dictates otherwise. As an example, "a target region" therefore includes two or more target regions.

The term "sample" as used herein refers to any material or substance comprising a population of nucleic acid molecules, including, for example, biological, environmental, or synthetic samples. A "biological sample" may be any sample which may contain a biological organism, such as, for example, bacteria, viruses, archaea, animals, plants, and/or fungi. A "biological sample" according to the invention also refers to a sample which may be obtained from a biological organism, such as a cellular extract obtained, for example, from bacteria, viruses, archaea, plants, fungi, animals, and/or other eukaryotes. Molecules of the nucleic acid of interest can be obtained directly from an organism or from a biological sample obtained from an organism, e.g., from blood, urine, cerebrospinal fluid, seminal fluid, saliva, sputum, stool and tissue (such as cell tissue or plant tissue). Any cell, tissue or body fluid specimen may be used as a source for nucleic acid for use in the invention. Molecules of a nucleic acid of interest can also be isolated from cultured cells, such as a primary cell culture or a cell line. The cells or tissues from which nucleic acids of interest are obtained can be infected with a virus or other intracellular pathogen. A sample can also be total nucleic acids extracted from a biological specimen. An "environmental sample" may be any sample comprising nucleic acid that is not taken directly from a biological organism (e.g. soil, seawater, air, etc.), and may comprise nucleic acids that are no longer present within a biological organism. A "synthetic sample" comprises artificial or engineered nucleic acids. Alternatively, the sample may be from any source suspected of comprising a target nucleic acid region.

In certain embodiments, the method of the invention may comprise one or more steps of treating the sample to facilitate nucleic acid isolation according to the method of the present invention. As a non-limiting example, the sample may be concentrated, diluted, or disrupted (e.g. by mechanical or enzymatic lysis). Nucleic acids may be purified prior to isolation of the target region by the present method, partially purified, or be in non-purified form.

The term "isolation" and "isolating" as used herein refer to an increase in the proportion of one or more target nucleic acid regions with respect to one or more other molecules in a sample. As a non-limiting example, these other molecules may comprise proteins, lipids, carbohydrates, metabolites, nucleic acids, or combinations thereof. Isolation of the target nucleic acid region, as used herein, may refer more specifically to an increase in the proportion of the one or more target nucleic acid regions in a sample by at least 1-fold (e.g. 1, 2, 3, 4, 5, 10, 20, 30, 40, 50, 60, 70, 80, 90, 100, 250, 500, 750, 1000, or 10,000-fold or more), as compared to the one or more other molecules in a sample, or as compared to the total number of molecules in the initial sample (i.e. prior to performing the method of the invention). Isolation of the target nucleic acid region may also refer to an increase in the proportion of the target nucleic acid region in the sample by at least 5% (e.g. 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%) when compared to the level of the one or more other molecules in a sample. When the proportion of the target nucleic acid region is 100%, no other molecules are comprised in the sample. The term "enrichment" as used herein refers more specifically to the isolation of one or more target nucleic acid regions with respect to the other nucleic acid molecules in the sample. As an example, enrichment of the target region refers to an increase in the proportion of the isolated target region as compared to the amount of total initial nucleic acid, wherein the proportion of the isolated target region is increased by at least 10%, 20%, 30%, 40%, 50%, 60%, 65%, 70%, 75%, 80%, 85%, 90%, 95%, 96%, 97%, 98%, 99% or 100%.

According to a preferred embodiment, the proportion of the isolated target region, as compared to the amount of total initial nucleic acid is increased by at least 10%, more preferably at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, even more preferably at least 99% or 100%.

According to one embodiment, the isolated nucleic acid target region is enriched by at least 10-fold, at least 20-fold, at least 50-fold, at least 100-fold, at least 250-fold, at least 500-fold, at least 750-fold, preferably by at least 1000-fold, at least 10,000-fold, at least 100,000-fold, even more preferably by at least 1,000,000-fold, at least 2,000,000-fold, or at least 3,000,000-fold. As a particular example, the 100% enrichment of a single 1 kb fragment from a population of nucleic acid molecules equivalent to the human genome of approximately 3.2 billion bp represents a 3,000,000-fold increase.

According to an alternative embodiment, the isolated target region is substantially pure. By "substantially pure" is meant that the isolated target region comprises at least 99%, preferably at least 99.5%, of the total nucleic acid in the sample following isolation of the target region according to the method of the present invention.

According to a preferred embodiment, prior to isolation, the target region of interest comprises less than 10% of the total nucleic acid in the sample, preferably less than 5%, more preferably less than 2%, less than 0.05%, less than 0.02%, even more preferably less than 0.01%, less than 0.005%, less than 0.001%, less than 0.0005%, less than 0.0001%, less than 0.00005%, less than 0.00001%, or less than 0.0000005%. The skilled person will realize that the amount or percent of the target region of interest within the total nucleic acid of a sample will vary depending on the number of target regions to be isolated and the length of the target regions(s) to be isolated. As a non-limiting example, a 1 kb target region of interest within the human genome of approximately 3.2 billion bp represents less than 0.0000005% of the total genome.

The term "nucleic acid molecule" as defined herein refers to a polymer of nucleotide monomers including deoxyribonucleotides (DNA), ribonucleotides (RNA), or analogs thereof, as well as combinations thereof (e.g. DNA/RNA chimeras). The deoxyribonucleotide and ribonucleotide monomers described herein refer to monomeric units which comprise a triphosphate group, the adenine ("A"), cytosine ("C"), guanine ("G"), thymine ("T"), or uracil (U) nitrogenous base, and a deoxyribose or ribose sugar, respectively. Modified nucleotide bases are also encompassed herein, wherein the nucleotide bases are, for example, hypoxanthine, xanthine, 7-methylguanine, inosine, xanthinosine, 7-methylguanosine, 5,6-dihydrouracil, 5-methylcytosine, pseudouridine, dihydrouridine, or 5-methylcytidine. In the context of the present invention, when describing nucleotides, "N" represents any nucleotide, "Y" represents any pyrimidine, and "R" represents any purine. Nucleotide monomers are linked by inter-nucleotide linkages, such as phosphodiester bonds, or phosphate analogs thereof and associated counter ions (e.g., H+, NH4+, Na+). Nucleic acid molecules of the invention may be double-stranded or single-stranded and will most often be double-stranded DNA. However, it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired, as well as single-stranded DNA and single-stranded RNA. In particular, the invention also applies to the secondary structures of a sole single-stranded DNA or of a sole single-stranded RNA. Optionally, when the nucleic acid molecule is single-stranded RNA (e.g. mRNA) or a single-stranded RNA-single-stranded RNA duplex (e.g. viral dsRNA), said RNA may be reverse transcribed prior to being contacted with the Type II Cas protein-gRNA complex. Duplexes may consist of at least partial re-pairing of two single nucleic acid strands obtained from samples of different origins. Nucleic acid molecules may be naturally occurring (e.g. of eukaryotic or prokaryotic origin), or synthetic. Nucleic acid molecules may notably comprise genomic DNA (gDNA), cDNA, hnRNA, mRNA, rRNA, tRNA, microRNA, mtDNA, cpDNA, cfDNA (such as ctDNA or cffDNA), cfRNA and the like. Nucleic acid molecule length may range from only a few monomeric units (e.g. oligonucleotides, which may range, for example, from less than 50 to up to 200 monomers in length) to several thousand, tens of thousands, hundreds of thousands, or millions of monomeric units. Preferably, the nucleic acid molecules comprise one or more cfDNA molecules. Preferably, the length of the nucleic acid molecules is comprised between about 125 and 225 bp, preferably between 130 and 200 bp. In the present application, it should be understood that nucleic acid molecules are expressed in the 5' to 3' direction from left to right, unless specified otherwise.

The term "population of nucleic acid molecules" refers to more than one nucleic acid molecule. Said population may comprise one or more different nucleic acid molecules, of any length, of any sequence, as defined above. A population of nucleic acid molecules may notably comprise more than $10^3$, $10^4$, $10^5$, $10^6$, $10^7$, $10^8$, $10^9$, or $10^{110}$ different nucleic acid molecules.

As used herein, the term "Type II Cas protein" refers to an RNA-guided enzyme having endonuclease activity. As a non-limiting example, the Type II Cas protein may be from one of the following species: *Streptococcus pneumoniae, Streptococcus pyogenes, Streptococcus thermophilus, Staphylococcus aureus, Neisseria meningitidis, Treponema denticola, Francisella tularensis, Francisella novicida, Pasteurella multocida, Streptococcus mutans, Campylobacter jejuni, Campylobacter lari, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globosa, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pasteuri, Filifactor alocis, Veillonella* sp. *Suterella wadsworthensis, Leptotrichia* sp., *Corynebacterium diphtheriae, Acidaminococcus* sp., or *Lachnospiraceae* sp. Type II Cas proteins and protein orthologs have also been identified in other bacterial species and are notably described in Example 1 of PCT application no. WO 2015/071474, incorporated herein by reference. In some embodiments, the Type II Cas protein of the invention may be a homolog or an ortholog, for example, to a Type II Cas protein of one of the species listed above.

As a non-limiting example, the Type II Cas protein may be J3F2B0, Q0P897, Q6NKI3, AOQ5Y3, Q927P4, A11Q68, C9X1G5, Q9CLT2, J7RUA5, Q8DTE3, Q99ZW2, G3ECR1, Q73QW6, G1UFN3, Q7NAI2, E6WZS9, A7HP89, D4KTZ0, D0W2Z9, B5ZLK9, F0RSV0, A0A1L6XN42, F2IKJ5, S0FEG1, Q6KIQ7, A0A0H4LAU6, F5X275, F4AF10, U5ULJ7, D6GRK4, D6KPM9, U2SSY7, G4Q6A5, R9MHT9, A0A111NJ61, D3NT09, G4Q6A5, AOQ7Q2, or U2UMQ6. Accession numbers are from UniProt (www.uniprot.org), version last modified on Jan. 10, 2017. As a non-limiting example, the gene encoding the Type II Cas protein may be any gene comprising a nucleotide sequence wherein said sequence generates the amino acid sequence of the corresponding Type II Cas protein, such as one of those listed above. The skilled person will easily understand that the nucleotide sequence of the gene may vary due to degeneracy of the genetic code, without altering the amino acid sequence. The Type II Cas protein of the invention may furthermore be codon-optimized for expression in a bacterial (e.g. *E. coli*), insect, fungal, or mammalian cell.

According to a preferred embodiment, the Type II Cas protein used in the method is from one of the species listed above, more preferably from *Streptococcus pyogenes, Neisseria meningitidis, Streptococcus thermophiles*, or *Treponema denticola*, even more preferably from *Streptococcus pyogenes*.

According to a preferred embodiment, the Type II Cas protein of the present invention is Cas9, Cpf1, C2c1, C2c3, or C2c2 (Cas13a), preferably Cas9 or Cpf1, even more preferably Cas9.

Although the wild-type Type II Cas protein has endonuclease activity, this activity is not required in the context of the present invention. Indeed, the inventors have surprisingly found that the tight binding of the Type II Cas protein-gRNA complex to its nucleic acid target is independent of its catalytic activity. Thus, a variant or mutant of the wild-type Type II Cas protein may be used. In particular, a mutated Type II Cas protein lacking the ability to cleave one or both strands of the target nucleic acid molecule containing a target region may be used. Indeed, in addition to the wild-type Type II Cas protein, both a Type II Cas nickase and a catalytically inactive Type II Cas protein, such as dCas9, remain strongly bound to a nucleic acid molecule at the region targeted by the gRNA. Alternatively, a mutated Type II Cas protein retaining its endonuclease activity but having improved binding specificity (e.g. eSpCas9, as described in Slaymaker et al., *Science,* 2015, 351(6268): 84-86) is of particular interest in the context of the present invention.

The term "Type II Cas nickase" as used herein, refers to a modified Type II Cas protein comprising one inactive catalytic nuclease domain and one active catalytic nuclease domain. A Type II Cas nickase complexed with a gRNA will bind to a specific nucleic acid sequence as described above, but will only break the phosphodiester bond between two nucleotides in one strand of a double stranded nucleic acid. The Type II Cas nickase may cleave either the nucleic acid strand that is hybridized with the gRNA, or the non-hybridized nucleic acid strand which is at least partially homologous to the gRNA. The "nick site" refers to the site at which the double-stranded nucleic acid molecule has undergone a break on one strand. A 3' hydroxyl group and a 5' phosphate group are produced at the nick site.

The terms "catalytically dead," "catalytically inactive," or "dead," as used herein, refer to a modified Type II Cas protein comprising two catalytically inactive nuclease domains. A catalytically inactive Type II Cas protein complexed with a gRNA will bind a specific target region as described above, but will not cleave or nick either the nucleic acid strand that is hybridized with the gRNA, or the non-hybridized nucleic acid strand which is at least partially homologous to the gRNA.

According to a first preferred embodiment, the Type II Cas protein of the invention is a wild-type Type II Cas protein, such as one of those listed above, more preferably a wild-type Cas9 or Cpf1 protein. According to a second preferred embodiment, the Type II Cas protein of the invention is a Type II Cas nickase, preferably a Cas9 nickase (Cas9n) or a Cpf1 nickase. According to a third preferred embodiment, the Type II Cas protein of the invention is catalytically dead, preferably a catalytically dead Cas9 protein (dCas9) or a catalytically dead Cpf1 protein. According to a fourth preferred embodiment, the Type II Cas protein of the invention has been mutated to have improved binding specificity, more preferably eSpCas9, SpCas9-HF1, or HypaCas9. Preferably, Cpf1 has been modified to have increased binding specificity (e.g. as suggested in Strohkendl et al., Molecular Cell, 2018, 71:1-9). This notably improves mismatch discrimination (e.g. associated with SNP identification).

A modified Type II Cas protein may comprise one or more modifications causing specific inactivation of one or both of its nuclease domains. Preferably, said modifications do not affect Type II Cas protein-gRNA complex formation, Type II Cas protein recognition of the PAM motif, and/or the strength and/or stability of binding to the target region and/or binding of the Type II Cas protein-gRNA complex to the target region. As a non-limiting example, possible modifications to the Type II Cas protein include substitutions at one or more of the following amino acids: E762, HH983 or D986, D10, H840, G12, G17, N854, N863, N982, or A984, wherein amino acids are numbered according to the amino acid sequence of the Cas9 protein of *S. pyogenes* (having, for example, accession number Q99ZW2 in the Uniprot database), or at the equivalent amino acid position(s) in another Type II Cas protein. As an example, the one or more amino acids may be substituted by an alanine (e.g. E762A, HH983AA or D986A, D10A, H840A, G12A, G17A, N854A, N863A, N982A or A984A), or by another amino acid which causes inactivation of the corresponding catalytic domain.

Preferably, the Type II Cas nickase comprises a substitution at the amino acid position equivalent to the H840 (e.g. H840A) or D10 (e.g. D10A) position of the Cas9 protein. Preferably, Cas9n comprises a substitution at the amino acid position equivalent to H840 (e.g. H840A) or at position D10 (e.g. D10A). Depending on the Type II Cas nickase variant used (e.g. comprising a substitution at D10 or H840), the Type II Cas nickase will nick either the gRNA-hybridized strand or the non-hybridized strand. In particular, a Type II Cas nickase comprising a substitution at D10 will nick the gRNA-hybridized strand, while a Type II Cas nickase comprising a substitution at H840 will nick the strand that is not hybridized to the gRNA. Alternatively, the Type II Cas nickase may comprise a substitution at the amino acid position equivalent to the R1226 (e.g. R1226A) of the Cpf1 protein. A Type II Cas nickase comprising a substitution at R1226 will nick the strand that is not hybridized to the gRNA.

Preferably, the catalytically inactive Type II Cas protein comprises substitutions at least at both of the amino acid positions equivalent the D10 and H840 in the Cas9 protein.

Preferably, dCas9 comprises substitution at least at both amino acid positions D10 and H840.

The term "guide RNA" or "gRNA" as used herein, refers to two guide RNA molecules, consisting of a crRNA molecule and a tracrRNA molecule. Alternatively, the term gRNA as used herein, refers to a single guide RNA molecule, or sgRNA, that includes both crRNA and tracrRNA sequence segments. Alternatively, the gRNA may consist of a crRNA molecule only. The gRNA molecule may be chemically modified, for example comprising base, sugar, or phosphate modifications of one or more ribonucleotides. Optionally, the 5' and/or 3' ends of the gRNA molecule may be modified, for example by covalent conjugation to another molecule or a chemical group.

The crRNA molecule or segment is preferably 20 to 75 nucleotides in length, more preferably 30 to 60 nucleotides, even more preferably 40 to 45 nucleotides in length. The crRNA molecule or segment preferably comprises a first region, referred to herein as the "guide segment," whose sequence is at least partially complementary to the nucleic acid target region. An exemplary generic crRNA nucleotide sequence is shown in SEQ ID NO: 24, with the guide segment represented by the stretch of 'N' nucleotides. Preferably, the guide segment of the gRNA of the present invention comprises at least 70%, at least 80%, at least 85%, at least 90%, at least 95%, at least 96%, at least 97%, at least 98%, at least 99%, or more preferably 100% sequence complementarity with the nucleic acid target region. Preferably, when complementarity is less than 100%, mismatches are located near the crRNA end that hybridizes farthest from the PAM. As an example, when the Type II Cas protein is Cas9, mismatches are preferably comprised at the 5' end of the crRNA molecule or segment (e.g. within the first 7 nucleotides), as Cas9 recognizes a PAM at the 3' end of the crRNA. Alternatively, when the Type II Cas protein is Cpf1, mismatches are preferably comprised at the 3' end of the crRNA molecule or segment (e.g. within the last 7 nucleotides), as Cpf1 recognizes a PAM at the 5' end of the crRNA. The guide segment is preferably at least 10, 11, 12, 13, 14, 15, 16, 17, 18, 19, 20, 21, 22, 23, 24, or 25 nucleotides in length, more preferably 15, 16, 17, 18, 19, 20, 21, 22, 23, 24, or 25, even more preferably 20, 21, 22, 23, or 24 nucleotides in length. Alternatively, the guide segment is preferably from 10 to 30, 15 to 25, 17 to 24, more preferably from 20 to 23, nucleotides in length. The crRNA molecule or segment preferably comprises a second region, referred to herein as the "tracr-mate segment." The tracr-mate segment comprises a sequence that is preferably at least partially complementary to the tracrRNA molecule or segment, more preferably at least partially complementary to the 5' end of the tracrRNA. The tracr-mate segment is preferably at least 10, 11, 12, 13, 14, 15, 16, 17, 18, 19, 20, 25, 30, 40, 50 nucleotides in length, more preferably at least 15 nucleotides in length, even more preferably at least 20 nucleotides in length. Preferably, the guide segment is located at the 5' end of the crRNA molecule or segment. Preferably, the tracr-mate segment is located at or near the 3' end of the crRNA molecule or segment.

The tracrRNA molecule or segment is preferably 10 to 175 nucleotides in length, more preferably 40 to 110, more preferably 60 to 90, even more preferably 65 to 80 nucleotides in length. The tracrRNA molecule or segment preferably comprises at least one secondary structure, preferably at least two secondary structures, more preferably at least three secondary structures, even more preferably three or four secondary structures. Preferably, the at least one secondary structure is located at or near the 3'-end of the tracrRNA molecule or segment. An exemplary generic tracrRNA nucleotide sequence is shown in SEQ ID NO: 25. The tracrRNA molecule preferably comprises a tracrRNA binding segment that is complementary to the tracr-mate segment of the crRNA. Preferably, the tracrRNA binding segment comprises a sequence that is at least 50%, 60%, 70%, 80%, 85%, 90%, 95%, 99%, or 100% complementary to the tracr-mate segment of the crRNA. Preferably, the tracrRNA binding segment is at least 10 nucleotides in length. The term "at or near the 5'-end" of a nucleic acid molecule as used herein refers to placement of a segment or structure within the first half of the molecule, from 5' to 3'. Similarly, the term "at or near the 3'-end" of a nucleic acid molecule as used herein refers to placement of a segment or structure within the last half of the molecule.

As a non-limiting example, a "secondary structure" present in the gRNA may be a stem-loop or hairpin, bulge, tetraloop, and/or pseudoknot. The terms "hairpin" or "stem-loop" as used herein refer to a double helix wherein the 5'-end of one strand is physically linked to the 3'-end of the other strand through an unpaired loop. The said physical link can be either covalent or non-covalent. Preferentially, the said physical link is a covalent bond. Thus, a hairpin consists of a double-stranded stem and an unpaired single-stranded loop. According to a preferred embodiment, said gRNA comprises at least one hairpin secondary structure.

According to a first preferred embodiment, the gRNA is a sgRNA molecule comprising both crRNA and tracrRNA segments. An exemplary generic sgRNA nucleotide sequence is shown in SEQ ID NO: 26, with the guide segment represented by the stretch of 'N' nucleotides. Even more preferably, the sgRNA consists of crRNA and tracrRNA segments. Preferably, the crRNA and tracrRNA segments are fused together. Said segments are preferably fused together by a phosphodiester bond or a nucleic acid linker comprising one or more nucleotides. Said sgRNA is preferably from 30 to 180 nucleotides in length, more preferably from 40 to 90 nucleotides in length. Preferably, the 3'-end of the crRNA is fused to the 5'-end of the tracrRNA. Preferably, the crRNA and tracrRNA are fused by the addition of a linker. Alternatively, the crRNA and tracrRNA molecules may be fused by chemical linkage, such as a covalent bond (e.g. a triazole linkage).

According to a second preferred embodiment, the gRNA is composed of two separate RNA molecules consisting of a crRNA molecule and a tracrRNA molecule.

According to a third preferred embodiment, when the Type II Cas protein is Cpf1, the gRNA consists only of a crRNA molecule. When the gRNA is only a crRNA molecule, at least the guide segment must be present. An exemplary generic crRNA nucleotide sequence is shown in SEQ ID NO: 33, with the guide segment represented by the stretch of 'N' nucleotides. Preferably, the crRNA molecule further comprises a secondary structure, such as a hairpin. Preferably, the crRNA molecule does not comprise a tracr-mate segment. Preferably, the guide segment is located at the 3'-end of the crRNA molecule. Preferably the secondary structure is located at or near the 5'-end of the crRNA molecule. Preferably, said crRNA is 40 to 50 nucleotides in length.

The term "complementary" as used herein refers to ability of one nucleic acid sequence or molecule (e.g. the gRNA) to undergo sequence-specific antiparallel nucleotide base pairing interactions with another nucleic acid sequence or molecule (e.g. the target region), resulting in the formation of a duplex or other higher-ordered structure. The main type of interaction is nucleotide base specific, e.g., A:T, A:U, and G:C, by Watson-Crick and Hoogsteen-type hydrogen bonding. This is also known as "nucleic acid binding," "hybridization," or "annealing." Conditions under which a nucleic acid hybridizes to a complementary region of a target nucleic acid are well-known in the art (see, for example, Nucleic Acid Hybridization, A Practical Approach, Hames and Higgins, eds., IRL Press, Washington, D.C. (1985)). Hybridization conditions depend upon the particular application, and can be routinely determined by a person skilled in the art without undue experimentation.

In the context of the present invention, complementary binding does not mean that the two nucleic acid sequences or molecules (e.g. the gRNA and the target region, or the tracr-mate segment and the tracrRNA) must be entirely complementary to each other. Furthermore, it is not necessary for the crRNA sequence segment or molecule to be entirely complementary to the target region. Indeed, it is known that a Type II Cas protein-gRNA complex can specifically bind to a sequence comprised in a target region having as few as 8 or 9 bases of complementarity with the gRNA. Preferably, no mismatches are present between the 10 bases of the gRNA that are closest to the PAM and the corresponding 10 bases of the complementary nucleic acid sequence which are located closest to the PAM, more preferably between the 6 bases of the gRNA that are closest to the PAM and the corresponding 6 bases of the complementary nucleic acid sequence which are located closest to the PAM, even more preferably between the base(s) of the gRNA which are located 4, 5, and/or 6 bases from the PAM and the corresponding bases of the complementary nucleic acid sequence which are located 4, 5, and/or 6 bases from the PAM. Indeed, if a mismatch is present at one or more of said base locations, binding will be unstable and protection of the target region from exonuclease digestion by the Type II Cas protein-gRNA complex will be reduced or even abolished (see also FIG. 1A). Furthermore, off-target hybridization can be reduced by increasing the length of the crRNA segment, or by placing mismatches at or near the end of the crRNA segment that is furthest from the PAM, as indicated previously herein. Alternatively, the gRNA may be modified to have increased binding specificity via the presence of one or more modified bases or chemical modifications. Moreover, a nucleic acid may hybridize over one or more regions such that intervening or adjacent regions are not involved in the hybridization event (e.g., a loop or hairpin structure). The person skilled in the art can easily design one or more gRNA molecules based on his general knowledge and in view of the parameters detailed above, according to the nucleic acid region(s) to be targeted for isolation.

The term "protospacer adjacent motif" or "PAM" as used herein, refers to a short nucleotide sequence (e.g. 2 to 6 nucleotides) which is recognized directly by the Type II Cas protein itself. The PAM sequence and its placement will vary according to the Type II Cas protein used, and can easily be determined by the person skilled in the art according to his general knowledge, or using techniques such as that described in Karvelis et al., *Genome Biology,* 2015, 16:253. Binding of the Type II Cas protein to the PAM is thought to slightly destabilize a double stranded nucleic acid, thereby allowing hybridization of the gRNA to the target region. The most well-known and widely used Type II Cas protein is the Cas9 protein of *S. pyogenes*, which recognizes the PAM 5'-NGG-3'. In contrast, the Cas9 protein of *S. aureus* recognizes the PAM 5'-NNGRRT-3', the Cas9 of *N. meningitidis* recognizes the PAM 5'-NNNNGATT-3', the Cas9 of *S. thermophilus* recognizes the PAM 5'-NNAGAA-3', the Cas9 of *T. denticola* recognizes the PAM 5'-NAAAAC-3', an engineered Cas9 protein derived from *F. novicida* recognizes the PAM 5'-YG-3', the Cpf1 protein of *F. novicida* recognizes the PAM 5'-TTTN-3' or 5'-YTN-3', the Cpf1 protein of Acidaminococcus sp. recognizes the PAM 5'-TTTN-3. The PAM motif is generally located on the non-hybridized strand of a double-stranded target nucleic acid molecule at a site that is immediately adjacent to the 5' or 3' end of the target region that is hybridized to the gRNA. The required placement of the PAM depends on the Type II Cas protein used (e.g. the PAM is preferably located immediately adjacent to the 3'-end of the gRNA when using the Cas9 protein, while the PAM is preferably located immediately adjacent to the 5'-end of the gRNA when using the Cpf1 protein). Alternatively, the PAM motif may be comprised in the gRNA molecule itself or in a separate DNA oligonucleotide that is added to the sample. As an example, addition of a PAM to the sample via one of these means may be necessary when using the present method to isolate single-stranded RNA molecules.

According to a first embodiment, the PAM is located on the non-hybridized strand of the target region immediately adjacent to the 3' end of the gRNA. According to a second embodiment, the PAM is located on the non-hybridized strand of the target region immediately adjacent to 5' end of the gRNA. According to a third embodiment, the PAM is comprised on the gRNA molecule itself or on a DNA oligonucleotide.

The "target nucleic acid region" or "target region" as defined herein refers to a specific nucleic acid molecule that is present within a more complex sample or population of nucleic acid molecules. The "target nucleic acid region" or "target region" as defined herein may also refer to a specific nucleic acid region that is present within a larger nucleic acid molecule, and that is specifically targeted for isolation. The target nucleic acid region comprises one or more sequences that is/are at least partially complementary to the guide segment of the crRNA molecule or gRNA. The target nucleic acid region preferably comprises a PAM that is immediately adjacent to said sequence, more preferably on the non-hybridized strand. The target nucleic acid region may further comprise a nucleic acid region that is adjacent to the target region comprising the sequence that is at least partially complementary to the guide segment of the crRNA molecule or gRNA. This region is referred to herein as the "adjacent region," and is further defined below. According to a specific aspect, the target nucleic acid region may comprise an adjacent region that is located between a first and a second nucleic acid target region (e.g. a central adjacent region), wherein said first and second target regions comprise sequences that are at least partially complementary to one or more guide segments of a crRNA molecule or gRNA(s)). As an example, when a nucleic acid molecule is contacted with two or more Type II Cas protein-gRNA complexes, each comprising a different gRNA, a single nucleic acid target region comprising the Type II Cas protein-gRNA-nucleic acid complexes and the adjacent region between the two complexes may be isolated. Alternatively, two or more different nucleic acid target regions, each forming a Type II Cas protein-gRNA-nucleic acid complex may be isolated. These aspects are further detailed below. The "target nucleic acid region" of the invention may therefore comprise one or more different regions, preferably at least 2, 5, 10, 25, 50, 100, or more regions.

The term "region" as used herein refers to an uninterrupted nucleotide polymer. Although a single gRNA may permit the isolation of multiple target regions (for example, due to non-specific binding, or recognition of a target region that is present more than once in the nucleic acid molecule), in the context of the present invention, each gRNA preferably recognizes a single target region. When two different gRNAs are used, preferably, at least two different regions are targeted. However, it is equally desirable to target an "adjacent region" to the target region. Said adjacent target region may, for example, be isolated when at least two different gRNAs target a first target region and a second target region flanking said adjacent region. Additional embodiments are described below.

The target nucleic acid region may be coding or non-coding, or a combination of the two. The target region may be genomic or episomic. The target region may comprise one or more repeat regions, rearrangements, duplications, translocations, deletions, mismatches, SNPs, and/or modified bases, such as epigenetic modifications.

According to a preferred embodiment, the nucleic acid molecule is contacted with at least two Type II Cas protein-gRNA complexes each comprising a different gRNA. More preferably the nucleic acid molecule is contacted with at least 5, at least 10, at least 25, at least 50, or at least 100 Type II Cas protein-gRNA complexes each Type II Cas protein-gRNA complex binding to a different target region.

According to a preferred embodiment of the invention, at least two target regions are isolated, more preferably at least 5, at least 10, at least 25, at least 50, or at least 100 target regions are isolated.

A target nucleic acid region is at least about 44 nucleotides in length. Indeed, the inventors have found that a Type II Cas protein-gRNA complex, such as a Cas9-gRNA complex, can protect a nucleic acid target region of at least about 44 nucleotides. Preferably, the target nucleic acid region will have a length of at least 50, 100, 250, 500, 1,000, 5,000, 10,000, 20,000, 30,000, 40,000, 50,000, 60,000, 70,000, 80,000, 90,000, or 100,000 nucleotides.

According to the method of the present invention, after contacting a population of nucleic acid molecules with at least one Type II Cas protein-gRNA complex, to form at least one Type II Cas protein-gRNA nucleic acid molecule complex, said method further comprises the step of degrading nucleic acid molecules that are not comprised in the Type II Cas protein-gRNA-nucleic acid complex(es). Degradation may be partial or complete. This may depend on incubation conditions, sample composition, the nucleic acid population itself (e.g. nucleic acid structures), or other variables as known to the skilled person. As a non-limiting example, degradation may comprise an enzymatic treatment. As a further non-limiting example, the population of nucleic acid molecules may be contacted with at least one enzyme having exonuclease activity. The term "enzyme having exonuclease activity" as used herein refers to an enzyme having 5' to 3' and/or 3' to 5' exonuclease activity. Said enzyme having exonuclease activity may be an exoribonuclease or an exodeoxyribonuclease. Said enzyme may recognize double-stranded nucleic acid molecules, single-stranded nucleic acid molecules, or both. Said enzyme having exonuclease activity may or may not have one or more additional enzymatic activities (e.g. specific or non-specific endonuclease activity). As a non-limiting example, enzymes having exonuclease activity that may be used in the invention include lambda exonuclease, exonuclease I (Exo I), exonuclease III (Exo III), exonuclease T, T5 exonuclease, T7 exonuclease, RecBCD nuclease, Mung bean exonuclease, RNase D, RNase R exoribonuclease I, exoribonuclease II, and the like. Contacting the population of nucleic acid molecules with an enzyme having exonuclease activity causes degradation of non-target nucleic acid regions, thereby specifically enriching the target region. Enzymatic degradation may be partial (i.e. non-protected nucleic acid molecules are present in the population even after being contacted with the enzyme having exonuclease activity) or complete. Thus, the term "degrading" comprises at least partially degrading the nucleic acid molecules that are not comprised in the Type II Cas protein-gRNA-nucleic acid molecule complex.

Thus, according to a preferred embodiment, the method of the invention comprises:

degrading the nucleic acid molecules that are not comprised in the Type II Cas protein-gRNA-nucleic acid molecule complex, preferably by contacting the population of nucleic acid molecules with at least one enzyme having exonuclease activity.

Preferably, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and b) degrading the nucleic acid molecules that are not comprised in the Type II Cas protein-gRNA-nucleic acid molecule complex formed in a), preferably by contacting the population of nucleic acid molecules with at least one enzyme having exonuclease activity.

The skilled person will realize that steps a) and b) in the method above must be performed sequentially, with step a) followed by step b).

According to a preferred embodiment, said enzyme having exonuclease activity does not have endonuclease activity. This may be advantageous when the target region comprises a site that may be recognized by a site-specific endonuclease, or when the target region is susceptible to degradation by a non-specific endonuclease (e.g. said target region comprises a region, such as an adjacent region, that is not directly protected by the Type II Cas protein-gRNA complex). According to a preferred embodiment, said at least one enzyme having exonuclease activity is lambda exonuclease, exonuclease I (Exo I), exonuclease III (Exo III), exonuclease T, T5 exonuclease, T7 exonuclease, RecBCD nuclease, RNase D, RNase R exoribonuclease I, exoribonuclease II, preferably lambda exonuclease or Exo I, more preferably a combination of one or more thereof, even more preferably both lambda exonuclease and Exo I.

According to a preferred embodiment of the invention, nucleic acid molecules may be fragmented before or after being contacted with the Type II Cas protein-gRNA complex, advantageously after being contacted with the Type II Cas protein-gRNA complex. The term "fragmentation" as used herein refers to an increase in the number of nucleic acid molecule 5'- and 3'-free ends by breaking a nucleic acid molecule into at least two smaller molecules. Indeed, the inventors have found that nucleic acid fragmentation improves the efficiency of exonuclease digestion in the present method, as exonuclease activity can only be initiated from a 5'- and/or a 3'-free end.

The term "free end" as used herein refers to the end of a nucleic acid molecule, which may comprise a phosphate group on the 5' end and/or a hydroxyl group on the 3' end.

The free end may be blunt or comprise a single-stranded overhang. Said single-stranded overhang may be a 3' or 5' overhang. Said single-stranded overhang preferably has a length of less than 100, 50, 25, 10, 5, 4, or less than 3 nucleotides.

Fragmentation may be performed by shearing, for example by sonication, hydro-shearing, ultrasound, nebulization or by enzymatic fragmentation, for example by using one or more site-specific endonucleases, such as restriction enzymes. At least 2, 3, 4, 5, or more, site-specific endonucleases may be used. It will be realized that the ever-increasing number of sequences available in the databases enables the skilled person to easily identify one or more restriction enzymes whose cleavage sites are located outside of the nucleic acid target region. Advantageously, said enzymes are compatible to one another (e.g. buffer requirements, inactivation conditions). Fragmentation may be partial (e.g. not all cleavage sites present in the nucleic acid molecules of the population are cut by the restriction enzyme) or complete. Thus, the term "fragmentation" comprises at least partially fragmenting the nucleic acid molecules that are not comprised in the Type II Cas protein-gRNA-nucleic acid molecule complex.

Thus, according to some embodiments, after formation of the Type II Cas protein-gRNA-nucleic acid molecule complex, the method further comprises the step of:

fragmenting the nucleic acid molecules that are not comprised in the Type II Cas protein-gRNA-nucleic acid molecule complex, preferably by contacting the population of nucleic acid molecules with at least one site-specific endonuclease, more preferably with at least one restriction enzyme.

Figure 3A:
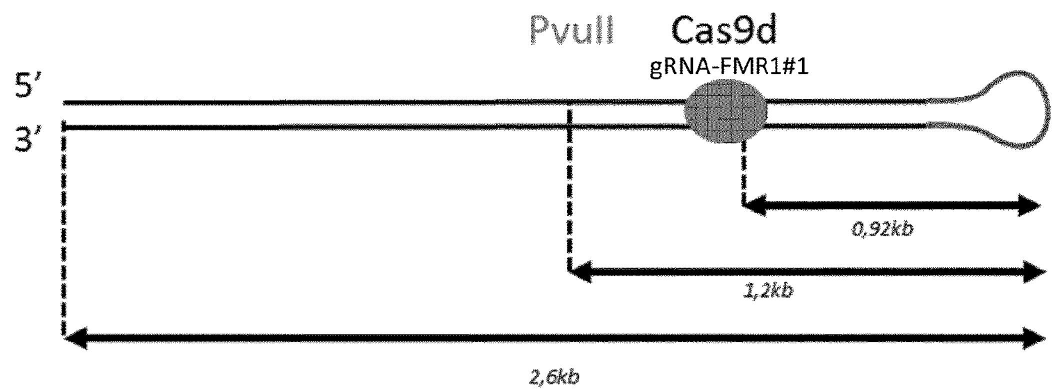

According to a preferred embodiment, nucleic acid molecules are fragmented by contacting the population of nucleic acid molecules with at least one site-specific endonuclease, preferably at least 2, 3, 4, 5, or more, site-specific endonucleases. Preferably, said site-specific endonuclease is a restriction enzyme, more preferably a Type II, Type III, or artificial restriction enzyme, even more preferably a Type II restriction enzyme, and/or the Type II Cas protein Cpf1. Type II restriction enzymes include Type IIP, IIS, IIC, IIT, IIG, IIE, IIF, IIG, IIM, and IIB categories, as described for example in Pingoud and Jeltsch, *Nucleic Acids Res,* 2001, 29(18): 3705-3727. Preferably, one or more enzymes from these categories are used to fragment nucleic acid molecules in the present invention, as can be selected by the skilled person. In cases where multiple restriction enzymes that are not compatible with one another are used, fragmentation may comprise in multiple sequential steps, using different restriction enzymes and conditions (e.g. temperature, time, buffer). Preferably, the at least one restriction enzyme or Cpf1 generates non-palindromic overhangs. Preferably, at least 50%, 60%, 70%, 80%, 90%, 95%, or 100% of cleavage sites are cleaved by the restriction enzyme(s) or Cpf1. In cases where the site-specific endonuclease is the Type II Cas protein Cpf1, said Cpf1 protein is loaded with crRNA recognizing a specific site within a nucleic acid molecule, wherein the PAM is located outside of the target region (as illustrated, for example, FIG. 3A). Two or more Cpf1-gRNA complexes (also referred to interchangeably herein as Cpf1-crRNA complexes) may advantageously be used in combination, each gRNA being complementary to a different nucleic acid sequence. Alternatively, a gRNA may be designed such that it recognizes a sequence that is present at two or more locations within a nucleic acid molecule. Preferably, when two or more target regions are isolated, a Cpf1-gRNA complex acting as a site-specific endonuclease may specifically bind near each of said target regions. This is highly advantageous, as the number of free ends is limited, thereby reducing non-specific binding by the Type II Cas protein-gRNA complex. As a non-limiting example, a Cpf1-gRNA complex acting as a site-specific endonuclease may bind a sequence that is located 100 to 5000 bases from a target region, more preferably 150 to 1000 bases from a target region, even more preferably 250-750 bases from a target region. As a non-limiting example, the Cpf1-gRNA complex acting as a site-specific endonuclease may target a sequence that is present multiple times within the nucleic acid molecule(s), such as the Alu element in the human genome.

According to an even more preferred embodiment, the Type II Cas protein-gRNA-nucleic acid molecule complex is simultaneously contacted with at least one enzyme having exonuclease activity and at least one site-specific endonuclease. This is particularly advantageous, as it reduces the duration of the method. According to another preferred embodiment, said enzyme having exonuclease activity may also have site-specific endonuclease activity. According to this embodiment, the cleavage site(s) of the enzyme having site-specific endonuclease activity is/are located outside of the target region. The use of a single enzyme having both exonuclease and site-specific endonuclease activity is particularly advantageous as it reduces the number of reagents required and cost.

Thus, according to a particular embodiment, the method comprises the steps of:

a) contacting the population of nucleic acid molecules with at least one Type II Cas protein-gRNA complex, wherein said gRNA comprises a guide segment that is complementary to a sequence comprised in the target region of at least one nucleic acid molecule, and
b) fragmenting the nucleic acid molecules that are not comprised in the Type II Cas protein-gRNA-nucleic acid molecule complex formed in a), preferably by contacting the population of nucleic acid molecules with at least one site-specific endonuclease, more preferably with at least one restriction enzyme, and
c) degrading the nucleic acid molecules that are not comprised in the Type II Cas protein-gRNA-nucleic acid molecule complex formed in a), preferably by contacting the population of nucleic acid molecules with at least one enzyme having exonuclease activity.

Preferably, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and
b) contacting the population of nucleic acid molecules with at least one site-specific endonuclease, preferably a restriction enzyme, and
c) contacting the population of nucleic acid molecules with at least one enzyme having exonuclease activity.

As a particular example, the method may comprise the steps of:

a) contacting a population of nucleic acid molecules with at least one Type II Cas protein-gRNA complex, wherein said gRNA comprises a guide segment that is complementary to a sequence comprised in the target region of at least one nucleic acid molecule,
b) contacting the population of nucleic acid molecules with at least one Cpf1-gRNA complex, wherein said gRNA comprises a guide segment that is complementary to a sequence comprised outside of the target region of at least one nucleic acid molecule and wherein the PAM is located outside of the target region, said Cpf1-gRNA complex thereby fragmenting said nucleic acid, and
c) contacting the population of nucleic acid molecules with at least one enzyme having exonuclease activity.

Figure 9A:
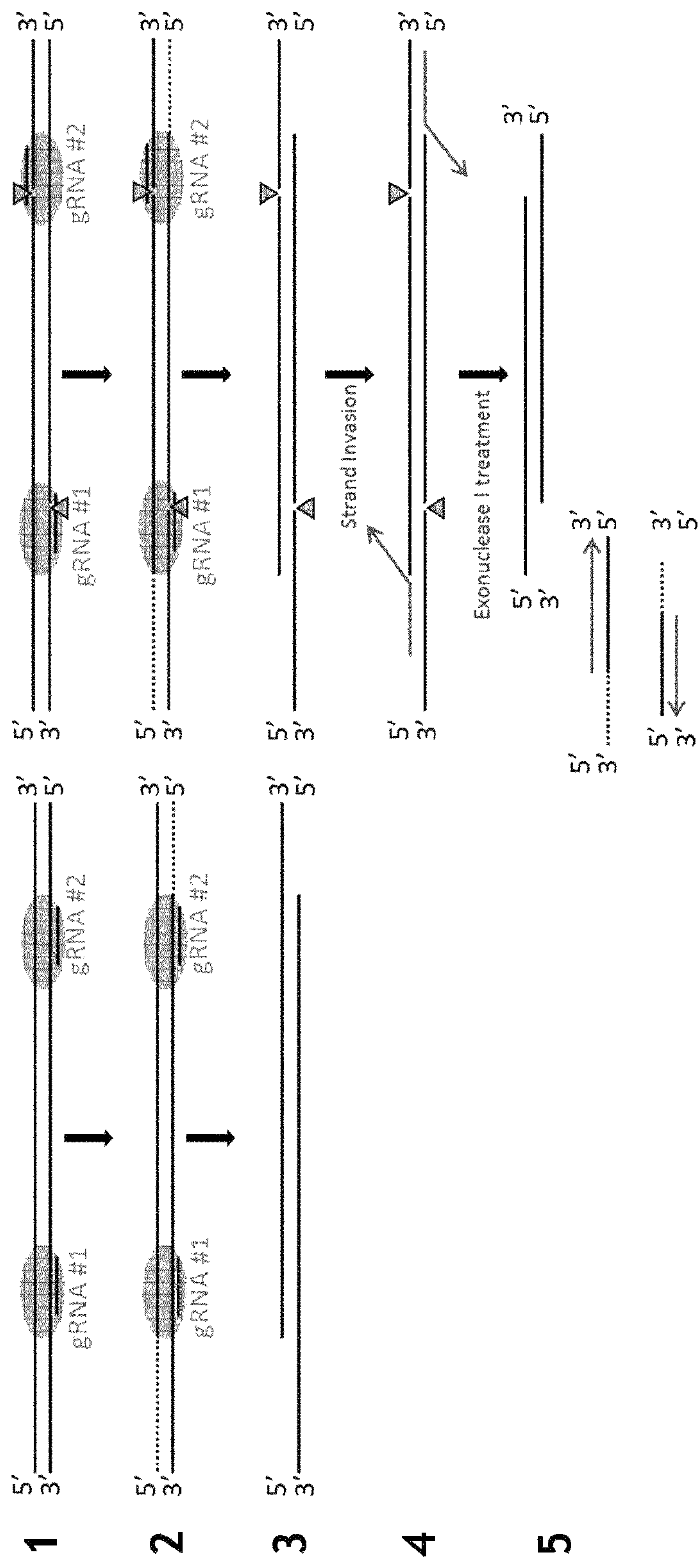
Figure 9B:
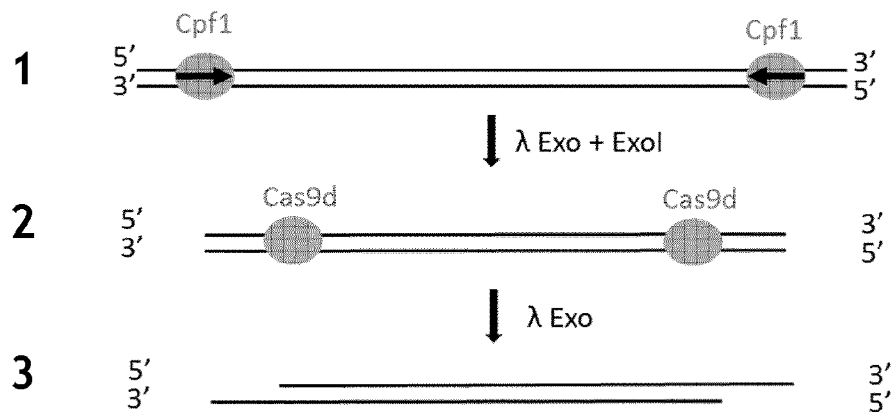
Figure 9C:
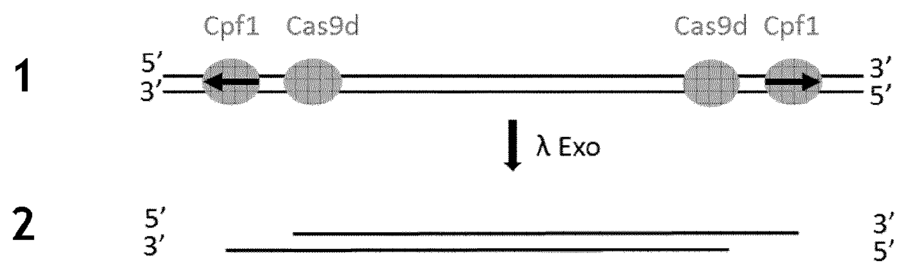

When the at least one Type II Cas protein-gRNA complex of step a) is a Cpf1-gRNA complex, the PAM is located within the target region (cf. as an example FIG. 9C, wherein Cpf1 is substituted for dCas9). Preferably, said Type II Cas protein of step a) is a nickase or catalytically inactive Type II Cas protein, even more preferably a catalytically inactive Type II Cas protein (e.g. catalytically inactive Cpf1). Said at least one Cpf1-gRNA complex of step a) protects said target region when the PAM is located within the target region, whereas the at least one Cpf1-gRNA complex of step b) acts as a site-specific endonuclease.

The skilled person will realize that steps b) and c) of the methods above need not be performed sequentially. Preferably, step b) is performed before step c), or steps b) and c) are performed simultaneously. The skilled person will further realize that step b) is optional. The skilled person will further realize that the steps of fragmentation and degradation may be incomplete (e.g. partial) or complete. The skilled person will further realize that when at least one Cpf1-gRNA complex is used in step b), step b) may be performed prior to step a), simultaneously with step a), or after step a). Preferably, when at least one Cpf1-gRNA complex is used in step b), step b) is performed prior to step a), simultaneously with step a), or after step a). When step b) is performed simultaneously or prior to step a), step c) is performed sequentially after said step(s) to ensure that the target region is protected from exonuclease activity prior to contacting the population of nucleic acid molecules with said at least one enzyme having exonuclease activity.

In cases where the population of nucleic acid molecules comprises one or more molecules that are not linear, said molecule(s) must be linearized prior to contacting the population of nucleic acid molecules with the at least one enzyme having exonuclease activity as described in step c) of the embodiments above. The term "linearization" as used herein refers to the transformation of a circular nucleic acid molecule into a linear nucleic acid molecule. Indeed, exonuclease activity is dependent on the presence of 5' and/or 3' free ends in the nucleic acid molecule. Linearization is necessary when a nucleic acid sample comprises or consists of circular nucleic acid molecules, such as covalently closed circular DNA and/or circular RNA, including plasmids, cpDNA, mtDNA, and/or circular chromosomes or genomes. Nucleic acid molecules within the population may be linearized prior to, simultaneously to, or after being contacted with at least one Type II Cas protein-gRNA complex according to step a) of the embodiments above. As a non-limiting example, a nucleic acid molecule may be linearized by contacting said molecule with one or more site-specific endonucleases, such as a restriction enzyme. Linearization may be partial (i.e. circular nucleic acid molecules are present in the population after being contacted with the enzyme having exonuclease activity) or complete, preferably complete. Thus, the term "linearizing" comprises at least partially linearizing the nucleic acid molecules that are not comprised in the Type II Cas protein-gRNA-nucleic acid molecule complex. Preferably, at least 50%, 60%, 70%, 80%, 90%, 95%, or 100% of circular nucleic acid molecules are linearized.

When a nucleic acid molecule is linearized by contacting said molecule with a site-specific endonuclease, preferably, preferably only a single site-specific endonuclease is used. Preferably, said site-specific endonuclease recognizes a limited number sites, preferably less than 10, 9, 8, 7, 6, 5, 4, 3, or 2 sites, even more preferably said site-specific endonuclease recognizes only a single site within the nucleic acid molecule. Indeed, the inventors have surprisingly found that the Type II Cas protein-gRNA complex may non-specifically bind to nucleic acid molecule free ends in some conditions, which can lead to non-specific isolation of nucleic acid molecules and/or reduced isolation efficiency. The skilled person will easily be able to identify an appropriate site-specific endonuclease for linearization by determining the number of sites said site-specific endonuclease will recognize according to the known sequence of the nucleic acid molecule and using methods well-known in the prior art. In some cases, for example when a very large nucleic acid molecule or complex mixture comprising multiple circular nucleic acid molecules are linearized, it may not be possible to identify a site-specific endonuclease that will cleave only at a single site, or even a single site-specific endonuclease that will cleave all nucleic acid molecules. In this case, the skilled person can easily identify one or more site-specific endonucleases that will cleave all nucleic acid molecules while limiting the number of cleavage sites. As a particular example, the site-specific endonuclease could be directed to a repeated element, such as the Alu element, which represents approximately 10% of the human genome. As a non-limiting example, a recombinant site-specific nuclease, such as a Cas9 protein, could be engineered that cleaves a specific site, but that does not protect the target region after cleavage.

Thus, according to a particular aspect of the invention, the method comprises the steps of:

a) linearizing a population of nucleic acid molecules, preferably by contacting said population of nucleic acid molecules with at least one site-specific endonuclease, more preferably with at least one restriction enzyme,
b) contacting the population of nucleic acid molecules with at least one Type II Cas protein-gRNA complex, wherein said gRNA comprises a guide segment that is complementary to a sequence comprised in the target region of at least one nucleic acid molecule,
c) fragmenting said population of nucleic acid molecules, preferably by contacting said population of nucleic acid molecules with at least one site-specific endonuclease, more preferably with at least one restriction enzyme, and
d) degrading the nucleic acid molecules that are not comprised in the Type II Cas protein-gRNA-nucleic acid molecule complex formed in a), preferably by contacting the population of nucleic acid molecules with at least one enzyme having exonuclease activity.

More preferably, the method comprises the steps of:

a) contacting a population of nucleic acid molecules with at least one site-specific endonuclease, preferably with at least one restriction enzyme
b) contacting said population of nucleic acid molecules with at least one Type II Cas protein-gRNA complex, wherein said gRNA comprises a guide segment that is complementary to a sequence comprised in the target region of at least one nucleic acid molecule, and
c) contacting said population of nucleic acid molecules with at least one site-specific endonuclease, preferably a restriction enzyme,
d) contacting said population of nucleic acid molecules with at least one enzyme having exonuclease activity.

The skilled person will realize that steps b) and d) of the above methods must be performed sequentially. The skilled person will also realize that step a) may be performed in any particular order, as long as it is prior to or simultaneously with step d), including before, after, or simultaneously with step b) and/or step c), or simultaneously with step d). The skilled person will further realize that when steps a) and c) are performed simultaneously, linearization and fragmentation may be performed using the same one or more site-specific endonucleases. This is particularly advantageous as the number of reagents, cost, and duration of the method may be reduced. The skilled person will further realize that step a) is necessary only when isolating a target region from a population comprising at least one circular nucleic acid molecule. The skilled person will further realize that step c) is optional. Finally, the skilled person will realize that steps a), c), and d) of the above methods may be performed simultaneously.

According to a preferred embodiment, linearization comprises contacting the population of nucleic acid molecules with a site-specific endonuclease, such as a restriction enzyme. Preferably, a single site-specific endonuclease is used. Preferably, said site-specific endonuclease cleaves only a single site in the circular nucleic acid molecule. This is particularly advantageous when linearization is performed as a first step or simultaneously with step b) of the embodiments above, given that the Type II Cas protein-gRNA complex has an increased tendency to bind non-specifically near the free ends of nucleic acid molecules in some conditions. According to an alternative preferred embodiment, a restriction enzyme that is a rare cutter (e.g. recognizing at least an 8-nucleotide site, such as NotI) may be used. Preferably, the site recognized by the site-specific endonuclease for linearization is located outside of the target region recognized by the Type II Cas protein-gRNA complex.

According to a particularly preferred embodiment, when nucleic acid molecules are linear, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and b) contacting the population of nucleic acid molecules with at least one site-specific endonuclease, preferably a restriction enzyme, and at least one enzyme having exonuclease activity.

The skilled person will understand that step b) must be performed after step a).

The Type II Cas protein-gRNA complex stably and tightly binds to a nucleic acid target region to form the Type II Cas protein-gRNA-nucleic acid molecule complex. As this binding may prevent the target region from interacting with other compounds (e.g. proteins, polypeptides, nucleic acid molecules), it is preferable to separate the nucleic acid molecule target region from the Type II Cas protein-gRNA-nucleic acid molecule complex after enrichment for downstream analyses. It is particularly advantageous to remove the Type II Cas protein-gRNA complex. As a non-limiting example, the target region may be isolated from the Type II Cas protein-gRNA-nucleic acid complex by contacting the Type II Cas protein-gRNA-nucleic acid molecule complex with at least one protease. This degrades the Type II Cas protein. As a non-limiting example, the protease may be selected from serine proteases, cysteine proteases, threonine proteases, aspartic proteases, glutamic proteases, metalloproteases, and/or asparagine peptide lyases. As a non-limiting example, the target region is isolated from the Type II Cas protein-gRNA-nucleic acid complex by contacting the Type II Cas protein-gRNA-nucleic acid molecule complex with at least one RNase, such as RNaseA, RNase H, or RNase I. This degrades the gRNA. In another example, as RNA is unstable at elevated temperatures, the sample may be heated (e.g. to at least 65° C.), optionally in the presence of divalent metal ions and/or under alkaline pH. As an alternative example, the target region may be isolated from the Type II Cas protein-gRNA-nucleic acid complex by contacting the Type II Cas protein-gRNA-nucleic acid complex with a compound capable of chelating divalent cations (in particular Mg2+), such as EDTA or EGTA. In some cases, the Type II Cas protein-gRNA-nucleic acid molecule complex may be contacted with both a protease and a divalent cation chelator such as EDTA.

Thus, according to a particular embodiment, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, b) degrading the nucleic acid molecules that are not comprised in the Type II Cas protein-gRNA-nucleic acid molecule complex formed in a), preferably by contacting said population of nucleic acid molecules with at least one enzyme having exonuclease activity, and c) isolating said target region from the Type II Cas protein-gRNA-nucleic acid molecule complex formed in a).

According to a more specific embodiment, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and b) contacting the population of nucleic acid molecules with at least one enzyme having exonuclease activity, and c) isolating said target region from the Type II Cas protein-gRNA-nucleic acid molecule complex formed in a).

The skilled person will understand that steps a), b), and c), of the above embodiments must be performed sequentially in the order as shown. The above embodiments may further comprise steps of linearization and/or fragmentation as described herein, for example by contacting the population of nucleic acid molecules with one or more site-specific endonucleases, preferably a restriction enzyme, according to any order previously described herein.

According to a preferred embodiment, isolation of said target region is performed by contacting the Type II Cas protein-gRNA-nucleic acid molecule complex with at least one protease, preferably at least one serine protease, cysteine protease, threonine protease, aspartic protease, glutamic protease, metalloprotease, and/or an asparagine peptide lyase. Even more preferably, said at least one protease comprises proteinase K. According to an alternative embodiment, isolation of said target region is performed by contacting the Type II Cas protein-gRNA-nucleic acid molecule complex with a protease, preferably a serine protease, even more preferably proteinase K.

According to a preferred embodiment, isolation of said target region is performed by contacting the Type II Cas protein-gRNA-nucleic acid molecule complex with at least one RNase, preferably RNaseA, RNase H, or RNase I, even more preferably RNaseA. The skilled person will understand that when the nucleic acid target region comprises an RNA molecule, RNase treatment is preferably not comprised in the present method.

According to a preferred embodiment, isolation of said target region is performed by contacting the Type II Cas protein-gRNA-nucleic acid molecule complex simultaneously with at least one protease and at least one RNase. According to an alternative preferred embodiment, isolation of said target region is performed by contacting the Type II Cas protein-gRNA-nucleic acid molecule complex sequentially with at least one protease and at least one RNase, preferably wherein said complex is first contacted with the at least one protease followed by the at least one RNase.

Thus, according to a more preferred embodiment, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and b) contacting the population of nucleic acid molecules with at least one enzyme having exonuclease activity, and c) isolating said target region from the Type II Cas protein-gRNA-nucleic acid molecule complex formed in a), preferably by contacting the Type II Cas protein-gRNA-nucleic acid molecule complex with at least one protease and/or at least one RNase.

According to a preferred embodiment, isolation of said target region is performed by contacting the Type II Cas protein-gRNA-nucleic acid molecule complex with a chelator of divalent cations, preferably a chelator chelating Mg2+ cations. Preferably, said chelator is EDTA or EGTA. Preferably, the quantity of EDTA or EGTA added is at least 2-fold greater than the quantity of divalent cations to be chelated, more preferably at least 3-fold, 4-fold, 5-fold greater, even more preferably at least 10-fold greater than the quantity of divalent cations. The skilled person can easily determine the appropriate quantity of chelator in view of the composition of the solution comprising the population of nucleic acid molecules (e.g. according to the presence and quantity of cations), and in further view of the quantities provided herein. According to a particular example, EDTA is added at a concentration of at least 20 mM, more preferably at least 25 mM. In cases where at least one protease and a chelator of divalent cations are used in step c), said at least one protease and said chelator of divalent cations may be added simultaneously wherein said chelator does not inhibit activity of said at least one protease.

Thus, according to a more preferred embodiment, the method comprises the steps of:

a) contacting a population of nucleic acid molecules with at least one Type II Cas protein-gRNA complex, wherein said gRNA comprises a guide segment that is complementary to a sequence comprised in the target region of at least one nucleic acid molecule, and
b) contacting the population of nucleic acid molecules with at least one enzyme having exonuclease activity, and
c) isolating said target region from the Type II Cas protein-gRNA-nucleic acid molecule complex formed in a), preferably by contacting the Type II Cas protein-gRNA-nucleic acid molecule complex with EDTA.

The inventors have further found that the ratio of the nucleic acid target region to Type II Cas protein to gRNA (nucleic acid target region:Type II Cas protein:gRNA) influences the efficiency of target region isolation. The ratio of the nucleic acid target region to Type II Cas protein to gRNA may notably be optimized according to the target sequence and/or the origin and/or the complexity of the population of nucleic acid molecules. Without being limited by theory, optimization may particularly depend on DNA complexity (e.g. less complex nucleic acid populations may essentially comprise repeating sequences or PCR amplified fragments, whereas more complex nucleic acid populations may notably correspond to genomic DNA), with more complex nucleic acid populations requiring higher quantities of Type II Cas protein and gRNA with respect to a single nucleic acid target region. As a non-limiting example, a ratio of 1:10:20 allows isolation of a target region from a population of nucleic acid molecules generated by PCR, a ratio of 1:1600:3200 has been shown to successfully isolate a target region from *E. coli* genomic DNA, and a ratio of 1:100000:200000 has been shown to successfully isolate a target region from human genomic DNA. In cases where multiple gRNAs are used to isolate a single target nucleic acids (e.g. wherein two gRNAs recognize two regions flanking a central adjacent region, or wherein nested Type II Cas protein:gRNA complexes are used), a single optimized ratio of the nucleic acid target region to Type II Cas protein to gRNA may be selected for all gRNA. In cases where multiple target nucleic acids are isolated simultaneously, a single optimized ratio of the nucleic acid target region to Type II Cas protein to gRNA may be selected for all gRNA. Alternatively, an optimized ratio may be selected for each gRNA individually.

According to a preferred embodiment, the ratio of the nucleic acid target region to Type II Cas protein to gRNA is at least 1:10:10, more preferably at least 1:10:20, even more preferably at least 1:10:50. A ratio of at least 1:10:20 is particularly preferred when template DNA is provided from PCR. Preferably, guide RNAs are selected for efficiency using a PCR template, followed by optimization of the ratio of nucleic acid target region:Type II Cas protein:gRNA on appropriate template, if necessary. Preferably, cleavage efficiency of a wild type Type II Cas protein-gRNA complex is at least 70%, more preferably at least 80%, even more preferably at least 90%. Preferably, the efficiency of protection of a target region by a Type II Cas protein-gRNA complex is at least 70%, more preferably at least 80%, even more preferably at least 90%. Preferably, the ratio of the nucleic acid target region:Type II Cas protein:gRNA is at least 1:200:400, more preferably at least 1:400:800, even more preferably at least 1:800:1600, at least 1:1600:3200, or at least 1:3200:6400 when the nucleic acid target DNA is isolated from nucleic acids of bacterial origin, such as gram-negative bacteria, such as *E. coli*. According to an alternative preferred embodiment, the ratio of the nucleic acid target region to Type II Cas protein to gRNA is at least 1:10,000:20,000, more preferably at least 1:100,000:200,000. The skilled person can easily adapt the ratio of the nucleic acid target region to Type II Cas protein to gRNA according to the target region and/or the origin and/or complexity of nucleic acid molecules in view of the ratios provided above and the specific examples provided herein. While the proportion of Type II Cas protein to gRNA may vary, the gRNA is advantageously provided in at least two-fold excess to the Type II Cas protein to ensure that Type II Cas protein is successfully loaded with gRNA. Higher ratios of Type II Cas9 protein (e.g. for a PCR target, 1:20:40, 1:50:100, etc.) and, optionally, of gRNA (e.g. for a PCR target, 1:10:30, 1:10:40, etc.) may of course be used.

According to a preferred embodiment, the present method isolates the target nucleic acid region with at least 60%, more preferably at least 65%, at least 70%, at least 75%, at least 80%, at least 85%, at least 90%, even more preferably at least 95% efficiency.

According to another aspect of the invention, the target region is not limited to the nucleic acid region that forms a complex with the Type II Cas protein-gRNA complex, but may further comprise additional adjacent nucleic acid regions. Indeed, the present method is particularly suitable for enriching longer nucleic acid molecules fragments (e.g. greater than the at least 44 nucleotide region that directly binds with, and/or is directly shielded by, the Type II Cas protein-gRNA complex).

According to this particular aspect of the invention, the method comprises an additional step of contacting the population of nucleic acid molecules with at least one protector molecule. The term “protector molecule” as used herein refers to any type of molecule that can prevent nucleic acid degradation for example, by an enzyme having exonuclease activity. More specifically, the protector molecule is any molecule that prevents the adjacent nucleic acid region from being degraded, for example, by an enzyme having exonuclease activity. Preferably, the adjacent region is a region that does not directly hybridize with the Type II Cas protein-gRNA complex. The protector molecule may directly bind to the nucleic acid molecule. The protector molecule may block the access of the exonuclease to the 5' or 3' free end of a nucleic acid molecule, or halt exonuclease progression by blocking one or more sites within the nucleic acid molecule. The protector molecule may bind to a free-end of a nucleic acid molecule or within a nucleic acid molecule. As a non-limiting example, the protector molecule may be a nucleic acid and/or protein molecule. As an example, the protector molecule may be an oligonucleotide comprising at least one modified base that cannot be degraded by the enzyme having exonuclease activity, such as a phosphorothiolated base. Alternatively, the protector molecule may be a hairpin adaptor, or a site-specific endonuclease that tightly and stably binds to the nucleic acid molecule, such as a second Type II Cas protein-gRNA complex, a TALEN, or a zinc-finger protein. When using a hairpin adaptor, said adaptor is ligated to any one free end of the nucleic acid molecule comprising the target region. Preferably, the free end comprises an overhang. Preferably, said hairpin also comprises an overhang that is at least partially complementary to that of the overhang of the nucleic acid molecule comprising the target region. Preferably, said adjacent nucleic acid region is located between the Type II Cas protein-gRNA-nucleic acid molecule complex and the protector molecule.

When using a site-specific endonuclease, such as a second Type II Cas protein-gRNA complex, said compound preferably forms a second complex within the nucleic acid molecule comprising the target region.

The term "adjacent region" as used throughout the present application refers to a nucleotide region that directly abuts the target region that is bound by the Type II Cas protein-gRNA complex. Together said target region bound by the Type II Cas protein-gRNA complex and said adjacent region form an uninterrupted nucleotide polymer. The adjacent region may be on either of the two sides of the target region. Preferably, the adjacent region is located either 3' or 5' of the PAM. Alternatively, an adjacent region is located on both sides of the PAM (e.g. when multiple Type II Cas protein-gRNA complexes bind to the nucleotide molecule). As an example, the non-hybridized strand of the nucleic acid molecule comprising the PAM may comprise: 5'-(N)x-target region corresponding to the gRNA-PAM-(N)x-3', wherein (N)x represents any number of any nucleotide and wherein the "target region corresponding to the gRNA" is at least partially homologous to the gRNA. The adjacent region in this case is preferably located 3' of the PAM. According to a preferred embodiment, the adjacent region is located 3' of the PAM when the Type II Cas protein is Cas9. Alternatively, the non-hybridized strand of the nucleic acid molecule comprising the PAM may comprise: 5'-(N)x-PAM-target region corresponding to the gRNA-(N)x-3', wherein (N)x represents any number of any nucleotide and wherein the "target region corresponding to the gRNA" is at least partially homologous to the gRNA. The adjacent region in this case is preferably located 5' of the PAM. According to a preferred embodiment, the adjacent region is located 5' of the PAM when the Type II Cas protein is Cpf1. The target nucleic acid region can comprise adjacent nucleic acid regions having a length of at least 50, 100, 250, 500, 1,000, 5,000, 10,000, 20,000, 30,000, 40,000, 50,000, 60,000, 70,000, 80,000, 90,000, 100,000, 200,000, 500,000, 750,000 or 1,000,000 nucleotides.

The term "hairpin" or "hairpin adaptor" as used herein refers to a molecule that base pairs with itself to form a structure having a double-stranded stem and a loop. The "loop" as used herein refers to a succession of nucleotides of a nucleic acid strand that are not paired through hydrogen bonds with nucleotides of the same or another strand of said nucleic acid. The "stem" as used herein refers to a region of intra-strand pairing. Preferably, the stem comprises at least 1, 2, 5, 10, or 20 base pairs, more preferably at least 5, 10, or 20 base pairs, even more preferably at least 10 or 20 base pairs. When the hairpin binds to the free end of a double-stranded nucleic acid molecule, the 3' and 5' ends of the hairpin ligate to the 5' and 3' ends of the double-stranded nucleic acid molecule, respectively. Preferably, said hairpin adaptor binds to any one of the free ends, preferably only one of the free ends, of the nucleic acid molecule. Said hairpin adaptor may specifically bind to one of the free ends of a nucleic acid molecule. As a non-limiting example, specific binding may be performed by fragmenting the nucleic acid molecule(s) with a non-palindromic restriction enzyme, thereby generating different overhangs at each new free end of the nucleic acid molecule.

When the protector molecule is a hairpin adaptor, said protector molecule binds to any one of the free ends, preferably only one of the free ends, of the nucleic acid molecule. Alternatively, when the protector molecule is a second site-specific endonuclease, such as a second Type II Cas protein-gRNA complex, a TALEN, or a zinc-finger protein, preferably said protector molecule binds within a nucleic acid molecule or to a free end, more preferably within the nucleic acid molecule. Two particular examples are provided in FIGS. 7A and 9A, respectively. Said protector molecule may bind to a target region located at a distance from the target region of the Type II Cas protein-gRNA complex. Said protector molecule must bind to the same uninterrupted nucleotide polymer.

Preferably, when the protector molecule is a second site-specific endonuclease, such as a Type II Cas protein-gRNA complex, the target nucleic acid regions that hybridize with the Type II Cas protein-gRNA complex are separated from one another by at least 15, 25, 50, 100, 250, 500, 1,000, 5,000, 10,000, 25,000, 50,000, 75,000, 100,000, 150,000, 200,000, 500,000, 750,000 or at least 1,000,000 nucleotides or base pairs. In particular, the protector molecule may prevent degradation of the "adjacent region" located between the two Type II Cas protein-gRNA-nucleic acid molecule complexes. Contacting the population of nucleic acid molecules with a protector molecule may be performed prior to, simultaneously, or after, contacting the population of nucleic acid molecules with the at least one Type II Cas protein-gRNA complex.

In view of the above, a preferred embodiment of the method further comprises the step of:

protecting a target region comprising an adjacent region.

Thus, according to one aspect of the invention, the method comprises the steps of:

a) linearizing a population of nucleic acid molecules, preferably by contacting the population of nucleic acid molecules with at least one site-specific endonuclease, more preferably with at least one restriction enzyme,
b) contacting the population of nucleic acid molecules with at least one Type II Cas protein-gRNA complex, wherein said gRNA comprises a guide segment that is complementary to a sequence comprised in the target region of at least one nucleic acid molecule,
c) protecting a target region comprising an adjacent region,
d) fragmenting the nucleic acid molecules that are not comprised in the Type II Cas protein-gRNA-nucleic acid molecule complex formed in b), preferably by contacting the population of nucleic acid molecules with at least one site-specific endonuclease, more preferably with at least one restriction enzyme,
e) degrading the nucleic acid molecules that are not comprised Type II Cas protein-gRNA-nucleic acid molecule complex formed in b), preferably by contacting the population of nucleic acid molecules with at least one enzyme having exonuclease activity. and
f) isolating said target region from the Type II Cas protein-gRNA-nucleic acid molecule complex formed in b), preferably by contacting said complex with at least one protease and/or at least one RNase, and/or by contacting said complex with EDTA.

Preferably, step c) of the method above comprises contacting the population of nucleic acid molecules with at least one protector molecule.

The skilled person will realize that steps b) and c) of the method above may be performed in any particular order, as long as they are performed prior to step e). Indeed, step b) may be performed before step c), step c) may be performed before step b), or both steps may be performed simultaneously. The skilled person will further realize that step e) and step f) must be performed sequentially. The skilled person will further realize that steps a), c), and d) are optional and may be performed in any of the orders described in previous embodiments herein. Indeed, the skilled person will particularly realize that step a) is necessary only when the population of nucleic acid molecules comprises circular nucleic acid molecules.

According to a preferred embodiment, the method comprises at least the steps of:

a) contacting a population of nucleic acid molecules with at least one Type II Cas protein-gRNA complex, wherein said gRNA comprises a guide segment that is complementary to the sequence comprised in the target region of at least one nucleic acid molecule, b) contacting the population of nucleic acid molecules with at least one protector molecule, c) contacting the population of nucleic acid molecules with at least one enzyme having exonuclease activity, and optionally at least one site-specific endonuclease, and d) isolating said target region from the Type II Cas protein-gRNA-nucleic acid molecule complex formed in a).

The skilled person will realize that steps a) and b) of the method above may be performed in any particular order, as long as they are performed prior to step c). Indeed, step a) may be performed before step b), step b) may be performed before step a), or both steps may be performed simultaneously. The skilled person will further realize that step c) and step d) must then be performed sequentially. The skilled person will further realize that the above embodiment may further comprise steps of linearization and/or fragmentation, as detailed in any of the previous embodiments above, or as otherwise specified herein. The skilled person will further realize that step b) is optional.

Preferably, the protector molecule is a hairpin adaptor or a site-specific endonuclease, more preferably a second Type II Cas protein-gRNA complex. According to a preferred embodiment, the Type II Cas protein-gRNA-nucleic acid complex is separated from the protector molecule by at least 15 nucleotides, preferably at least 20, 50, 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides. Thus, according to a preferred embodiment, the target region comprising the adjacent nucleic acid region has a length of at least 50, 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides.

In one embodiment of the method of the invention, the protector molecule binds to a free end of the nucleic acid molecule comprising the target region. Thus, according to a preferred embodiment, step b) comprises contacting the population of nucleic acid molecules with a hairpin adaptor. Preferably, said hairpin adaptor is linked to the nucleic acid molecule, preferably ligated to the nucleic acid molecule. More preferably, step b) comprises contacting the population of nucleic acids with a hairpin adaptor and linking said hairpin adaptor to a nucleic acid molecule free end. In this preferred embodiment, the method further comprises a step of linearizing the nucleic acid molecule prior to contacting the population of nucleic acids with a hairpin adaptor, as described herein, if necessary (e.g. when the sample comprises circular nucleic acid molecules).

According to an alternative preferred embodiment, step b) comprises contacting the population of nucleic acid molecules with a second site-specific endonuclease, preferably a second Type II Cas protein-gRNA complex, a TALEN, or a zinc-finger protein, even more preferably a second Type II Cas protein-gRNA complex. When the protector molecule is a Type II Cas protein-gRNA complex, it is particularly preferred that steps a) and b) of the above embodiment be performed simultaneously. This is advantageous as the duration of the method is reduced. As a particular example, nested Type II Cas protein-gRNA complexes may be used (see for example, the illustration in FIG. 9B, schema 1). Preferably, said protector molecule consists in at least one Cpf1-gRNA complex, more preferably two or more Cpf1-gRNA complexes, wherein the PAM site is comprised within the target region. According to a particular embodiment, two dCas9-gRNA complexes flank a central adjacent target region, and are themselves nested within a region bound by two Type II Cas protein-gRNA complexes, preferably two Cpf1-gRNA complexes wherein the PAM site is comprised within the region to be protected. This is particularly advantageous as 3' overhangs may be generated by the Cpf1-gRNA complexes or by two other Type II Cas9 protein-gRNA complexes. If circular nucleic acid molecules are present in the sample, linearization is preferably performed before, or simultaneously with, the degradation of nucleic acid molecules that are not comprised in the Type II Cas protein-gRNA-nucleic acid molecule complex.

According to a preferred embodiment, when multiple target regions are isolated, step b) may comprise contacting the population of nucleic acid molecules with more than one protector molecules. In one preferred embodiment, the more than one protector molecules comprise a combination of protector molecules, preferably comprising both hairpin adaptors and site-specific endonucleases, such as a second Type II Cas protein-gRNA complex.

According to a more preferred embodiment of any of the previously described methods, said one enzyme having exonuclease activity does not have non-specific endonuclease activity. According to another more preferred embodiment, said one enzyme having exonuclease activity of step c) does not have specific endonuclease activity that targets the adjacent region. According to a more preferred embodiment of any of the previously described methods, said enzyme having exonuclease activity does not have non-specific or specific endonuclease activity. This absence of non-specific and/or specific endonuclease activity advantageously prevents digestion of the adjacent nucleic acid region, allowing isolation of the target region comprising the adjacent region.

Preferably, multiple Type II Cas protein-gRNA complexes and/or protector molecules may be used in any of the above embodiments. Indeed, according to a particularly preferred embodiment, two or more Type II Cas protein-gRNA complexes may be used in combination with one or more protector molecules to protect target regions comprising adjacent regions. According to a more preferred embodiment, two, three, four, or more Type II Cas protein-gRNA complexes recognize target regions that are separated from one another by less than 100,000, 50,000, 20,000, 10,000, 5000, 3000, 2000, 1000, 750, 500, 300, 200, 100, or 50 nucleotides, more preferably less than 100 or 50 nucleotides. According to a more preferred embodiment, when the protector molecule is also a Type II Cas protein-gRNA complex, two, three, four or more protector molecules are used, preferably wherein said Type II Cas protein-gRNA complexes recognize target regions that are separated from one another by less than 1000, 750, 500, 300, 200, 100, or 50 nucleotides, more preferably less than 100 or 50 nucleotides. Exemplary embodiments are shown in FIG. 1 and FIG. 9.

According to a preferred embodiment of any of the previously described methods of the invention, all steps are performed in the same container.

Isolated nucleic acids are particularly useful in a wide range of applications. Indeed, the nucleic acids isolated according to the present invention may be used in further processing, reactions, or analysis, which may occur in the same container, or not. As an example, the nucleic acids isolated according to the present invention may be used for detection, cloning, sequencing, amplification, hybridization, cDNA synthesis, and any other methods known to the skilled person which require nucleic acids.

The present method is particularly suited for generating a library of hairpins following isolation of the one or more target regions, wherein each hairpin comprises at least one nucleic acid target region, and optionally, an adjacent region. This method is thus particularly convenient for detecting the sequence of a target region of interest, e.g. a particular allele, isolated from an entire population of nucleic acid molecules, for example in a biological sample.

According to a preferred aspect of the invention, the method of the invention may further comprise additional steps. As a non-limiting example, the isolated nucleic acids may be further purified using well-known purification methods (e.g. bead or column purification) to remove proteins and salts, such as the Type II Cas protein, proteases, EDTA, etc. As a non-limiting example, nucleic acid molecules may be hybridized and/or ligated to the target region, single-stranded gaps in the nucleic acid molecule may be filled in by synthesis of the complementary strand, and/or strand displacement may be performed. These additional steps are particularly useful for generating a hairpin library, but may also be necessary when preparing the isolated nucleic acid for other downstream applications. In a particular example, when one or more double-stranded nucleic acid molecules are isolated according to the methods of the present invention, a hairpin molecule, as has been previously defined herein, may then then be ligated to one or both free ends of said molecule. Preferably, a hairpin is ligated to one free end of the isolated target nucleic acid molecule. Preferably, at least one free end of said isolated target nucleic acid molecule comprises a 3' or 5' overhang. Preferably, said hairpin comprises a 3' or 5' overhang that is at least partially complementary to at least one of the 5' or 3' overhangs, respectively, of said isolated target nucleic acid molecule. Preferably, said hairpin is ligated to a 3' overhang on one end of the isolated target nucleic acid molecule, as is as illustrated for example in FIG. 9D or 9E (middle panel). As an alternative example, the hairpin is advantageously ligated to the 3' overhang in presence of the FEN1 enzyme, which cleaves 5'DNA flaps. Indeed, the inventors have found that ligating the hairpin to a 3' overhang in presence of FEN1 surprisingly reduces the distance necessary between the Cpf1 cleavage site and the site of ligation of the hairpin. Without being limited by theory, FEN1 may promote cleavage of protruding nucleotides present in the 5' end of the hairpin in cases where Cpf1 generates a longer target region. Indeed, in contrast to Cas9, Cpf1 does not always cleave at the same position. Following ligation of said hairpin, gap filling and ligation reactions are performed using methods well-known in the art.

Thus, according to a first embodiment, the method of the invention further comprises the step of:

- hybridizing and/or ligating one or more single or double-stranded nucleic acid molecules to the isolated nucleic acid target region.

Preferably, said single or double-stranded nucleic acid molecule is hybridized to a blunt end or to a 5'- or 3'-overhang of the target region. Ligation of a single or double-stranded nucleic acid molecule to a blunt end is preferably performed when the Type II Cas protein is the Cas9 wild-type protein, as Cas9 cleaves double-stranded nucleic acid molecules to generate blunt ends. Ligation of a single or double-stranded nucleic acid molecule to an overhang is preferably performed when the Type II Cas protein is Cpf1, as Cpf1 cleaves double-stranded nucleic acid molecules to generate a 4 to 8 base overhang. Ligation may also be performed directly without hybridization when a single-stranded nucleic acid molecule (e.g. an oligonucleotide) binds to a single-stranded region of the target that directly abuts a double-stranded region.

However, given the variation in the number of nucleotides protected by the Type II Cas protein, according to a more preferred embodiment, said single-stranded nucleic acid molecule is hybridized to a single-stranded region of the isolated target nucleic acid that is located at least 50 nucleotides away from the double-stranded region.

In a particular embodiment, the method may comprise the steps of:

- hybridizing at least one single-stranded nucleic acid molecule to the isolated nucleic acid molecule, and
- ligating said extended single-stranded nucleic acid molecule to the double-stranded region.

According to another embodiment, the method comprises the steps of:

- hybridizing at least one single-stranded nucleic acid molecule to the isolated nucleic acid molecule,
- extending the single-stranded nucleic acid molecule to the double-stranded region, preferably by contacting said isolated target nucleic acid with a nucleic acid polymerase, and
- ligating said extended single-stranded nucleic acid molecule to the double-stranded region.

According to a preferred embodiment, the at least one single-stranded nucleic acid molecule is hybridized and ligated to a 3'-overhang. Preferably, ligation to the 3' overhang occurs when a Type II Cas protein nickase or a catalytically dead Type II Cas protein is used, more preferably a catalytically dead Type II Cas protein. Preferably, said single-stranded nucleic acid molecule hybridizes to a region that is at least 50 nucleotides away from the PAM. Ligation of at least one single-stranded nucleic acid molecule to a 3' overhang is notably exemplified in FIGS. 8, 9D, and 9E. Methods of hybridization, extension and ligation are well-known to the skilled person.

In some cases, any of the above embodiments may be repeated, for example to add a second single-stranded nucleic acid molecule to the isolated nucleic acid molecule. Said second single-stranded nucleic acid molecule may be hybridized to the same strand or to the opposite strand, and may comprise a tag or not. Said single-stranded nucleic acid molecule may by only partially complementary to the sequence of the isolated nucleic acid molecule. Said single-stranded nucleic acid molecule may preferably comprise a spacer region, for example, a 12-carbon spacer, that does not bind to the isolated nucleic acid molecule (e.g. is not complementary to the sequence of the isolated nucleic acid molecule). Preferably, the single-stranded nucleic acid molecule(s) comprises a 5' phosphate group for ligation.

Optionally, excess reagents, such as non-hybridized single-stranded nucleic acid molecules may then be eliminated. As an example, non-hybridized single-stranded nucleic acid molecules may be eliminated by contacting the sample comprising the isolated target region with an enzyme having 3' to 5-exonuclease activity, more preferably exonuclease I.

According to a preferred embodiment, after hybridization of the single-stranded nucleic acid molecule to the target region, the method of the invention further comprises the step of:

performing strand displacement on the isolated target nucleic acid molecule.

Methods of strand displacement are known in the art. This advantageously allows recovery of the target region, wherein said target region comprises a short 5'-overhang. Preferably, the length of said 5' overhang corresponds to the length of the sequence protected by the Cas9, more preferably said overhang is 23 to 25 nucleotides in length. An isolated target region having a 5'-overhang may then be used as a template to hybridize and ligate oligonucleotides, for example for the construction of hairpin structures. Strand displacement is preferably performed by incubating the isolated target region with the oligonucleotide and, optionally, a polymerase, preferably at room temperature. According to a particular embodiment, strand displacement may be performed in the presence of RecA.

Preferably, strand displacement is performed when one strand of the target region has been nicked by a Type II Cas protein nickase.

After strand displacement, excess single-stranded nucleic acid molecules and the strand displacement product may be eliminated. Thus, according to a preferred embodiment, the method further comprises the step of:

eliminating excess single-stranded nucleic acid molecules and the strand displacement product.

According to a preferred embodiment, said excess single-stranded nucleic acid molecules and strand displacement product are eliminated by contacting the nucleic acid molecule with an enzyme having 3' to 5-exonuclease activity, more preferably exonuclease I. Advantageously, excess single-stranded nucleic acid molecules and strand displacement product are specifically eliminated, with no effect on double-stranded nucleic acid, or on the 5'-overhangs.

According to a preferred embodiment, one or more single-stranded nucleic acid molecules may then be hybridized and ligated to the 5'-overhang of the target region. Preferably, ligation to the 5' overhang occurs after strand displacement, and optionally, after elimination of the excess single-stranded nucleic acid molecules and the strand displacement product. This advantageously generates a hairpin structure which is particularly adapted for use in downstream applications, such as those described in WO 2011/147931, WO 2011/147929, WO 2013/093005, and WO 2014/114687, incorporated herein by reference in their entirety. Alternatively, the hairpin structure generated here may be particularly adapted for use as a hairpin precursor molecule (e.g. the HP2 molecule described in WO 2016/177808, incorporated herein by reference in its entirety).

Preferably, the one or more single-stranded nucleic acid molecules of any of the above embodiments has optimized hybridization specificity as described in Zhang et al., *Nat Chem,* 2012, 4(3):208-214, incorporated herein by reference in its entirety. Alternatively, said one or more single-stranded nucleic acid molecules of any of the above embodiments may be degenerate.

Preferably, the one or more single-stranded nucleic acid molecules of any of the above embodiments comprises a tag. As a non-limiting example, the tag may be FITC, digoxigenin, biotin, or any other tag known to the skilled person. Advantageously, the presence of a tag enables the nucleic acid molecule to be further isolated by hybridization methods, as are well-known to the skilled person, or detected and, optionally, quantified within a sample. Alternatively, the presence of a tag enables the skilled person to further purify the isolated nucleic acid using the label. For example, the molecule may be isolated on beads coated with streptavidin when the oligonucleotide is labelled with biotin. Alternatively, the presence of a tag enables the skilled person to attach the isolated nucleic acid to a support, such as a bead or a chip. Preferably, said support is functionalized, for example, by coating it with streptavidin or a COOH group, that reacts with the tag. According to a particular embodiment, at least one of the single-stranded nucleic acid molecules of any of the above embodiments comprises a sequence complementary to an oligonucleotide bound to a surface. Preferably, said oligonucleotide comprises a modification at its 3' end to prevent extension. Single-stranded nucleic acid molecule hybridization and ligation to the 3' overhang, with or without a tag, advantageously generates a hairpin structure which is particularly adapted for use in downstream applications, such as those described in WO 2011/147931, WO 2011/147929, WO 2013/093005, and WO 2014/114687. Preferably, any of the embodiments described above generate a hairpin having a "Y" shape, as illustrated in FIGS. 7F and 7G.

The present invention further allows the skilled person to enumerate the number of nucleic acid molecules carrying the said sequence. According to a preferred embodiment, the method of the present invention further comprises detecting and quantifying nucleic acid molecules as described in WO 2013/093005.

Isolated nucleic acid molecules of the present invention are particularly suited to downstream analyses by single-molecule analysis methods, such as those described in WO 2011/147931 and WO 2011/147929, as well as nucleic acid detection and quantification as described in WO 2013/093005, and detection of protein binding to nucleic acids as described in WO 2014/114687. Thus, further embodiments and applications of the present method can be found in these applications.

According to a preferred embodiment of the invention, the method comprises the enrichment of an SNP or genetic mosaicism comprised within an isolated target region. The SNP or genetic mosaicism may be comprised in a target region recognized by the Type II Cas protein:gRNA complex or in an adjacent region. Preferably, the gRNA comprises the nucleotide base corresponding to the minor allele of the SNP, allowing protection of the target region comprising said minor allele. When multiple alleles of the SNP are present at a given locus, multiple gRNA molecules may be provided, corresponding to each allele, preferably to each minor allele. In cases where gRNA molecules corresponding to both the major and minor alleles are provided, the number of isolated target regions comprising each allele may be quantified, for example to determine if a subject is homozygotic or heterozygotic at the SNP locus. Preferably, the base corresponding to the SNP locus is located within the gRNA sequence at any one of bases −1 to −10, preferably −1 to −6, preferably −4, −5, or −6 relative to the PAM site. Indeed, when a mismatch occurs at one or more of these bases, protection of the nucleic acid region from exonuclease digestion is reduced or abolished. This positioning is particularly advantageous as the presence or absence of an SNP may be determined with reduced possibility for error. In some cases, the target nucleic acid region is further sequenced to determine the allele at the SNP locus. This may notably be performed when a gRNA comprising a degenerate base at SNP locus is used, or to identify the alleles that may be present at adjacent SNP loci, for example within the adjacent region. Indeed, as is well-known to the person skilled in the art SNPs that are located close to one another in the genome tend to be inherited together.

The degree by which protection of the target region is reduced or abolished will vary according to experimental conditions, the Type II Cas protein used, and/or the gRNA used. For example, it is known that the Type II Cas protein Cpf1 has greater binding specificity than Cas9 (Strohkendl et al., *Molecular Cell,* 2018, 71:1-9). Thus, protection of a region comprising a mismatch will be greater when Cas9 is used than when Cpf1 is used. It is therefore preferable to use a Cpf1 protein or variant thereof having optimized binding specificity, or a mutated Cas9 protein having increased binding specificity such as those described herein.

According to a preferred embodiment of the invention, the method may further comprise sequencing the isolated nucleic acid molecules. Many sequencing methods are available to the skilled person. The method of the invention is particularly well suited for generating hairpins for use in single-molecule sequencing methods, such as those described in described in WO 2011/147931 or WO 2011/147929. The isolated nucleic acid may further be used as a template for specific or non-specific polymerase chain reaction, isothermal amplification, such as loop-mediated isothermal amplification, strand displacement amplification, helicase-dependent amplification, nicking enzyme amplification reaction, reverse transcription, enzymatic digestion, nucleotide incorporation, oligonucleotide ligation, and/or strand invasion. Isolated nucleic acid may also be used as a substrate for sequencing, such as Sanger dideoxy sequencing or chain termination, whole genome sequencing, hybridization-based sequencing, pyrosequencing, capillary electrophoresis, cycle sequencing, single-base extension, solid-phase sequencing, high-throughput sequencing, massively parallel signature sequencing, nanopore-based sequencing, transmission electron microscopy sequencing, optical sequencing, mass spectrometry, 454 sequencing, sequencing by reversible terminators, "paired end" or "mate pair" sequencing, exonuclease sequencing, ligation sequencing (e.g. SOLiD technology), short-read sequencing, single molecule sequencing, chemical degradation sequencing, sequencing by synthesis, massive parallel sequencing, real-time sequencing, semiconductor ion sequencing (e.g. Ion Torrent), multiplex sequencing of paired-end ditags (MS-PET), sequencing by droplet microfluidics, partial sequencing, fragment mapping, as well as combinations of any of these methods.

According to a preferred embodiment, the method of the invention further comprises sequencing nucleic acid molecules by means of single-molecule sequencing, next generation sequencing, partial sequencing, or fragment mapping, more preferably by means of single-molecule sequencing as described in WO 2011/147931 or WO 2011/147929.

According to a preferred embodiment of the invention, the method may further comprise detecting the binding of a protein to a specific nucleic acid sequence. A variety of methods for detecting protein binding are available to the skilled person. The method of the invention is particularly well suited for generating hairpins for use in protein binding methods using single-molecules, such as that described in WO 2014/114687. The isolated nucleic acid may further be used as a substrate for detecting protein binding to nucleic acid, for example, as a substrate for detecting epigenetic modifications. Isolated nucleic acid may be used, for example, in bisulfite conversion, high resolution melt analysis, immunoprecipitation (e.g. ChIP, enChIP), microarray hybridization, and other analyses of nucleic acid/protein interactions well-known to the skilled person. The term "epigenetic modifications," as used herein refers to modifications of the bases constituting a nucleic acid molecule which take place after the synthesis of said nucleic acid molecule. As a non-limiting example, a base modification may result from damage to said base. Epigenetic modifications include, for example, inter alia, 3-methylcytosine (3mC), 4-methylcytosine (4mC), 5-methylcytosine (5mC), 5-hydroxymethylcytosine (5hmC), 5-formylcytosine (5fC) and 5-carboxylcytosine (5caC), as well as 6-methyladenosine (m6A) in DNA, 5-hydroxymethyluracil (5hmU) and pseudo-uridine in RNA, and 3-methyl cytosine (3mC) and N6-methyladenosine (m6A) in DNA and RNA.

Likewise, the detection of modified bases resulting from nucleic acid damage, such as DNA damage. DNA damage occurs constantly because of chemicals (i.e. intercalating agents), radiation and other mutagens may be performed on the isolated nucleic acid. DNA base modifications resulting from these types of DNA damage are wide-spread and play important roles in affecting physiological states and disease phenotypes. Examples include 8-oxoguanine, 8-oxoadenine (oxidative damage; aging, Alzheimer's, Parkinson's), 1-methyladenine, 6-O-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer).

Preferably, the method of the invention further comprises detecting the binding of a protein to a specific nucleic acid sequence as described in WO 2014/114687.

A further object of the present invention is a composition for nucleic acid enrichment comprising a Type II Cas protein and a gRNA complementary for a specific nucleic acid site, comprising a nucleic acid target region.

A further object of the present invention is a kit that can be used for nucleic acid isolation and enrichment according to any of the methods or embodiments of the invention described herein. The kit will provide the materials and methods for nucleic acid isolation and enrichment according to the invention as described previously herein. As such, the kit will include materials necessary for nucleic acid isolation according to the methods described herein. Contents may vary according to the Type II Cas protein to be used (e.g. wild-type, nickase, or catalytically inactive), the chosen method of protecting a given nucleic acid molecule from exonuclease activity (e.g. nucleic acid adaptors such as a hairpin, or a site-specific endonuclease), the nucleic acid region to be targeted, etc, according to any of the modalities described herein.

According to a particular embodiment, the kit of the present invention comprises:

a) a Type II Cas protein, b) at least one gRNA, said gRNA being complementary to a site in a nucleic acid molecule, c) at least one enzyme having exonuclease activity, d) optionally, at least one protease, and e) optionally, a notice of use.

According to an alternative embodiment, said kit comprises EDTA, preferably a solution of EDTA, in place of or in addition to the at least one protease.

According to a particular embodiment, said kit comprises two gRNAs per target region, wherein said two gRNAs complementary to sites flanking said target region. In cases where downstream multiplex analyses are desired, the kit may comprise two or more Type II Cas proteins and two or more gRNAs, thereby targeting at least two different target regions. According to another embodiment, said kit comprises at least two Type II Cas proteins, such as Cpf1 and dCas9, with the corresponding appropriate gRNAs for each Type II Cas protein. The gRNAs of said at least two Type II Cas proteins may target the same region or may target different regions or different nucleic acid molecules as described herein. In some cases, said Type II Cas protein comprised in the kit may be loaded with gRNA, thereby forming a Type II Cas protein-gRNA complex. According to a particular embodiment, when the kit comprises Type II Cas protein-gRNA complexes, said complexes are preferably mixed together in a single container. Preferably, the ratio of each Type II Cas protein-gRNA complex comprised in said kit has been predetermined for ease of use. Preferably, said at least one gRNA is complementary to a target region of interest in clinical diagnostics or genetic risk assessment. As an example, said at least one gRNA is complementary to a target region, said target region having a sequence coding for septin9 or EgfR. Indeed, the epigenetic status of these protein coding regions is known to be important for cancer outcome. As another example, said at least one gRNA is complementary to a target region, said target region having a sequence coding for Fmr1, which is involved in Fragile X syndrome. A mutation in the number of copies of a 5'-CGG-3' repeat in this gene is responsible for disease. The epigenetic status of the region upstream of this CpG island (e.g. methylation) is also known to be related to the clinical severity of the disease. As another example, said at least one gRNA is complementary to a target region in the noncoding region of DMPK. Indeed, an expansion in the number of 5' CTG-3' repeats is characteristic of myotonic dystrophy type 1. As a further example, said at least one gRNA is complementary to a target region comprising one or more cfDNA molecules. Indeed, isolation of specific cfDNA, such as cffDNA or ctDNA, is of particular interest in a wide variety of downstream applications including prenatal testing (see, for example, Gahan, *Int J Womens Health.* 2013, 5: 177-186) and cancer diagnosis and/or monitoring (see, for example, Ghorbian and Ardekani, *Avicenna J Med Biotech.* 2012, 4(1): 3-13). One or more cfDNAs or target regions comprised within a cfDNA may advantageously be isolated directly from a biological sample (e.g. a plasma, serum, or urine sample).

As a further example, said kit comprises two or more gRNAs, wherein each of said gRNAs are complementary to a target region, or wherein at least two of said gRNAs are complementary for a target region as described herein. Preferably, said two or more gRNAs are complementary to sites flanking said target region(s). The kit described herein preferably enables isolation of at least two different target regions. Indeed, the value of certain epigenetic cancer diagnostic tests has notably been demonstrated to be improved by multiplexing, wherein the characteristics of the sequence or structure of two or more different target regions (e.g. methylation status) are analysed in a single test. A base modification (e.g. a methylated base) may be comprised in a target region recognized by the Type II Cas protein:gRNA complex or in an adjacent region. As a non-limiting example, the kit provided herein enables isolation of target regions comprising or consisting of the human GSTP1, APC and/or RASSF1 genes or appropriate regions thereof subject to DNA methylation, according to any of the methods described herein. Said isolated target regions may then be subjected to downstream analysis of methylation status, for example according to the methods provided herein (e.g. as provided in WO 2014/114687, incorporated by reference). Such a kit is particularly advantageous in the determination of risk of a subject developing prostate cancer (Wojno et al., *American health & drug benefits,* 2014, 7(3): 129), and is advantageous over existing kits which notably use bisulfite treatment of sample DNA followed by PCR. In contrast to the methods of the invention, nucleic acids isolated with existing kits may notably be prone to false positive and false negative signals, as well as sample loss due to the harsh and inefficient chemical treatment. According to a particular embodiment, the kit preferably comprises at least two gRNAs per target region, said gRNAs being complementary to sites flanking human gene(s) GSTP1, APC and RASSF1 as defined herein.

As another non-limiting example, the kit of the present invention enables isolation of at least one of the following target regions located within the human genome at the following positions: 65676359-65676418 on chromosome 17, 21958446-21958585 on chromosome 9, 336844-336903 on chromosome 6, 33319507-33319636 on chromosome 21, 166502151-166502220 on chromosome 6, 896902-897031 on chromosome 18, 32747873-32748022 on chromosome 5, 27949195-27949264 on chromosome 6, 27191603-27191672 on chromosome 7, 170170302-170170361 on chromosome 16 30797737-30797876 on chromosome 15, 7936767-7936866 on chromosome 1, 170077565-170077634 on chromosome 1, 1727592-1727661 on chromosome 2, 72919092-72919231 on chromosome 8, preferably of all 15 target regions. Isolation of said target regions is advantageous as downstream analyses of DNA methylation status of said target regions may be used to detect bladder cancer. Existing kits use methylation sensitive restriction enzymes followed by PCR to identify methylated sequences, and may therefore be limited by the presence of the appropriate restriction sites in the target regions, complicating test design, and limiting sensitivity. Thus, an improved kit for the isolation and detection of bladder cancer may preferably comprise two or more gRNAs for isolation of each of these 15 target regions according to the methods described herein, preferably for isolation of all 15 target regions, wherein said two or more gRNAs are complementary to sites flanking each target region as defined herein.

As a non-limiting example, the region targeted for isolation by the Type II Cas protein-gRNA complex(es) provided in said kit (as individual components or formed complexes) may comprise a specific sequence, a specific number of sequence repeats, or one or more nucleotide base modifications. Alternatively, the isolated target region may not comprise the specific sequence, number of sequence repeats, or one or more base modifications. As a further non-limiting example, the region targeted for isolation may be a specific length or a length that differs from said specific length. Preferably, the kit of the invention further comprises at least one restriction enzyme, and/or an RNase and/or a suitable Type II Cas protein reaction buffer. According to a preferred embodiment, said Type II Cas protein reaction buffer comprises: 20 mM Tris-acetate, 10 mM Magnesium acetate, 50 mM Potassium acetate, 100 μg/ml BSA, 0.1% Triton X-100 (pH 7.9). According to a preferred embodiment, said Type II Cas protein reaction buffer consists of: 20 mM Tris-acetate, 10 mM Magnesium acetate, 50 mM Potassium acetate, 100 μg/ml BSA, 0.1% Triton X-100 (pH 7.9). However, the skilled person may adapt this buffer if needed, according to his general knowledge.

The kit may further comprise additional elements, as is appropriate for a given application. For example, the kit may further comprise one or more protector molecules, preferably a hairpin adaptor or site-specific endonuclease, ligase and/or polymerase enzymes, oligonucleotides, dNTPs, appropriate buffers, and the like.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (See Ausubel et al., Current Protocols in Molecular Biology, Eds., John Wiley & Sons, Inc. New York, 1995; Remington's Pharmaceutical Sciences, 17th ed., Mack Publishing Co., Easton, Pa., 1985; and Sambrook et al., Molecular cloning: A laboratory manual 2nd edition, Cold Spring Harbor Laboratory Press—Cold Spring Harbor, N.Y., USA, 1989).

Additional features and advantageous aspects of the present invention are illustrated in the figures and examples below.

FIGURE LEGENDS

FIG. 1. Exemplary configurations of Type II Cas protein-gRNA complex binding to a target region. A target region (T) to be isolated and, optionally, an adjacent region (Adj) can be flanked on either side by one or more Type II Cas protein-gRNA complexes. A. A fragment of 208 bp containing a guide RNA sequence as well as the Cas9 PAM sequence was produced (SEQ ID NO: 40). The corresponding fragment was also synthesized with mutations at any one of the first six nucleotides after the PAM sequence (MM-1 to MM-6, SEQ ID NO: 41 to 46), and as illustrated. These fragments were mixed with dCas9-gRNA complex and treated with lambda exonuclease ('exo'). The remaining fragments after this treatment were quantified by qPCR using 2X Takyon premixed for SYBR Assay—no ROX (Eurogentec) with oligonucleotides having the sequence of SEQ ID NO: 37 and 38 for the wild type sequence and SEQ ID NO: 37 and 39 for the mutant MM-1 to MM-6 sequences. As shown in the quantification histogram (bottom panel), the wild type sequence was protected at approximately 72% as compared to the positive control (no exonuclease treatment). Surprisingly, we observed some protection of the MM-1 (51% protection) and MM-2 and MM-3 targets showed half the protection level compared to the WT (35 and 32% respectively). Mismatches at base positions 4, 5 or 6 from the PAM sequence (MM-4, MM-5 and MM-6) almost completely prevent the ability of dCas9 to protect these fragments. B. The adjacent region is protected by two Type II Cas protein-gRNA complexes binding to target regions on either side of said adjacent region. C. The middle target region is protected by Type II Cas protein-gRNA complexes binding to target regions on either side in addition to the Type II Cas protein-gRNA complex binding to said target region. The binding of multiple Type II Cas protein-gRNA complexes can increase exonuclease protection of an internal target region and/or of an adjacent region.

FIG. 2. The efficiency of protection by the dCas9 protein-gRNA complex is tightly linked to the ability of the wild-type Cas9-gRNA complex to cut the same targeted region. A. Schema of the fragment used with the location of the two RNA guides and the sizes of the various fragments indicated. B. The wild-type Cas9 protein (Cas9WT) was loaded with either the gRNA Fmr1 #1(lane 2, SEQ ID NO: 3) or the gRNA Fmr1 #3(lane 4, SEQ ID NO: 5) and incubated with the nucleic acid fragment "2.6 kb+loop" illustrated in A, to determine their efficiency of cutting. The Type II Cas protein-gRNA complexes were then removed from DNA by treatment with Proteinase K and RNaseA and analysed on the Fragment Analyzer® (AATI©) with the High Sensitivity NGS Fragment Analysis Kit (1 bp-6,000 bp). Incubation with the wild-type Cas9 protein-Fmr1 #1gRNA complex (lane 2) showed almost complete digestion (94%) whereas only 40% of the original fragment is cut with the wild-type Cas9 protein-Fmr1 #3gRNA complex (lane 4). The same two RNA guides were also loaded on dCas9 and used on the same fragment. However, in this case, the fragment was also incubated with lambda exonuclease, exonuclease I, and PvuII. More than 90% of the adjacent region was protected from exonuclease digestion with the dCas9-gRNA-Fmr1 #1gRNA complex (lane 3) whereas only 37% was protected with the dCas9-gRNA-Fmr1 #3gRNA complex (lane 5). These percentages are in accordance with the fraction of fragment digested with the corresponding wild-type Cas9-gRNA complexes. Lane 1 represents the control experiment without Type II Cas protein-gRNA complex or exonuclease treatment.

FIG. 3. Incubation with site-specific endonucleases during the exonuclease treatment allows fragments protected by non-specific binding of the Type II Cas protein-gRNA complex to be eliminated. A. Schema of the fragment used with the location of the RNA guide and the sizes of the various fragments indicated. B. The fragment was incubated with various forms of Cas9 to determine the percentage of non-specific binding of the Cas9 protein-gRNA complex and quantification was performed on a Fragment Analyzer® (AATI©) with the High Sensitivity NGS Fragment Analysis Kit (1 bp-6,000 bp). Lane 1 represents the control experiment without Type II Cas protein-gRNA complex or exonuclease treatment. In lane 2, the Type II Cas protein-gRNA complex was incubated with DNA in the absence of both the crRNA and tracrRNA, which together comprise the gRNA. In lane 3, the Type II Cas protein-gRNA complex was incubated with only the tracrRNA and lane 4, only the crRNA. In these conditions, the Type II Cas protein-gRNA complex should not bind to its target. However, 5-7% of the fragments are protected from exonuclease treatment. In lanes 5 and 6, the Type II Cas protein-gRNA complex was loaded with gRNA (comprising the annealed tracrRNA and crRNA), except that in lane 6, the restriction enzyme PvuII was added along with the exonucleases to liberate more ends. This additional step eliminates the non-specific binding of the Type II Cas protein-gRNA complex. Indeed, the non-specifically protected fragments, corresponding to the smear, completely disappear; only the expected fragment of 0.92 kb is observed in lane 6. C. Schematic representation of the fragment used to determine the efficiency of using Cpf1 as a site-specific endonuclease (same fragment as in 3A). The Cpf1 guide was designed such that the Cpf1 PAM sequence is located outside of the fragment to be protected (as illustrated by the arrow pointing away from said fragment). Expected fragment sizes are indicated. D. Quantification of the different fragments generated by contacting the DNA with dCas9-Fmr1 #1gRNA (SEQ ID NO: 3) complex, Cpf1crRNA-009 #2(SEQ ID NO: 36) and lambda and ExoI exonucleases on the Fragment Analyzer® (AATI©) with the High Sensitivity NGS Fragment Analysis Kit (1 bp-6,000 bp). The fragment is initially incubated with the dCas9-gRNA complex for 20 minutes to allow its binding to the target in excess, thereby increasing the non-specific binding of dCas9 (1:200:400 ratio of DNA:dCas9:gRNA). Cpf1 and exonucleases were then added to the mix. Lane 1 represents the control experiment with dCas9-Fmr1 #1gRNA but without any exonuclease treatment. In lanes 2 and 3, the DNA fragment and dCas9-gRNA-FMR1 #1 were incubated for 20 min with exonuclease alone (lane 2), or with Cpf1crRNA-009 #2 complex (lane 3). The use of Cpf1 as a specific endonuclease allows the recovery of more than 52% of the desired protected fragment compared to only 15% when not used.

Figure 4A:
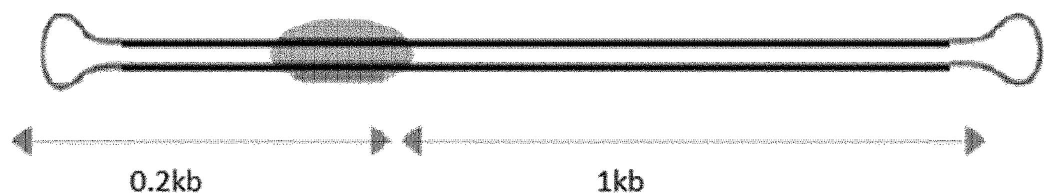

FIG. 4. The mechanism of protection from exonucleases differs between the Cas9 and Cpf1 proteins. A. Schema of a nucleotide fragment comprising a hairpin on either end and an intermediate target region to which an appropriate Type II Cas protein-gRNA complex (grey oval) can bind. The grey line indicates the gRNA; fragment sizes are indicated. B. (left panel) Exonuclease digestion profiles following Type II Cas protein-gRNA complex binding to the nucleotide fragment shown in A. Hairpins were ligated to either end of the nucleotide fragment, and a Type II Cas protein-gRNA complex comprising Cpf1 (lane 2), wild-type Cas9 (lane 3), Cas9n nickase (lane 4) or dCas9 (lane 5) was then incubated with the fragment for 1 hour. The reaction was treated with lambda exonuclease and exonuclease I. Lane 1 corresponds to the control in which no Type II Cas protein-gRNA complex was added. Type II Cas protein cleavage efficiency (%) is indicated. The presence of the 1 kb and 0.2 kb fragment with the Cas9 nickase and Cas9 dead (lane 4 and 5) is likely due to the incomplete ligation of the protector hairpin molecules at both ends of the fragment. (right panel) Exonuclease digestion profiles following Type II Cas protein-gRNA complex binding to the nucleotide fragment, wherein the Type II Cas protein-gRNA complex was removed from the nucleotide fragment prior to exonuclease treatment by treatment with a protease and an RNase. Lanes are as in the left panel. Recovery efficiency (%) of the protected fragment is indicated.

FIG. 5. Optimization of Type II Cas protein and gRNA quantities needed to protect nucleic acid from enzymes having exonuclease activity. A. Linearized 2.6 kb BsaI fragment from the plasmid pPS009 (SEQ ID NO: 1) comprising a hairpin on one end was run on a Fragment Analyzer® (AATI©) with the High Sensitivity NGS Fragment Analysis Kit (1 bp-6,000 bp) after treatment with the dCas9-Fmr1 #1gRNA complex. Different ratios of X:Y:Z (wherein X is molecules of DNA, Y of dCas9, and Z of gRNA) were tested as indicated (lanes 2-7). After incubating the linearized fragment with the dCas9-Fmr1 #1gRNA complex, lambda exonuclease (λ Exo) and PvuII enzymes were added. After this treatment, the expected size of the DNA fragment size will be 1.1 kb with 300 bases of ssDNA at the 3' end (corresponding to the sequence between the PvuII site and the RNA guide gRNA-Fmr1 #1). Lane 1 corresponds to the untreated DNA; lane 8 is the molecular weight marker. B. The area under the curve was used to calculate the efficiency of protection from exonuclease digestion, as compared to the original 2.6 kb fragment. C. The ratio of target:Type II Cas protein:gRNA may be optimized for each target. 1 ug of *E. coli* genomic DNA (gDNA) was incubated with 6 different Cpf1-gRNA complexes (2 gRNAs designed per target for 3 different targets) at different ratios as indicated on the X axis of the graph and the fragment protection was quantified using the Fragment Analyzer® (AATI©) with the High Sensitivity NGS Fragment Analysis Kit (1 bp-6,000 bp). The best ratio of target:Type II Cas protein:gRNA to obtain maximum protection may vary between targets. The optimum ratio is 1:400:800 for target 2, whereas it is more than 1:1600:3200 for target 1 and target 3 (oriC). D. Four pairs of Cpf1:crRNA complexes were designed to protect 4 different targets of *E. coli* gDNA (with two Cpf1:crRNA complexes flanking a central adjacent target region of each loci, as illustrated for Cpf1 in FIG. 9A, schema 1), and contacted the *E. coli* gDNA with the Cpf1-gRNA complexes at the highest ratio tested in panel C (for which maximum protection was obtained for all targets (1:1600:3200)). Visualization of the protected fragments was performed on a Fragment Analyzer® (AATI©) with the High Sensitivity NGS Fragment Analysis Kit (1 bp-6,000 bp).

FIG. 6. Estimation of the size of the target region of the nucleic acid molecule that can be protected from exonuclease by the Type II Cas protein-gRNA complex. A. Schema of the experiment, in which a Cas9-gRNA complex recognizes a target region within a double stranded nucleic acid molecule comprising a FITC molecule at the 3' end of the strand containing the PAM sequence, and protects it from digestion by the λ Exo. B. Size of the target region directly interacting with or shielded by the Type II Cas protein-gRNA complex was determined in the presence of ssDNA size markers labelled with FITC (left panel), and size determined with single-base resolution (right panel).

Figure 7:
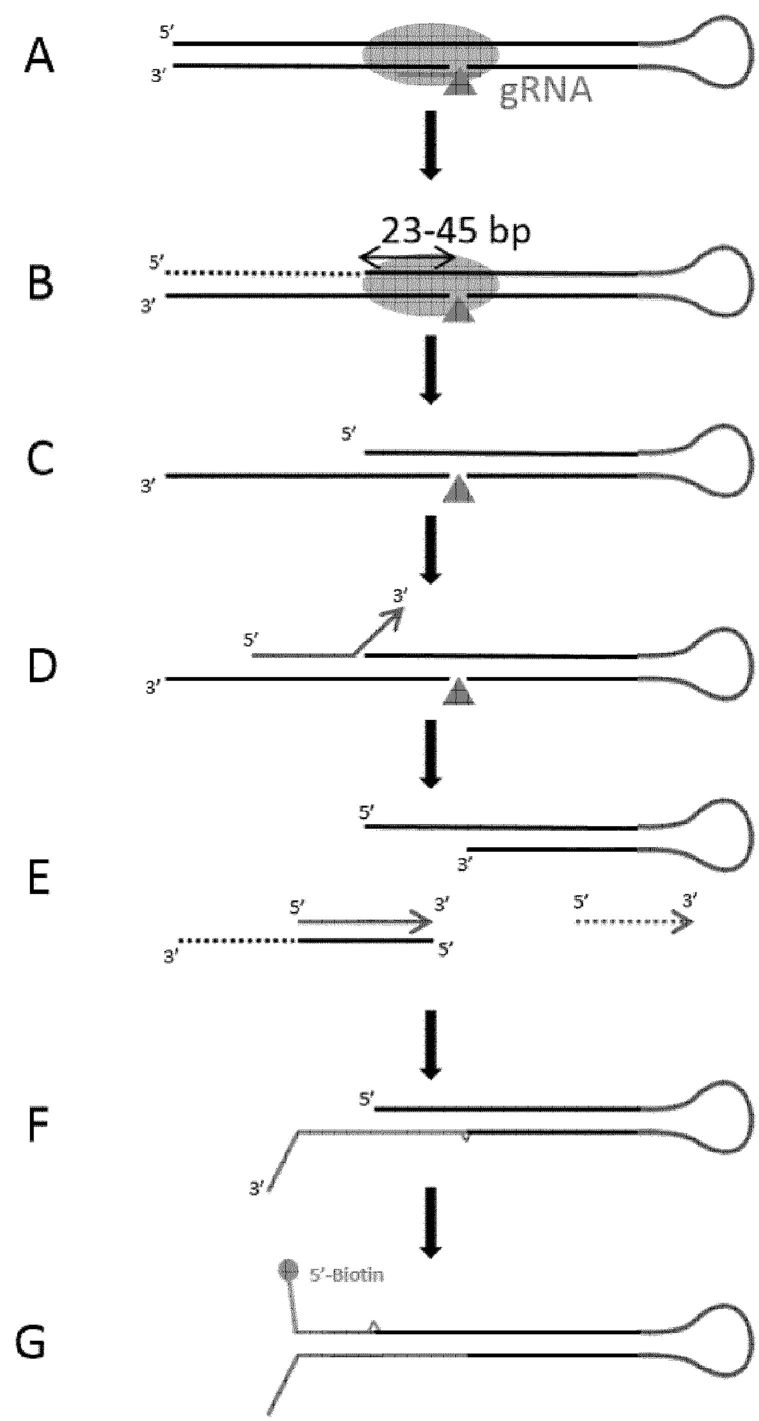

FIG. 7. Schema of the method of the invention using a Type II Cas protein nickase-gRNA complex to produce the Y-shape of a hairpin. A. Linearized DNA to which a synthetic hairpin has been ligated was contacted with the Type II Cas protein-gRNA complex Cas9n (D10A) loaded with gRNA-*Ecoli*#1(grey circle), generating a nick in one strand of the DNA (the strand hybridized with the gRNA molecule). B. A cocktail of restriction enzymes comprising EcoRI and PvuII and λ Exo was added to the reaction mixture to digest all exposed ends, followed by treatment with a protease to remove the Type II Cas protein nickase-gRNA complex. C. The DNA strand nicked by Cas9n, which can be subject to further processing. D. The DNA strand nicked by the Cas9n-gRNA complex is displaced using strand displacement and a double-stranded DNA target with a short 5' ssDNA tail of 23 to 45 bases as illustrated in E, corresponding to the target region protected by the Type II Cas protein-gRNA complex is recovered. E. Oligonucleotides and the displaced complementary strand were eliminated by exonuclease I digestion. F. The remaining 23-45 bp 5' overhang could then serve as a template to hybridize and ligate a complementary oligonucleotide. G. Hybridization of a second oligonucleotide, biotinylated at the 5' end, was performed by strand displacement to construct the Y-shaped hairpin structure. Digested fragments are indicated by dotted lines in B and E.

Figure 8:
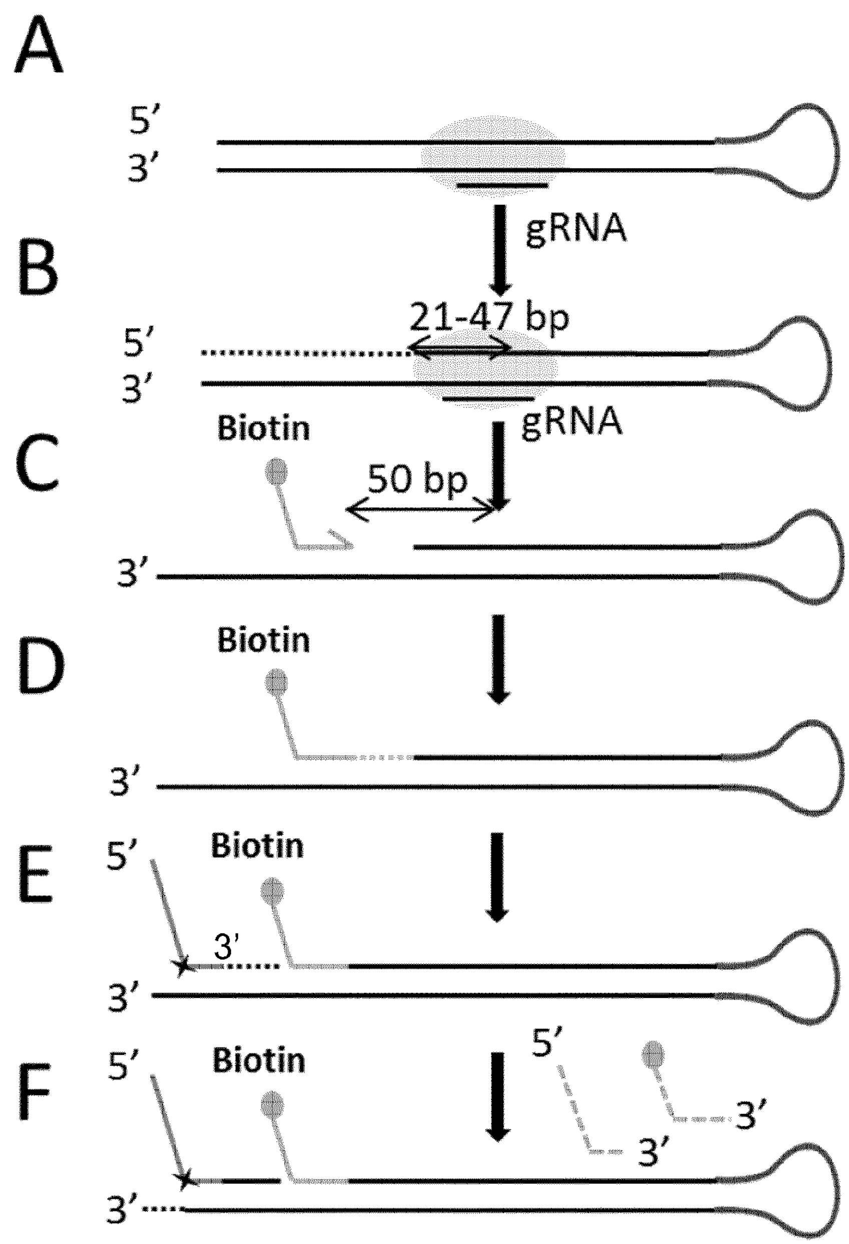

FIG. 8. Schema of the method of the invention using a catalytically dead Type II Cas protein-gRNA complex to produce the Y-shape of a hairpin. A. Linearized DNA to which a synthetic hairpin has been ligated was contacted with the dCas9-gRNA complex loaded with gRNA-*Ecoli*#1 (grey circle). B. A cocktail of restriction enzymes comprising EcoRI and PvuII, and λ Exo was added to the reaction mixture to digest all exposed ends, followed by treatment with a protease and RNase A. C. One or more oligonucleotides (e.g. a biotinylated oligonucleotide) were then hybridized to the exposed ssDNA region at least 50 bp from the PAM to compensate for the variability in the length of the protected region. D. Gaps were sealed by performing fill-in reactions and ligations to the 5' end of the desired fragments. E. Additional oligonucleotides may be added (e.g. an oligonucleotide having a complementary sequence to a surface), with gap sealing as in D. The star indicates the presence of a 12 carbon (C12) chain spacer. F. Excess oligonucleotides and the 3' ssDNA tail of target DNA were removed by exonuclease I treatment, to generate the desired Y-shaped hairpin structure. Digested fragments are indicated by dotted lines in B, D, E, and F.

FIG. 9. Schema of the method of the invention using two Type II Cas protein-gRNA complexes, loaded with two different gRNAs. A. (1) DNA was contacted with two dCas9-gRNA complexes, loaded with gRNA-*Ecoli*#1 or gRNA-*Ecoli*#2 to generate 3' ssDNA tails on each side (left panel), or with two Cas9n-gRNA complexes to generate 5' ssDNA tails on each side (right panel). (2) A cocktail of restriction enzymes and lambda exonuclease was added to the reaction mixture to digest all exposed ends, followed by treatment with a protease and RNase A (both panels). Digested fragments are indicated by dotted lines. (3) Structure of the DNA molecule after completion of the method (both panels). (4, 5) Exemplary downstream steps when using the Type II Cas nickase-gRNA complex. B. Schema of the method of the invention using sequentially Cpf1-crRNA complexes followed by dCas9-gRNA complexes (1) DNA was contacted with two Cpf1-crRNA-complexes (where the PAM sequences are within the fragment to be protected, as indicated by the arrows facing the inside of the protected region) followed by treatment with lambda exonuclease as well as ExoI exonuclease. (2) The protected fragments are then contacted with dCas9-gRNA complexes and treated with only lambda exonuclease to generate the 3' overhang. (3) The reaction is then stopped by either proteinase K treatment and/or the addition of EDTA. The protected fragments are then be purified using well-known purification methods (e.g. bead or column purification) to remove proteins and salts. C. Schema of the method of the invention using both dCas9-gRNA complexes and Cpf1-crRNA complexes. (1) The Cpf1 and dCas9 reactions can be combined into one reaction if the Cpf1 PAM sequence is outside of the region to be protected (in this case, Cpf1 acts as a site-specific endonuclease to generate the 5' overhang required for the lambda exonuclease). DNA is first contacted with dCas9-gRNA-complexes followed by simultaneous addition of the Cpf1-crRNA complexes and lambda exonuclease. (2) The reaction is then stopped by either proteinase K treatment and/or the addition of EDTA. The protected fragments are then be purified using well-known purification methods (e.g. bead or column purification) to remove proteins and salts. D. The molecule produced from the protection assay as notably exemplified in FIGS. 9A to 9C can be further processed to produce hairpin molecules suitable for further analysis. A synthetic loop, containing a sequence complementary to the 3' ssDNA overhang at one end is filled in and ligated to the enriched fragment. In parallel, a biotin oligonucleotide complementary to the other 3' ssDNA end and a "template oligonucleotide" comprising a sequence corresponding to an oligonucleotide attached to a surface is added (when the Type II Cas protein is Cpf1) to allow extension of the 3' region. This template oligonucleotide contains a modification at its 3' end to prevent extension, as illustrated by an asterisk, and may be removed by NaOH treatment, yielding an extended 3' ssDNA overhang, which may furthermore be complementary to an oligonucleotide attached to a surface. E. The enriched fragments are processed as in FIG. 9D except that the loop is produced using the enzyme FEN1, which processes protruding 5' ends as shown in the figure (middle panel).

FIG. 10. Testing Cpf1 activity and its ability to protect nucleic acid molecules from exonuclease digestion. Binding and protection of a fragment of a 6.6 kb *E. coli* PCR fragment was determined using two different Cpf1-crRNA complexes. A. Graphical representation of the *E. coli* PCR fragment used to test two Cpf1 crRNA guides. The position of the two Cpf1 binding sites is indicated, as well as their orientation and the expected size of the fragments to be generated upon cleavage. The Cpf1 PAM sequence is TTTN. In this case, the crRNA guides are 24 bases in length, with the PAM sequence facing the target DNA to be protected. B. Nucleic acid profiles following Cpf1-crRNA complex binding to the PCR product. Lane 1: Untreated PCR product. Lanes 2-4: Cpf1-crRNA #2 incubated for 30 minutes with the PCR product, with a DNA:Cpf1:crRNA ratio of 1:10:20 (lane 2), 1:20:40 (lane 3), or 1:40:80 (lane 4). Lanes 5-7: Cpf1-crRNA #2 incubated for 60 minutes with the PCR product, with a DNA:Cpf1:crRNA ratio of 1:10:20 (lane 5), 1:20:40 (lane 6), or 1:40:80 (lane 7). Lanes 8-10: Cpf1-crRNA #3 incubated for 30 minutes with the PCR product, with a DNA:Cpf1:crRNA ratio of 1:10:20 (lane 8), 1:20:40 (lane 9), or 1:40:80 (lane 10). Lane 11: Both Cpf1-crRNA #2 and Cpf1-crRNA #3 were incubated for 60 minutes with the PCR product at a ratio of 1:80:80:80 (DNA:Cpf1:crRNA #2:crRNA #3) and then treated with lambda exonuclease and exonuclease I. (*) PCR product was cleaved by both Cpf1-crRNA #2 and Cpf1-crRNA #3 and was therefore protected from exonuclease degradation. Eff.: Percentage of cleaved (lanes 2-10) or protected (lane 11) PCR product according to the initial PCR amount used for the reaction. UM: upper marker, LM: lower marker of DNF-930 dsDNA Reagent Kit (75 bp-20,000 bp) Fragment Analyzer™.

Figure 11A:
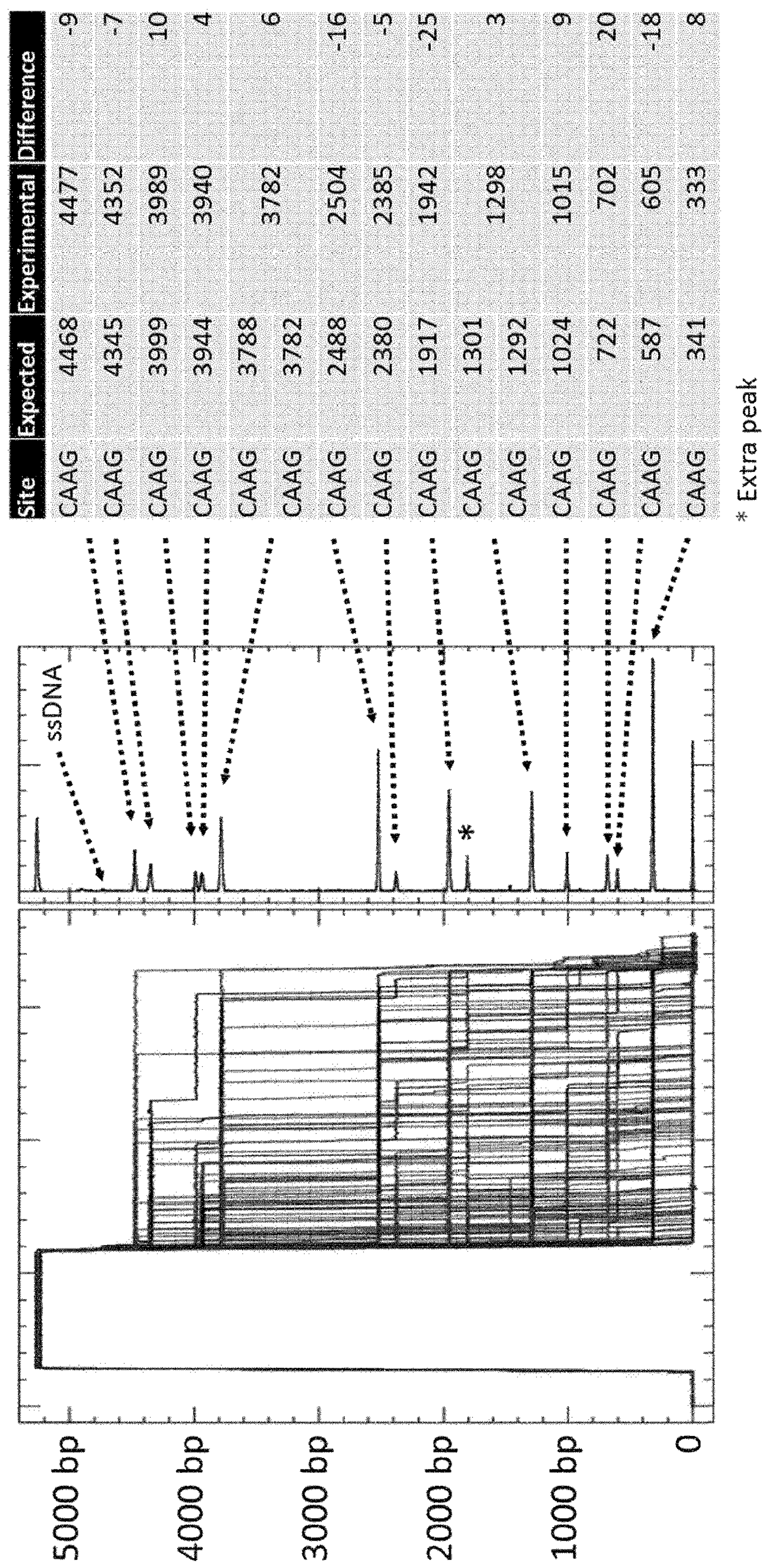
Figure 11B:
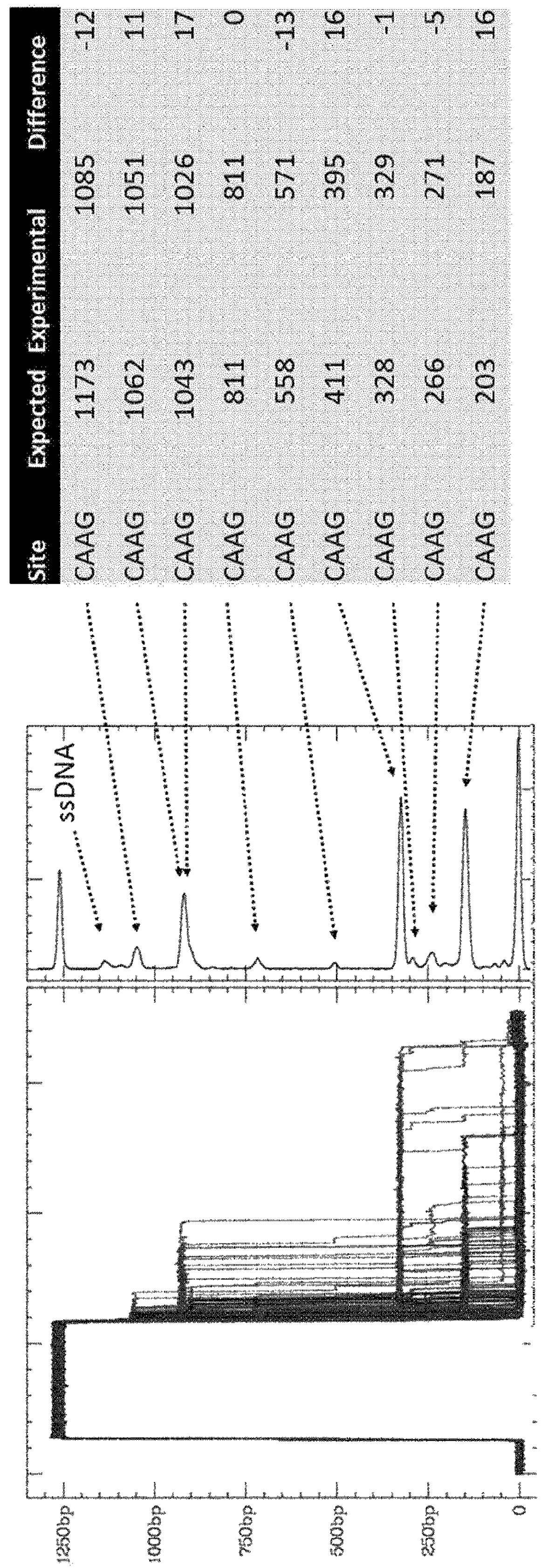
Figure 11C:
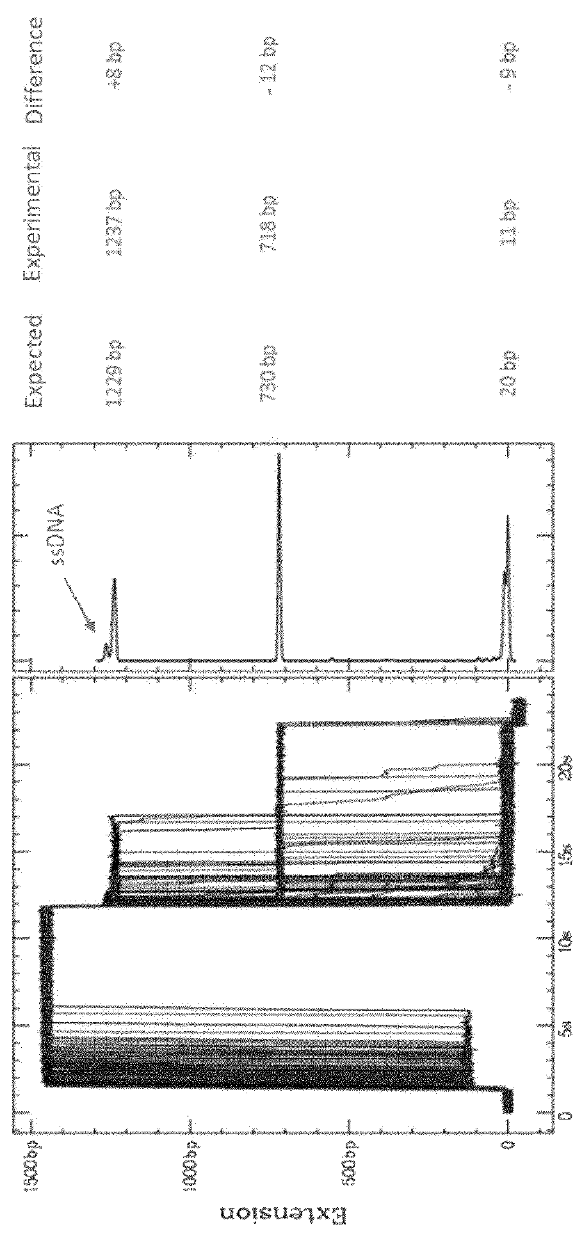

FIG. 11. Targeted enrichment of multiple nucleic acid molecules via multiplex. *E. coli* genomic DNA was linearized and a synthetic hairpin adaptor (PS421) attached to the 5' end of each nucleic acid molecule or fragment. DNA was then incubated in a multiplex reaction with both dCas9-gRNA #1 (to isolate at 5 kb fragment) and dCas9-gRNA #2 (to isolate a 1.2 kb fragment) at a DNA:dCas9:gRNA ratio of 1:100:250 for each target. CAAG fingerprinting profiles of the isolated nucleic acid target regions were obtained, and indicated successful targeted enrichment of the two fragments. A. Target #1 (5 kb) B. Target #2 (1.2 kb). C. We used the monoclonal antibody clone ICC/IF from Diagenode to detect the three predicted 5-methylated cytosine positions on target #2 having the sequence of SEQ ID NO: 34 (predicted to occur at the sequence CCwGG in *E. coli*). All three positions were properly detected on this fragment.

FIG. 12. Targeted enrichment of the human FmrI region. A. Human genomic DNA was processed using the protocol described in FIG. 9B (and example 13), with initial protection provided by the Cpf1-crRNA complex with the PAM sequence located within the target region, followed by generation of the ssDNA 3' ends using dCas9-gRNA complexes. The enriched target regions were then further processed to produce molecules suitable for our sequencing platform using the approach described in FIG. 9D. The identity of the molecule was confirmed by experimentally detecting predicted blocking positions of the oligonucleotide CAAG. B. The monoclonal antibody clone ICC/IF from Diagenode was injected into the fluidic cell to detect methylated cytosines present on this molecule, represented by the arrows.

FIG. 13. Preparation of a sequencing library from human genomic DNA containing 15 different targets and from 13 different samples. A. The list of targets that was selected for enrichment with their genomic coordinates. These regions were selected either due to the presence of epigenetic biomarkers or known loci with expanded repeats involved in human diseases. B. All guide RNAs for both Cpf1 and Cas9 were tested on PCR fragments to determine their efficiency. Results obtained for gRNAs targeting regions adjacent to the Septin 9 CpG island, a known epigenetic biomarker for colon cancer, are provided here as an example. For each target, we tested one Cpf1 guide on the left side of a central target region and one on the right side. Two different gRNAs for Cas9 were also tested on each side of the target region for each target. The percentage of cleavage efficiency is indicated for each Septin9 gRNA tested based on the expected fragment size. A protection assay was also performed using Cpf1 guide RNA on both sides of the Septin9 target and incubating the reaction with lambda exonuclease as well as exonuclease I. More than 90% of the original fragment was protected in this assay. C. Summary table of all Cpf1 as well as Cas9 guide RNAs tested for the 15 targets, as determined based on the method illustrated in 13B. All Cpf1 guides gave a cleavage efficiency of more than 70% and, with the exception of the target NDRG4.2, at least one Cas9 guide was also identified on each side of the target with more than 70% efficiency. We used this 70% baseline in this assay to select our guides, but it is possible to further optimize the reaction to obtain more than 90% cleavage (by, for example, increasing the ratio of target DNA to Type II Cas protein:gRNA complex).

EXAMPLES

The following examples are included to demonstrate preferred embodiments of the invention. All subject-matter set forth or shown in the following examples and accompanying drawings is to be interpreted as illustrative and not in a limiting sense. The following examples include any alternatives, equivalents, and modifications that may be determined by a person skilled in the art.

Example 1: Synthesis of the Guide RNA

Guide RNA(s) are synthesized in vitro using a viral transcriptional system (for example, T7, SP6 or T3 RNA polymerase) or chemically produced using automated synthesizer. In some cases, a universal tracrRNA (SEQ ID NO: 25) may be annealed to the target specific crRNA (generic sequence shown in SEQ ID NO: 24), as is further detailed in section 9.3. Three Cas9 guide RNAs flanking a region of approximately 0.9 kb within a 4 kb DNA plasmid (pPS009, SEQ ID NO: 1) containing the Fmr1 locus (SEQ ID NO: 2) were designed (gRNA-Fmr1 #1, gRNA-Fmr1 #2 and gRNA-Fmr1 #3 having the sequences of SEQ ID NO: 3, 4 and 5, respectively). For each gRNA, efficiency was tested in vitro on a standardised/controlled sample (e.g. PCR fragments) using the wild type Cas9 nuclease. This is to ensure that each Type II Cas protein-gRNA complex can cut the expected target region comprising a sequence complementary to the gRNA with a reasonable efficiency, (e.g. of at least 50%, 60%, 70%, 80%, 90%, 95%, 96%, 97%, 98%, 99%, preferably 100%).

Example 2: General Reaction Protocol

1. The Type II Cas protein is loaded with gRNA by incubation for 10 minutes at room temperature (e.g. 25° C.) in Type II Cas protein reaction buffer (20 mM Tris-acetate, 10 mM Magnesium acetate, 50 mM Potassium acetate, 100 μg/ml BSA, 0.1% Triton X-100 (pH 7.9)).
2. A sample comprising nucleic acid molecules is added to the mixture of step 1, and incubated for 1 hour at 37° C. in order to allow the Type II Cas protein-gRNA complex to bind to the target region.
3. A mixture of exonuclease(s) (e.g. lambda exonuclease) and restriction enzyme(s) are added and the mixture is incubated for 1 hour at 37° C. Enzymes are then inactivated at 75° C. for 15 minutes.
4. RNaseA (optionally) and Proteinase K treatments are performed successively for 15 minutes at 37° C. to remove the Type II Cas protein-gRNA complex from the target region. Alternatively, or in addition, the reaction can be supplemented with EDTA to stop the reaction, thereby removing the Type II Cas protein-gRNA complex from the target region.

Figure 1C:
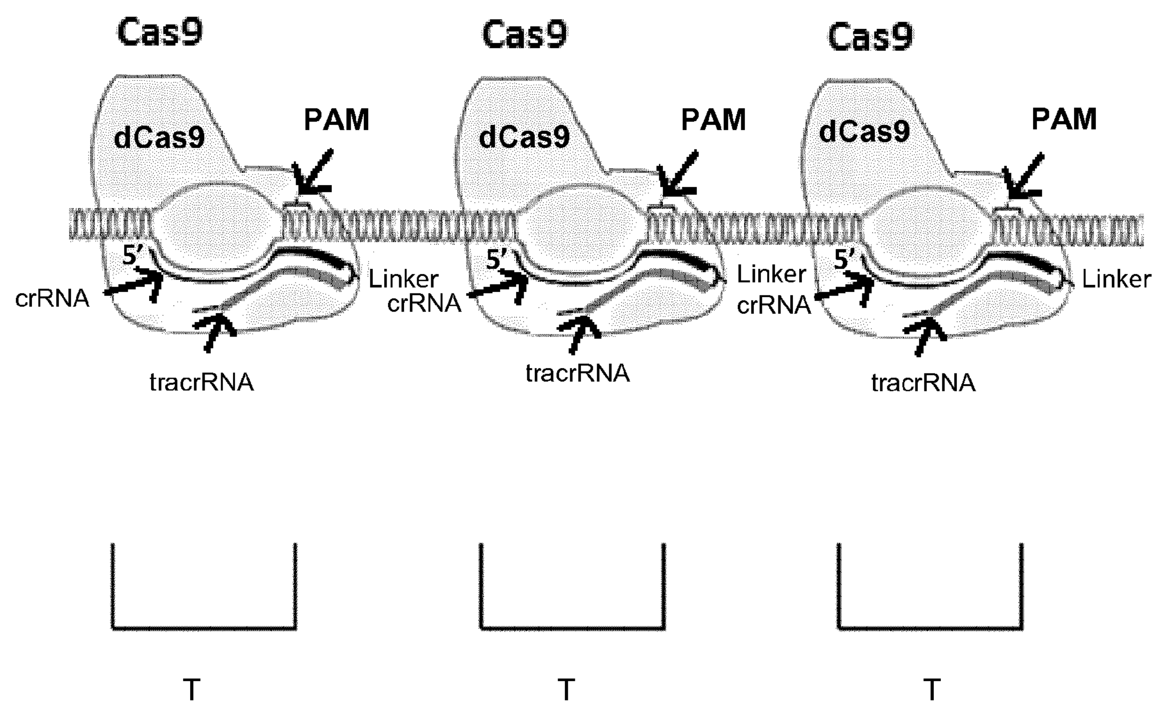

Example 3: Type II Cas Protein-gRNA Complex Binding Protects the Target Region from Exonuclease Digestion Exemplary embodiments of Type II Cas protein-gRNA complex binding to a nucleotide fragment comprising one or more target regions and, optionally, an adjacent region of interest, are shown in FIG. 1. In some cases, a single Type II Cas protein-gRNA complex may be used to protect a target region (cf. FIG. 1A). As illustrated in FIG. 1A, the Type II Cas protein-gRNA complex comprising dCas9 protects a region that comprises the gRNA sequence. Mismatches between the target region and the gRNA located within at positions −1 to −6 relative to the PAM sequence strongly reduce protection when using only a single dCas9-gRNA complex to protect the target region. In particular, mismatches at the bases located 4, 5, or 6 bases from the PAM reduce protection by 4.8 to 12-fold. Protection may be even more strongly reduced or even abolished when Type II Cas proteins having greater binding specificity (e.g. Cas9 variants or Cpf1) or modified gRNAs are used. Alternatively, a Type II Cas protein-gRNA complex may be used in tandem with a hairpin molecule to protect a target region and, optionally, an adjacent region (cf. FIG. 7A or FIG. 8A for specific embodiments using Cas9n or dCas9). Alternatively, two Type II Cas protein-gRNA complexes may be used to protect one or more target regions and, optionally, an adjacent region (cf. FIG. 1B, 1C, and FIG. 9A, schema 1). These exemplary embodiments are further described below.

Figure 2A:
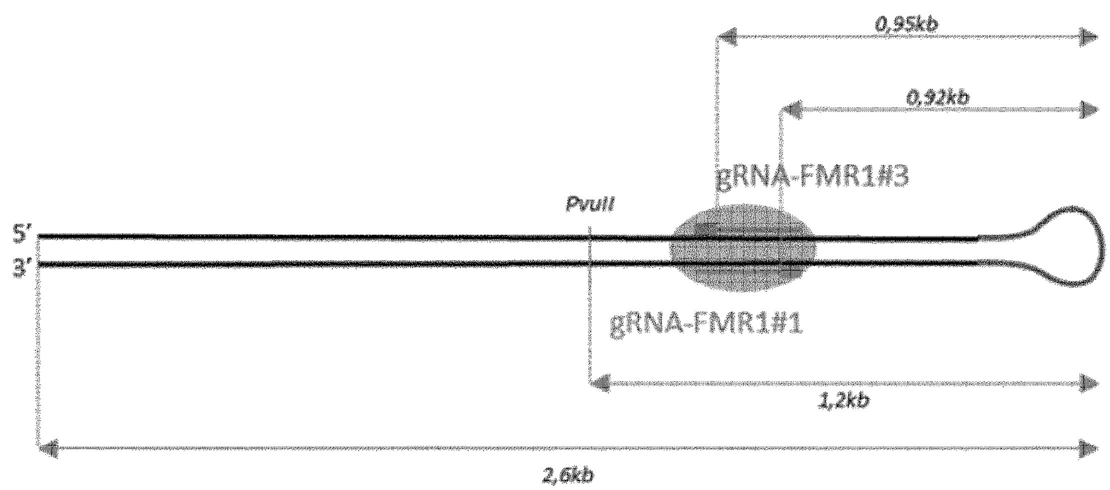

3.1 a Type II Cas Protein-gRNA Complex and a Hairpin Molecule Protects a Target Region from Exonuclease Digestion A 4 kb plasmid (SEQ ID NO: 1) was digested with the restriction enzyme BsaI to produce a linear DNA fragment of 2.6 kb, which included the 0.9 kb region of interest, as illustrated in FIG. 2A. A hairpin (PS189 of SEQ ID NO: 12) was ligated to one end of the digested fragment to block initiation of digestion of the fragment by the exonuclease from this end. The 2.6 kb fragment was then incubated with a Cas9-gRNA complex comprising gRNA-Fmr1 #1 or gRNA-Fmr1 #3(SEQ ID NOs: 3 and 5, respectively). Two fragments were obtained: 1) a first protected 0.9 kb fragment comprising the Cas9-gRNA complex at one end and the ligated hairpin at the other, and 2) an unprotected, unmodified fragment of 1.7 kb, as the gRNA was complementary to a sequence comprised in a target region located approximately 1.7 kb from the unmodified end.

The reaction was then treated with a mixture of the λ and Exo I exonucleases. Lambda exonuclease is an extremely processive 5' to 3' dsDNA exonuclease. The Exo I nuclease is also a processive exonuclease, but in the 3' to 5' direction and is specific for ssDNA. The 0.9 kb fragment included between the target region bound by the Type II Cas protein-gRNA complex and the hairpin at the other end of the DNA fragment was protected (cf. FIG. 2B, lane 3, for example). In contrast, the unprotected 1.7 kb fragment was completely digested. Thus, the Type II Cas protein-gRNA complex protects free ends from exonuclease digestion.

3.2 Two Type II Cas Protein-gRNA Complexes Protect a Target Region from Exonuclease Digestion As an alternative, the method above was performed using two Type II Cas protein-gRNA complexes: Cas9-gRNA-Fmr1 #1 and Cas9-gRNA-Fmr1 #2(SEQ ID NO: 3 and 4, respectively), instead of the Cas9-gRNA-Fmr1 #1 and a hairpin adaptor. The sample was treated as indicated in 3.1. Following treatment, the region between the two Type II Cas protein-gRNA complexes was protected (approximately 900 bp), while the unprotected fragments were completely digested.

Example 4: Protection is Dependent on Cas9-gRNA Complex Enzyme Activity

Figure 2B:
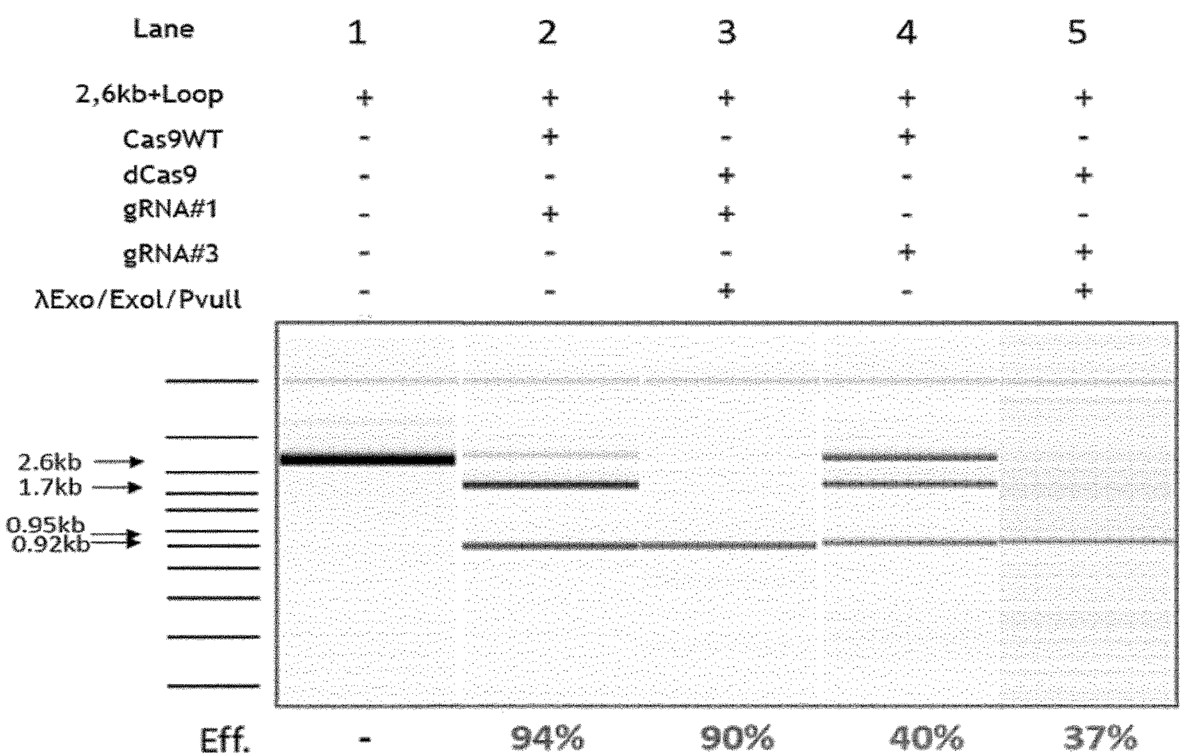

Surprisingly, in the course of these studies, it was further shown that protection level of the desired fragments, even with the catalytically inactive version of the Type II Cas protein, is directly related to the ability of the wild-type Type II Cas protein-gRNA complex to cut the DNA in vitro. As an example, a gRNA that gives poor cutting of a fragment when loaded on the Cas9 wild type (WT) protein will also give poor protection of the fragment from exonuclease degradation when the catalytically inactive dCas9 variant is used (FIG. 2B, lanes 4 and 5). These results are further detailed below.

A 2.6 kb fragment with a hairpin adaptor at one end, as described in example 3.1, was incubated with either a dCas9 or wild-type Cas9-gRNA complex, loaded with either the gRNA-Fmr1 #1 or the gRNA-Fmr1 #3, for 30 min at 37° C. The reaction containing the dCas9-gRNA complex was further treated with a mixture of the lambda and Exo I exonucleases and PvuII restriction enzyme for 30 min at 37° C., followed by inactivation for 15 min at 75° C. RNaseA and Proteinase K treatments were performed successively for 15 minutes at 37° C. to remove the Cas9-gRNA complexes from the target region.

All of these reactions were analysed on the Fragment Analyzer® (AATI©) with the High Sensitivity NGS Fragment Analysis Kit (1 bp-6,000 bp), as shown in FIG. 2. The gRNA-Fmr1 #1, when loaded on wild-type Cas9, showed an almost complete cleavage (FIG. 2, lane 2), with 94% of the 2.6 kb fragment being cleaved into two fragments of 1.7 kb and 0.9 kb. When the gRNA-Fmr1 #1 was loaded on dCas9, 90% of the expected 0.9 kb fragment was recovered after exonuclease treatment (FIG. 2B, lane 3). This is in accordance with the efficiency of cleavage of the corresponding wild-type Cas9-Fmr1 #1gRNA complex. Similarly, even with the poor cleavage efficiency of the gRNA-Fmr1 #3, the ratio between cleavage and protection is maintained, with 40% of fragment being cleaved by the wild-type Cas9-Fmr1 #3gRNA complex (FIG. 2B, lane 4) while 37% of the fragment recovered after exonuclease treatment when using the dCas9-Fmr1 #3gRNA complex (FIG. 2B, lane 5).

Example 5: Type II Cas Protein-gRNA Complex May Bind Non-Specifically in Certain Conditions The Type II Cas protein tends to bind non-specifically near the ends of DNA fragments, therefore protecting these fragments as well and reducing the efficiency of the enrichment. Surprisingly, the use of site-specific endonucleases cleaving additional sites located between the Cas9-gRNA site and the fragment end improved the efficiency of enrichment. This site-specific endonuclease can either be a restriction enzyme or the Type II Cas protein Cpf1 when the PAM sequence is located outside of the region to be protected (as illustrated by the arrow pointing outside the fragment in FIG. 3C).

Figure 3B:
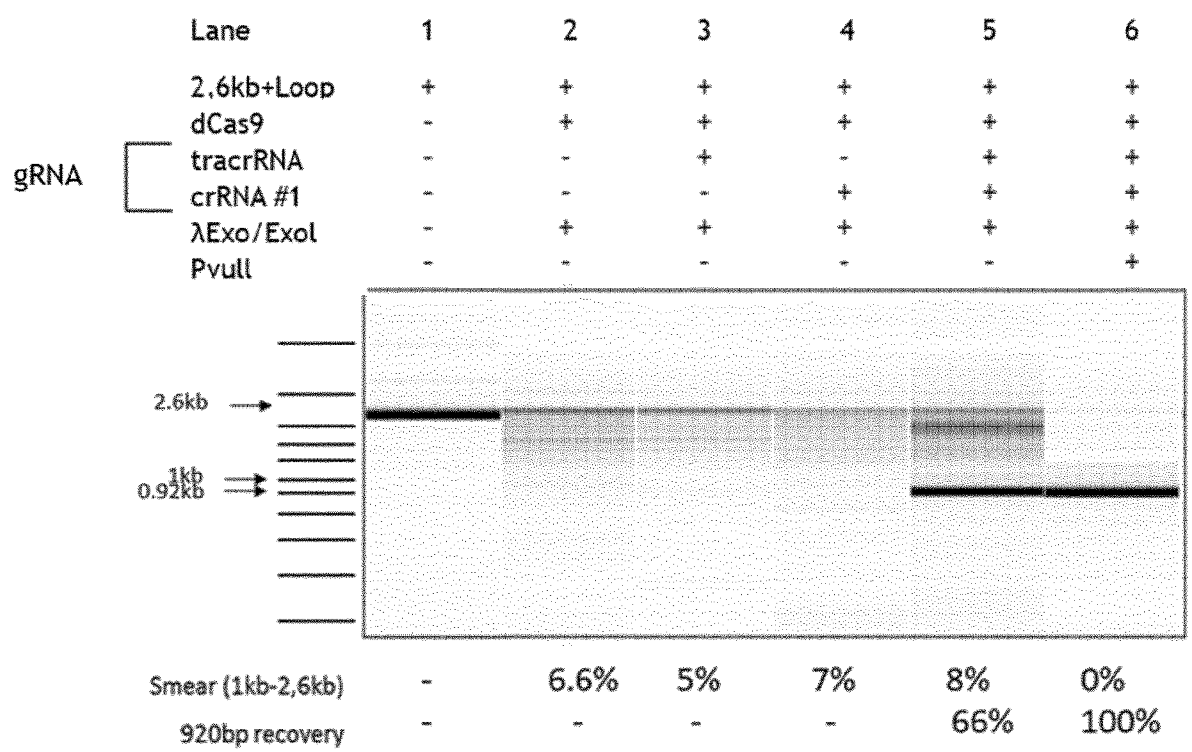

To demonstrate the non-specific binding characteristic of the Cas9 protein, a 2.6 kb fragment with a hairpin adaptor at one end, as described in example 3.1, was incubated with various forms of the dCas9-gRNA complex, including dCas9 alone (FIG. 3B, lane 2), dCas9 in complex with the tracrRNA only (FIG. 3B, lane 3), dCas9 in complex with the crRNA only (FIG. 3B, lane 4) and dCas9 in complex with the annealed crRNA:tracrRNA (or the gRNA) (FIG. 3B, lanes 4 and 5). After 30 min incubation at 37° C., the reaction was treated with a mixture of the lambda and Exo I exonucleases for 30 min at 37° C., then inactivated for 15 min at 75° C. PvuII restriction enzyme was added during exonuclease treatment of the dCas9 loaded with the annealed crRNA:tracrRNA (gRNA) (FIG. 3B, lane 6). RNaseA and Proteinase K treatments were performed successively for 15 minutes at 37° C. to remove Cas9-gRNA complexes from the target region.

These result show that all forms of the dCas9 in complex with partial or complete gRNA (i.e. with either the crRNA, tracrRNA or the complete gRNA comprising both the crRNA and the tracrRNA bind to DNA non-specifically and prevent the exonuclease digestion (revealed by the presence of a smear). The amount of undigested fragment is about 5 to 8% (as determined by smear analysis of the DNA fragment between 1 kb and 2.6 kb). These undigested fragments can be recovered by adding PvuII along with the exonuclease (FIG. 3B, lane 6), thereby eliminating non-specific protection by the Cas9 protein. Indeed, 100% of the 0.9 kb target was recovered (FIG. 3, lane 5).

Figure 3C:
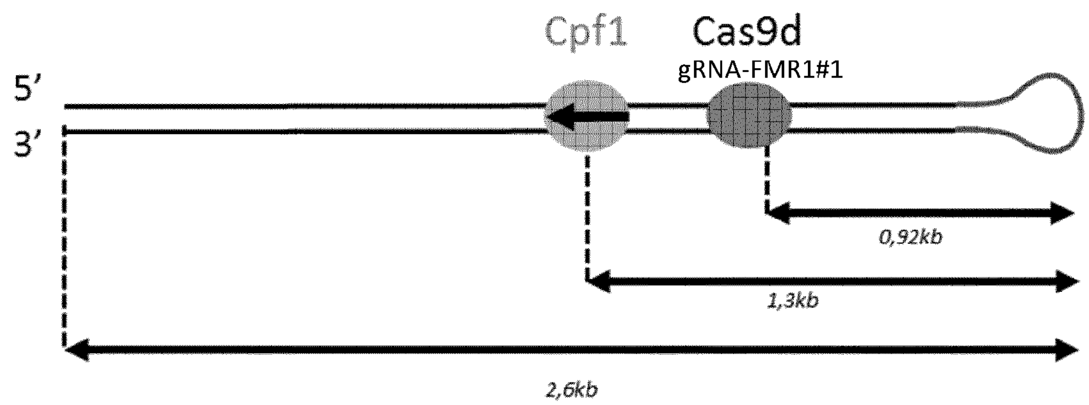
Figure 3D:
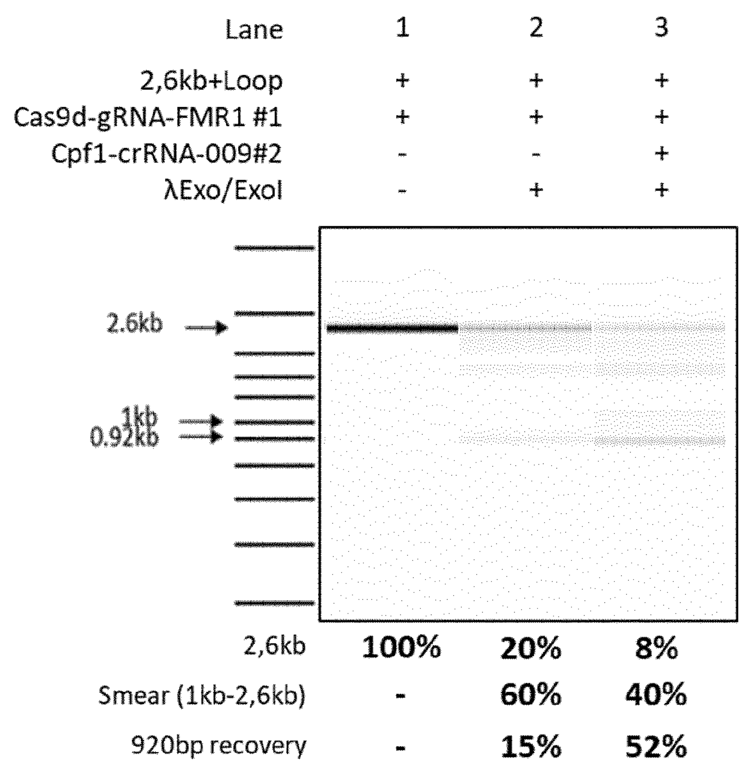

To illustrate the use of Cpf1 to act as a site-specific endonuclease, the same 2.6 kb fragment with the hairpin adaptor was incubated, as illustrated in FIG. 3C, with the dCas9-gRNA complex (FIG. 3D, lane 1). The dCas9-gRNA complex was added in excess in the reaction to increase the non-specific binding of the dCas9 (ratio target:Type II Cas protein:gRNA, 1:200:400). The exonuclease treatment was then performed alone (lane 2) or simultaneously with a Cpf1-crRNA complex (lane 3). Excess dCas9-gRNA complex induces an increase of non-specific binding of said complex, with only 15% of the expected 0.9 kb fragment is present after exonuclease treatment (FIG. 3D lane 2). When the Cpf1-crRNA complex is used to liberate 5' ends in these conditions, we were able to recover 52% of the 0.92 kb fragment. The Cpf1-crRNA complex allows the recovery of an additional almost 40% of the specific target fragments. Optimization of the conditions used during Cpf1 treatment will further increase specific target enrichment.

Example 6: Exonuclease Degradation Profiles of a Nucleotide Fragment Protected by a Type II Cas Protein-gRNA Complex Comprising Cpf1 or Cas9 Variants The ends of a 1.2 kb fragment of the 4 kb plasmid pPS009 (SEQ ID NO: 1) digested by BsmBI, comprising a target region to which a Type II Cas protein-gRNA complex can bind, were blocked by ligating hairpin adaptors (PS359 and PS137, corresponding to SEQ ID NO: 13 and SEQ ID NO: 14, respectively) to either end to prevent initiation of exonuclease digestion. After a 1-hour incubation with a Type II Cas protein-gRNA complex comprising either Cpf1 or wild-type Cas9, Cas9n or dCas9 (FIG. 4, lanes 2, 3, 4 and 5, respectively) and the crRNA #1 (SEQ ID NO: 35) for Cpf1 or the gRNA #1-FrmI #1 (SEQ ID NO: 3) for Cas9, the reaction was treated with lambda exonuclease and exonuclease I.

Figure 4B:
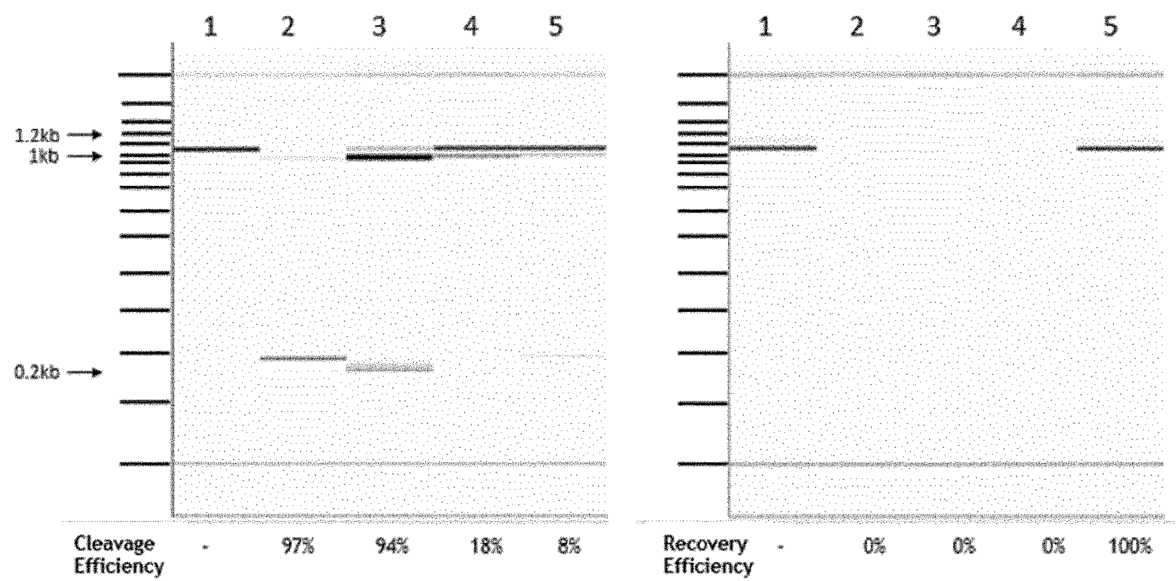

For Cpf1, only the 0.2 kb fragment remains after treatment, as shown in FIG. 4B, left panel, lane 2. This suggests that the 1 kb fragment was not protected by the Cpf1-crRNA complex (i.e. it was cleaved from the original nucleotide fragment and this end leaves the complex) and was therefore available for digestion by exonucleases. In contrast, the presence of the 0.2 kb fragment indicates that this region was protected by the Cpf1-crRNA complex. In contrast, in the case of wild-type Cas9, even if the fragment is cut (as shown by the presence of both the 0.2 and 1 kb fragments in FIG. 4B, left panel, lane 3), these fragments remain bound to the Cas9-gRNA complex comprising Cas9. Both fragments are therefore shielded from exonuclease digestion. For Cas9n and dCas9 (FIG. 4B, left panel, lanes 4 and 5, respectively), the majority of the fragment remaining after exonuclease treatment is the original 1.2 kb fragment, indicating that a Type II Cas protein-gRNA complex comprising Cas9n or dCas9 does not cleave the nucleotide, as expected. The presence of 1 and 0.2 kb fragments in the presence of the Type II Cas protein-gRNA complex comprising Cas9n or dCas9 (cleavage efficiency of 18% and 8%, respectively) is likely due to the fact that a hairpin was not successfully ligated to both ends of all of the original molecules.

For comparison, the Type II Cas protein-gRNA complexes described above were removed from the template before exonuclease treatment by digestion with proteinase K and, optionally, RNase A (FIG. 4B, right panel). In this case, the fragments present in the reactions treated with Cpf1, wild-type Cas9, and Cas9n (FIG. 4B, right panel, lanes 2, 3, and 4, respectively) were all completely digested. In contrast, the reaction containing the dCas9-gRNA complex was completely protected. Indeed, quantification showed that 100% of the original fragment was still present after exonuclease treatment, as was the case in the negative control which was not incubated with a Type II Cas protein-gRNA complexes (FIG. 4B, right panel, lane 1 vs lane 5).

Figures 5A, 5B:
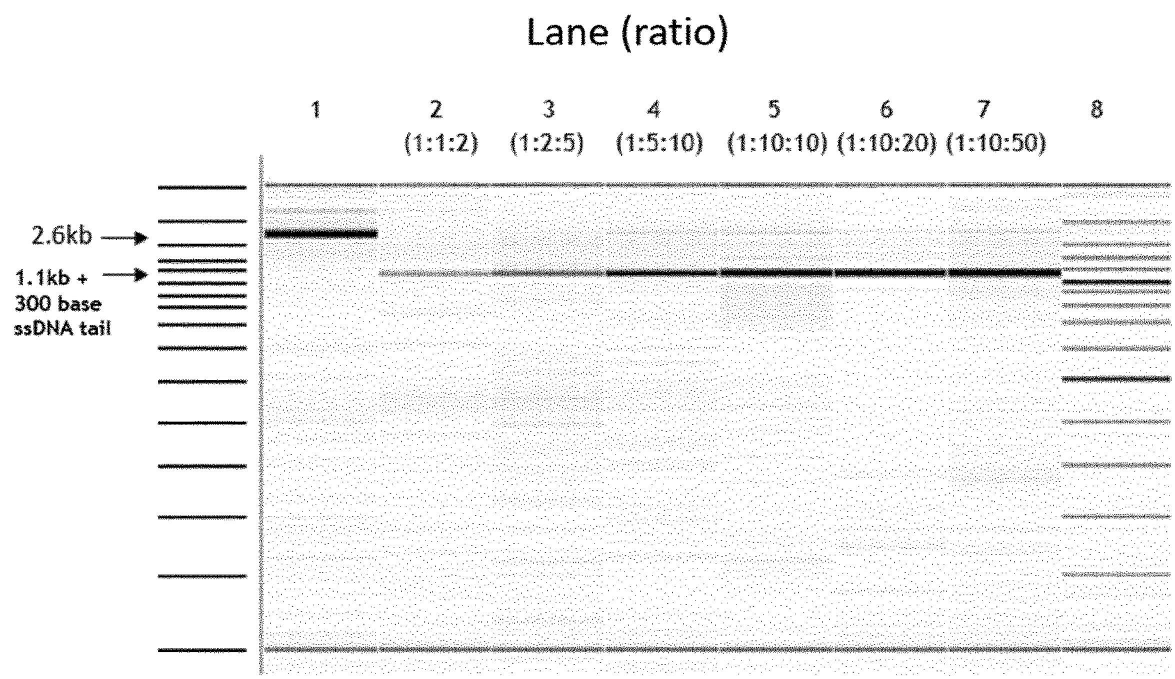

Example 7: Optimization of Reaction Conditions for Protection of the Nucleic Acid Fragment For these experiments, the 2.6 kb dsDNA fragment described in Example 3.1, comprising a hairpin at one end and a target region comprising a sequence for the RNA guide gRNA-Fmr1 #1 at the other end, was used. Different ratios of target nucleic acid:dCas9:gRNA were tested, as shown in FIGS. 5A and 5B. After incubating these nucleic acid molecules with the dCas9-gRNA complex, we supplemented the reaction mix with lambda exonuclease as well as the restriction enzyme PvuII, which cuts between the 5' end of the fragment and the gRNA-Fmr1 #1, to generate more free DNA ends. After this treatment, the expected size of the DNA fragment will be 1.2 kb with 300 bases of ssDNA at the 3' end (comprising an adjacent nucleic acid region, located between the PvuII site and the site recognized by the gRNA-Fmr1 #1). The proportion of protected fragments as compared to the original 2.6 kb fragment was determined by running the samples on a Fragment Analyzer® (AATI©) with the High Sensitivity NGS Fragment Analysis Kit (1 bp-6,000 bp), and calculating the areas under the curves (lane 1, FIG. 5A). Based on these results, the most optimal ratio of target nucleic acid:dCas9:gRNA is at least 1:10:50, resulting in almost 90% of fragments recovered (lane 7, FIG. 5A).

Figure 5C:
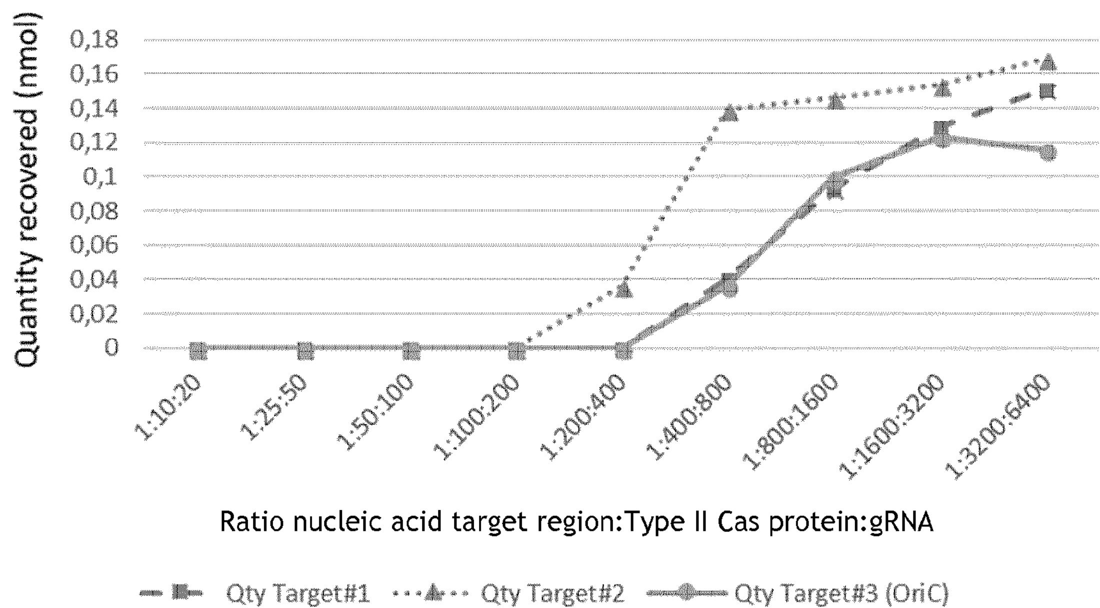
Figure 5D:
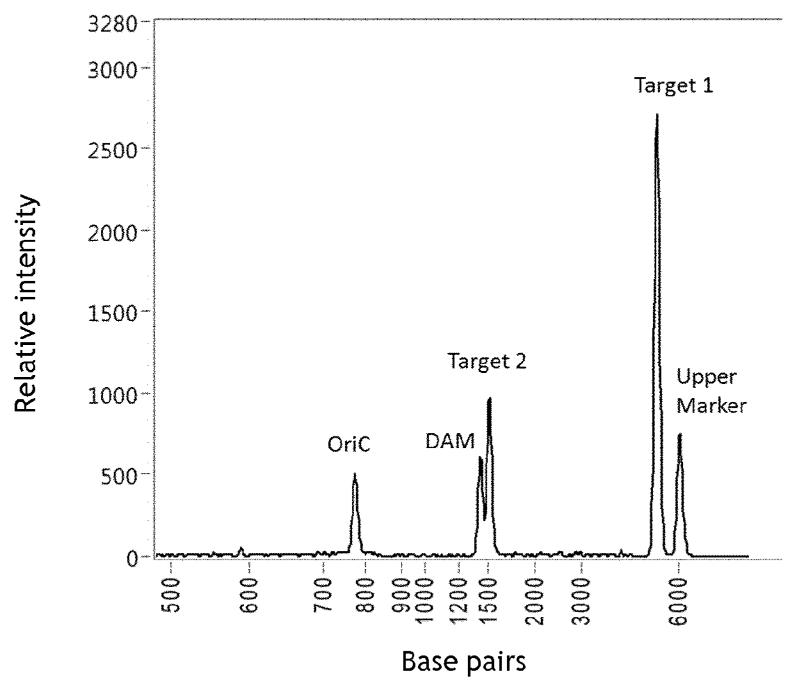

The dCas9 nuclease therefore surprisingly acts as an extremely efficient blocker of exonuclease initiation and digestion in appropriate optimized conditions. Similarly, Cpf1 also efficiently blocks exonuclease initiation when the PAM site is located within the target region and when used in appropriate conditions (FIG. 5C, 5D).

Figure 6A:
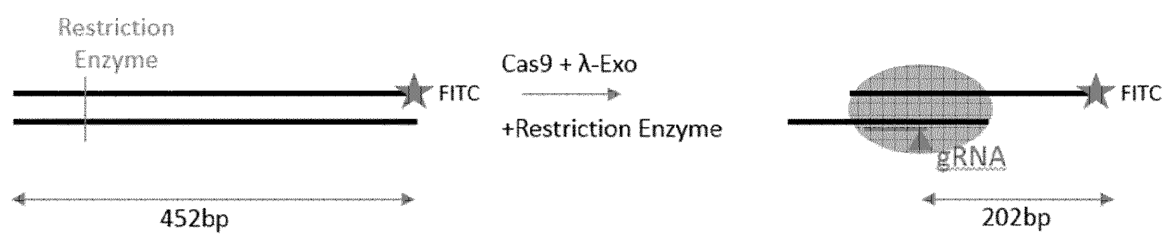
Figure 6B:
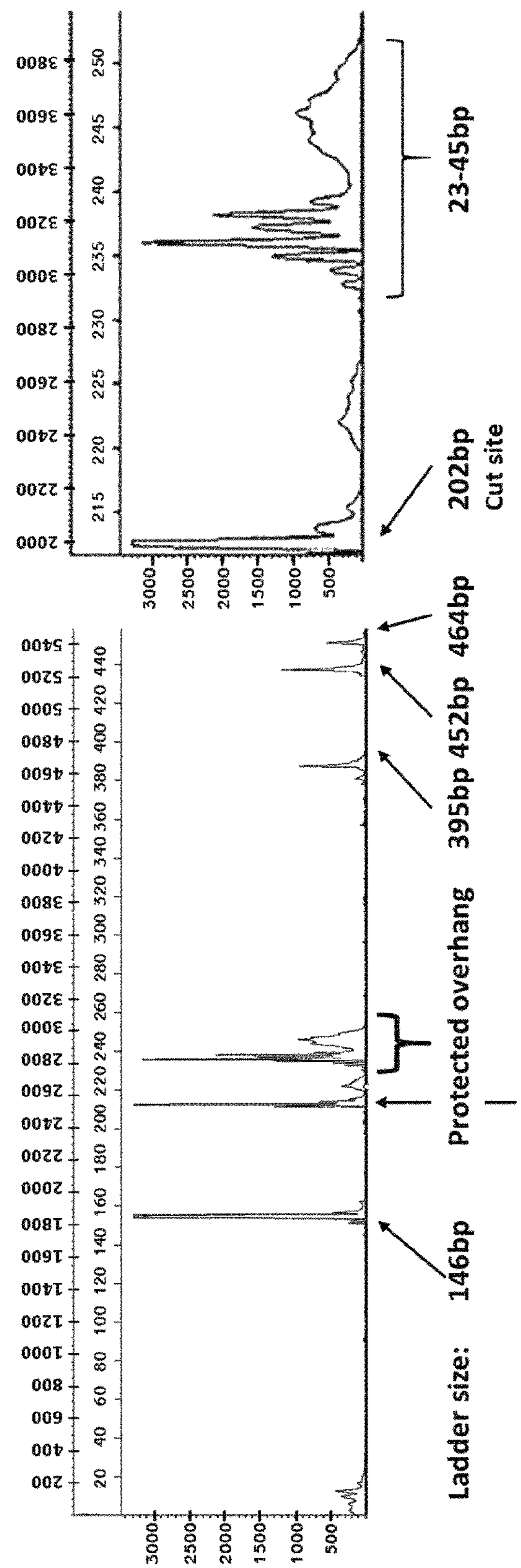

Example 8: Determination of the Length of the Target Region Protected by the Type II Cas Protein-gRNA Complex A 452 bp PCR product comprising a sequence in the target region that is complementary to the gRNA guide segment (as illustrated in FIG. 6A), was amplified using primers PS553 and PS554 (having sequences of SEQ ID NO: 16 and SEQ ID NO: 17, respectively). As PS554 has a BsaI restriction site, after digestion, the oligonucleotides PS495 and PS556 (having sequences of SEQ ID NO: 18 and 19, respectively) were ligated to add the FITC on the 3' end. The PCR product comprising the FITC molecule at the 3' end of the strand (SEQ ID NO: 15) was then contacted with the Cas9-gRNA complex comprising the gRNA-Fmr1 #1, followed by incubation with lambda exonuclease and one restriction enzyme as described in above in Examples 3 and 7. The precise size of the protected target region was quantified by running the samples on a capillary electrophoresis sequencer (ABI 3730) under denaturing conditions. The sample was pooled with ssDNA size markers labelled with FITC (FIG. 6B, left) allowing for determination of the size of the protected target region with single-base resolution (FIG. 6B, right). The FITC-labelled size markers also allowed quantification of each observed peak with high precision. The target region protected by Cas9-gRNA complex is between 23 and 45 bases, starting from the 5'-NGG-3' PAM (FIG. 6).

Example 9: Development of Strategies for the Isolation and Enrichment of a Target Region from a Genome Based on the results described above, various approaches were developed and tested, using either Cas9n or dCas9. As a proof of concept, a specific 5 kb DNA fragment was isolated from a sample of purified *E. coli* genomic DNA. As the size of the *E. coli* genome is approximately 5 million bases, each 5 kb fragment represents 0.1% of the genome.

9.1. Isolation of a Nucleic Acid Target Region Using a Type II Cas Protein Nickase

*E. coli* genomic DNA was digested with the non-palindromic restriction enzyme BsaI, to create different 4-base 5' overhangs at each cut site. This also served to linearize the gDNA. A synthetic hairpin adaptor (PS421, SEQ ID NO: 20) was specifically ligated to the complementary 5' overhang of the nucleic acid fragment comprising the target region that is to be enriched. The nucleic acid molecules were then incubated with Type II Cas protein-gRNA complex Cas9n-gRNA-*Ecoli*#1(SEQ ID NO: 6), wherein said Cas9n had the D10A substitution (FIG. 7A). As indicated previously, Cas9n (D10A) creates a nick 3 bases after the PAM NGG sequence on the strand that is complementary to the one containing the PAM sequence. After 1 hour, a cocktail of restriction enzymes comprising PvuII, EcoRI, and EcoRV was added to the reaction mixture to fragment the nucleic acid molecules, along with lambda exonuclease (FIG. 7B). All fragments having free ends that were not protected by the Cas9n-gRNA-*Ecoli*#1 complex and/or hairpin adaptor were digested.

The Cas9n-gRNA-*Ecoli*#1 complex was then digested with proteinase K and RNase A. The undigested target DNA consisted of the original target region comprising an adjacent region, located between the Cas9-gRNA-*Ecoli*#1 target region and the hairpin adaptor, and a long 3' tail on the other end. The strand with the tail also had a nick created by the Cas9 at the target site (indicated by the triangle in FIGS. 7A to 7D), while the complementary strand comprised 23-45 nucleotides extending 5' from the nick site (as indicated in FIG. 7B). The isolated nucleic acid (FIG. 7C) can then be used in further processing, reactions, or analysis, as described herein.

9.2. Hairpin Construction by Strand Displacement

Further to the method of 9.1, the isolated nucleic acid molecule may be used for hairpin construction. Given the variable length of the protected 5' ssDNA tail, further processing is necessary. In particular, the DNA strand nicked by Cas9n was displaced using strand displacement, by incubating the isolated nucleic acid with an oligonucleotide (PS422, having the sequence of SEQ ID NO: 21) at room temperature. This allowed recovery of the dsDNA target with a short 5' ssDNA tail of 23 to 45 nucleotides (corresponding to the length of the sequence protected by the Cas9), as shown in FIG. 7E. The oligonucleotide for initiating strand displacement was designed to be at least 50 nucleotides away from the 3' end of the PAM, to compensate for the variable length of nucleic acid that is protected by the Cas9-gRNA complex.

Remaining oligonucleotides and the displaced complementary strand were then eliminated by exonuclease I digestion for 1 hour at 37° C., followed by enzyme inactivation at 75° C. for 15 minutes (FIG. 7E). As exonuclease I exclusively digests single-stranded DNA in the 3' to 5' direction, the excess single-stranded oligonucleotides were degraded, without any effect on 5' overhangs or double-stranded DNA. The 23-45 nucleotide 5' overhang then served as a template to hybridize and ligate oligonucleotides to construct the final hairpin structure (FIGS. 7F and 7G). Specifically, an oligonucleotide complementary to the 5' overhang that is left by the nickase (e.g. PS599, having the sequence of SEQ ID NO: 22) is incubated with the reaction at room temperature. This oligonucleotide is designed to comprise at least the 43 nucleotides protected by the Cas9-gRNA complex and at least 20 nucleotides allowing for a second oligonucleotide to hybridize and at least 40 nucleotides of ssDNA for anchoring the hairpin to a surface by hybridization. The 5' end of this oligonucleotide is then ligated with the 3' end of the isolated region (FIG. 7F).

A second oligonucleotide (e.g. PS598, having the sequence of SEQ ID NO: 23), biotinylated at the 5' end, is then hybridized to the first oligonucleotide (FIG. 7G). The nick is filled by a DNA polymerase and then sealed by a ligase according to well-known techniques.

9.3. Isolation of a Nucleic Acid Target Region Using a Catalytically Dead Type II Cas Protein First, crRNA-tracrRNA duplexes were prepared by mixing 20 μM of crRNA with 10 μM of tracrRNA (IDT) in 1X Synthego annealing buffer, to generate the Cas9 gRNA-*Ecoli*#1 comprising the target specific sequence according to SEQ ID NO: 6). The mixture of crRNA (generic sequence of SEQ ID NO: 24, wherein the 'N' nucleotide stretch comprises the target specific sequence) and tracrRNA (SEQ ID NO: 25) was heated at 78° C. for 10 min, cooled at 37° C. for 30 min and then allowed to cool slowly to room temperature (approximately 15 min). This procedure gives a final concentration of the gRNA of 10 μM, with the crRNA being in a 2-fold excess as compared to the tracrRNA.

For experiments in which we used 100 ng of *E. coli* DNA, this corresponds to 33 fmol of the target. By adding 1 μg of human genomic DNA, the number of potential target sites for the dCas9/gRNA complex is significantly increased. Consequently, the ratio of the dCas9-gRNA complex as compared to the target must also be increased.

The dCas9:gRNA complex is formed by incubating, for each gRNA, 100 nmol of the Cas9 dead with 250 nmol of annealed crRNA-tracrRNA (or gRNA). The reaction is left for 10 min at room temperature in the Cas9 Reaction Buffer (20 mM Tris-acetate, 10 mM Magnesium acetate, 50 mM Potassium acetate, 0.1% Triton X-100, 100 μg/ml BSA, pH 7.9 at 25° C.).

As described above in section 9.1, *E. coli* genomic DNA is digested with the non-palindromic restriction enzyme BsaI, to create different 4-base 5' overhangs at each cut site and to linearize the gDNA. A synthetic hairpin adaptor (PS421 of sequence SEQ ID NO: 20) was specifically ligated to the complementary 5' overhang of the nucleic acid fragment comprising the target region to be enriched. The *E. coli* genomic DNA was then mixed with human gDNA (100 ng of *E. coli* gDNA and 1 ug of human gDNA), to determine if nucleic acid isolation is successful in samples comprising complex mixtures of nucleic acid molecules.

The DNA mixture is added to the solution comprising the dCas9:gRNA complex and incubated at 37° C. for 1 hour, to form the dCas9:gRNA-nucleic acid complex shown in FIG. 8A. The dCas9-gRNA complex lacks nucleic acid cutting activity, but retains its recognition and binding properties.

All fragments having free ends that were not protected by the dCas9-gRNA-*Ecoli*#1 complex and/or the hairpin adaptor were digested (FIG. 8B). The nuclease treatment (5U of lambda exonuclease and a restriction enzyme cocktail of PvuII/EcoRV/EcoRI/BamHI incubated at 37° C. for 1 hour) removes the 5' strand and leaves a 3' ssDNA tail. The lambda exonuclease and restriction enzymes are then inactivated at 80° C. for 20 min.

The protected nucleic acid molecule comprising the nucleic acid target region therefore consists of the original target region comprising an adjacent region, located between the Cas9-gRNA-*Ecoli*#1 target region and the hairpin adaptor, and a long 3' tail on the other end. The dCas9:gRNA complex is then removed from its DNA target by treatment with 10 μg of RNase A at 37° C. for 15 min, followed by the addition of 20 μg of Proteinase K and incubation for 15 min at 37° C. The resulting DNA fragment is then purified using magnetic beads (via either SPRI select from Beckman Coulter or KAPA beads from Roche; both give similar results).

9.4. Isolation of a Nucleic Acid Target Region Using Two Type II Cas Protein-gRNA Complexes The same method was followed as described above in sections 9.1 and 9.3. However, instead of ligating a synthetic hairpin adaptor to the complementary 5' overhang of nucleic acid molecules, the nucleic acid molecules were instead incubated with two Type II Cas protein-gRNA complexes: Cas9-gRNA-*Ecoli*#1 and Cas9-gRNA-*Ecoli*#2, as shown in FIG. 9A schemas 1 and 2. The *Ecoli*#1 and *Ecoli*#2gRNA correspond to the sequence of SEQ ID NOs: 6 and 7, respectively. The target regions of the two Type II Cas protein-gRNA complexes are separated from one another by 4909 nucleotides.

Either two dCas9 proteins or two Cas9n proteins were used. The same method was followed as described above in section 9.3.

When using two dCas9 or Cas9n proteins instead of a Cas9 protein and a hairpin adaptor, the undigested target DNA consisted of the original target region comprising an adjacent region, located between the Cas9-gRNA-*Ecoli*#1 target region and the Cas9-gRNA-*Ecoli*#2 target region, and a long 3' tail on the either side, as illustrated in FIG. 9A schemas 1 and 2.

After isolation, said target region can be further treated to produce a hairpin structure with hybridization, fill-in, and ligation reactions according to the method of 9.1.

Alternatively, after isolation, when using two Cas9n proteins, said target region can be further treated to generate an undigested target DNA including the original target region comprising an adjacent region, and a short 5' ssDNA tail of 23 to 45 nucleotides (corresponding to the length of the sequence protected by the Cas9) on either side, according to the method of 9.2 (cf. FIG. 9A, schema 2).

Figure 9D:
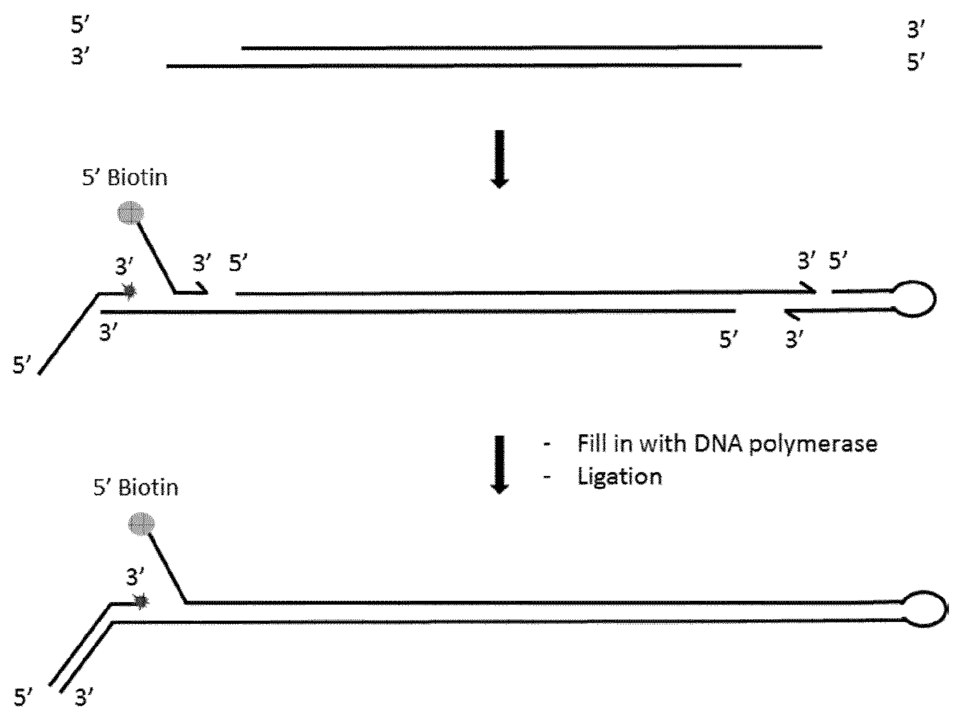
Figure 9E:
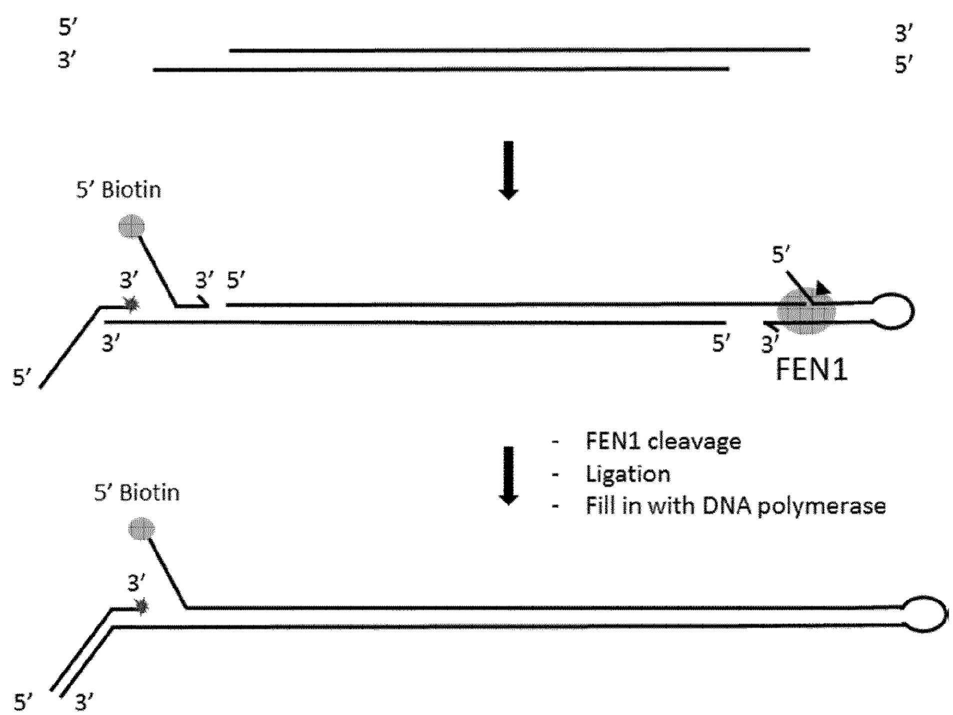

9.5. Isolation of a Nucleic Acid Target Region Using Cpf1-crRNA and Cas9-gRNA Complexes In addition to using the Type II Cas protein Cpf1 to protect a target region from exonuclease treatment (i.e. when the PAM sequence is included within the target region), as illustrated in FIG. 9B, it is also possible to use Cpf1 as a site-specific endonuclease when the PAM sequence is included within this region to produce the isolated fragments (as illustrated in FIG. 9C). The fragments that do not contain PAM sequence will serve as substrate for the exonuclease treatment. In this example, 1 ug of *E. coli* genomic DNA is incubated with Cpf1-crcrRNA-*Ecoli*#4 and 5 (SEQ ID NO: 49 and 50) for 30 minutes before adding the lambda exonuclease as well as ExoI exonuclease. After inactivation using either proteinase K or EDTA, the fragments are purified and incubated with dCas9-gRNA-*Ecoli*#1 and 2 (SEQ ID NO: 6 and 7) for 30 minutes. Then, lambda exonuclease is added to produce the 3' ssDNA overhang at both ends. After inactivation either by proteinase K or EDTA, the final isolated regions are purified. These fragments may then be then processed into functional hairpins, as illustrated in FIG. 9D or 9E.

Alternatively, both the Cpf1-crRNA*Ecoli* #12 and Cpf1-crRNA*Ecoli*#13 complexes (crRNAs having the sequences of SEQ ID NO: 57 and 58, respectively) can be incubated at the same time as the dCas9-gRNA*Ecoli* #1 and dCas9-gRNA*Ecoli*#2(gRNAs having the sequences of SEQ ID NO: 6 and 7, respectively) assuming that the PAM sequences of the Cpf1 sites flanking the region to be isolated are located outside of the target region itself (i.e. as indicated by the arrows in FIG. 9C, schema 1). After a 30 minute incubation, lambda exonuclease is added to the mix to generate the 3' ssDNA extension until the Cas9 binding position. Following inactivation with either proteinase K or EDTA, the isolated fragments can be purified and used to produce hairpins as in FIG. 9D or 9E.

9.6. Hairpin Construction by Oligonucleotide Hybridization and Ligation

The structure of the nucleotide fragment recovered following the protection reaction with the dCas9:gRNA complex depends on the protection strategy used (for example, as described in section 9.3 or 9.4, above). If the dCas9:gRNA complex is used to protect only one end of the target DNA, with the other end being shielded by the specific ligation of a hairpin structure, a 3'-ssDNA end is produced at only one end of the nucleotide fragment (section 9.3). The undigested target DNA in this case therefore consists of the original target region comprising an adjacent region, located between the dCas9-gRNA complex target region and the hairpin adaptor, and a long 3' tail on the other end.

Alternatively, if a dCas9:gRNA complex is used to protect both ends (or either side of an adjacent region), as described in section 9.4 and 9.5, the resulting molecule will be a double stranded DNA with 3' single stranded regions on each side (the length of these overhangs will depend on the restriction enzymes used).

These isolated nucleic acids can then be used in further processing, reactions, or analysis, as described herein. In particular, the ssDNA tails can be used as templates upon which Y-shaped primers (e.g. for bead and surface attachment) and/or hairpin adaptors can be subsequently hybridized.

Further to the method of 9.3, one or more oligonucleotides were hybridized to the 3' single-stranded overhang generated by lambda exonuclease digestion, to create a desired nucleic acid structure. As a specific example, to produce the Y-shape, the isolated DNA described in 9.3 is first incubated with 0.2 nM of the oligonucleotide PS645 (sequence of SEQ ID NO: 27). PS645 is biotinylated at its 5' end, while its 3' end is complementary to the sequence located roughly 50 bases from the PAM sequence. An oligonucleotide (e.g. PS647, sequence of SEQ ID NO: 28) containing a stem loop and a complementary sequence at least 50 bases from the PAM sequence is located at the other end of the protected fragment. Said oligonucleotides were hybridized at least 50 nucleotides away from the PAM NGG site to compensate for the variability in the length of the protected region (FIG. 8C). The gaps were then sealed by performing fill-in reactions and ligations to the 5' end of the desired fragments, using Bst full length DNA polymerase and Taq DNA ligase (FIGS. 8D and 8E). A final step of exonuclease I treatment was used to eliminate all of the non-hybridized oligonucleotides and to remove remaining 3' single-stranded DNA tails of the targeted nucleic acid fragment (FIG. 8F).

When the Type II Cas protein-gRNA complex Cpf1-crRNA is used to isolate target nucleic acid fragments of interest (as in example 9.5), the 3' end of the ssDNA is known and therefore no ExoI exonuclease treatment is required to remove remaining 3' single-stranded DNA tails, in contrast to what is illustrated in FIG. 8F. Rather, on each side of the target nucleic acid molecule we can hybridize an oligonucleotide which has a sequence complementary to the Cpf1-crRNA sequence and either a specific sequence, for example to construct a surface oligonucleotide for the attachment of the hairpin, or a loop structure (for example, PS1095 for surface attachment and PS1096 for loop structure in the case of target #1, said oligonucleotides having the sequence of SEQ ID NO: 59 and 60, respectively). Gaps may simultaneously be filled-in, along with hybridization of the biotin oligonucleotide PS645, SEQ ID NO: 27 (as depicted in FIGS. 9D and 9E). As the Cpf1 cleavage position varies, it is preferable to hybridize a "template oligonucleotide" having a known sequence to the 3' end and extend the 3' end. Preferably, said "template oligonucleotide" has the same sequence as an oligonucleotide attached to a surface. In this case, the "template oligonucleotide" is advantageously removed by NaOH treatment, with the newly extended 3' single-stranded end being complementary to the oligonucleotide attached to a surface.

Furthermore, the ssDNA tails can be used to hybridize specific oligonucleotides with a "adaptor" sequence, which could be specific to a particular sequencing platform.

Further to the method of 9.4, a hairpin structure can then be specifically added to one of the ssDNA tails using hybridization, fill-in, and ligation reactions, as described above in sections 9.1 and 9.3. A Y-shaped structure can then be obtained as described above.

CONCLUSIONS

The targeted DNA molecules were isolated with very high specificity when using either a single Cas9-gDNA complex and a hairpin adaptor, or when using two Cas9-gDNA complexes and even when using both Cpf1 and Cas9 Type II proteins. Indeed, target region isolation was 100% specific for the target 5 kb DNA fragment from *E. coli* genomic DNA, representing >1,000-fold enrichment.

Example 10: Isolation of a Nucleic Acid Target Region Using a Cpf1 Protein

Figure 10A:
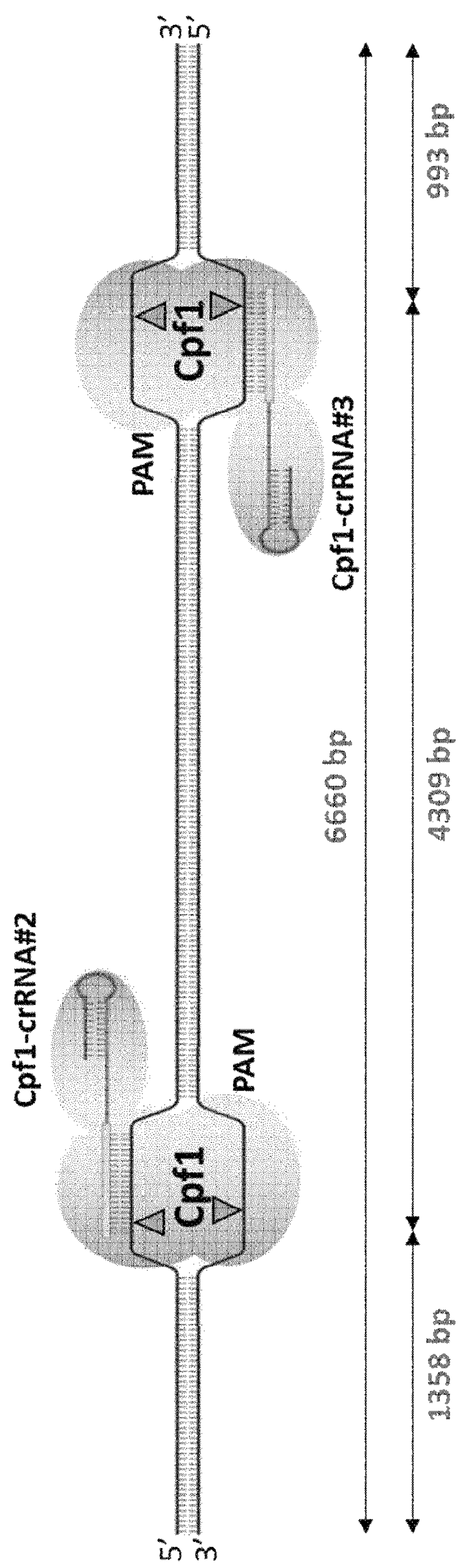

Cpf1 has the same binding and protection capacity from exonuclease digestion as Cas9. We determined the efficiency of cleavage by incubating Cpf1-crRNA complexes with a 6.6 kb PCR product, having the sequence of SEQ ID NO: 32. The PCR product was obtained by PCR amplification of a fragment of the *E. coli* genome using primers PS340 and PS860 (SEQ ID NOs: 29 and 30, respectively) according to standard techniques. The PCR product was then incubated with two different Cpf1-crRNA complexes at various ratios (Cpf1-crRNA #2 or Cpf1-crRNA #3 at 1:10:20, 1:20:40, 1:40:80 ratios, corresponding to DNA:Cpf1:crRNA) and for different incubation times (30 and 60 minutes for the Cpf1-crRNA #2 and only 30 minutes for the Cpf1-crRNA #3). The target sequences of the gRNAs are located roughly 1 kb from either end of this PCR fragment, as illustrated in FIG. 10A. The gRNA sequences of crRNA #2 and crRNA #3 correspond to SEQ ID NO: 8 and 9, respectively. The corresponding crRNA generic sequence is shown in SEQ ID NO: 33, wherein the target specific sequence may be any sequence (represented by 'N').

After incubation at 37° C. in Cpf1 Reaction Buffer (50 mM Potassium acetate, 20 mM Tris-acetate, 10 mM Magnesium acetate, 100 μg/ml BSA, 5 mM DTT, pH 7.9), the Cpf1-crRNA complex was removed from the DNA by adding Proteinase K. The different reactions were analysed on a Fragment Analyzer™ Automated CE System, and cleavage efficiency was determined (cf. FIG. 10B).

Figure 10B:
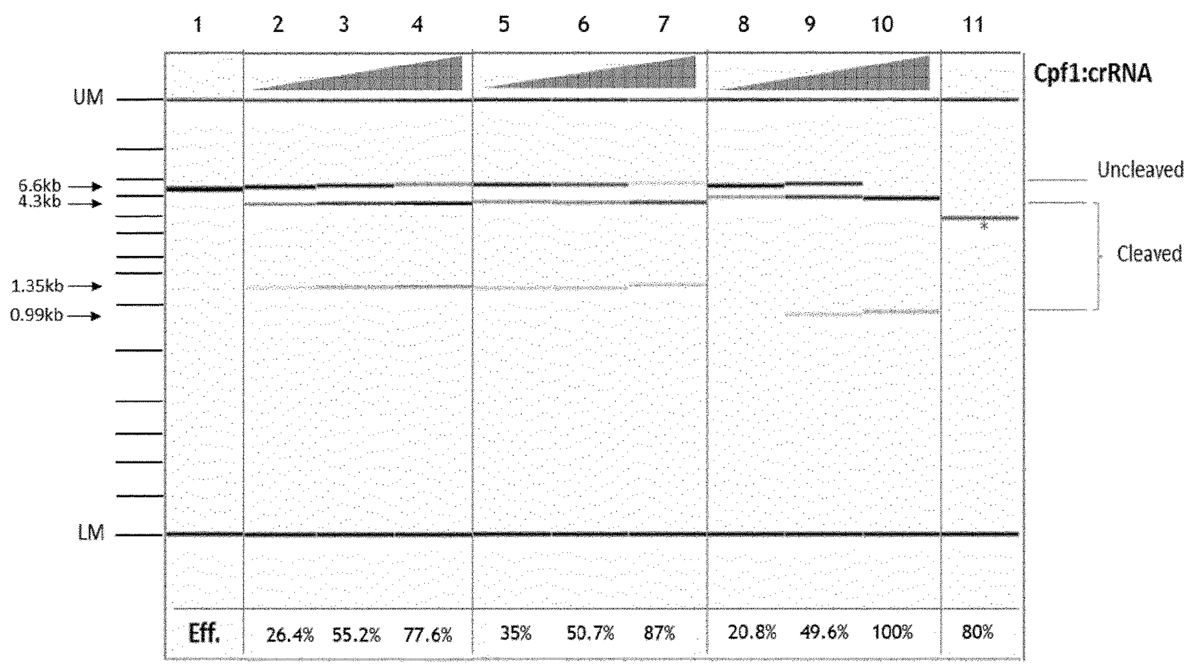

Based on these results, we were able to determine that the optimal ratio of DNA:Cpf1:crRNA is at least 1:40:80 to reach more than 87% efficiency of protection from cleavage for either of the two tested gRNAs (FIG. 10B, lanes 7 and 10). Furthermore, an incubation time of 60 min is better than 30 min (FIG. 10B, lanes 2-4 vs 5-7). We have also tested the efficiency of protection of these two gRNAs on the same PCR fragment by simultaneously incubating the two guides (crRNA #2 and crRNA #3) at a ratio of 1:80:80:80 (DNA:Cpf1:crRNA #2:crRNA #3). After 60 min, lambda exonuclease along with Exonuclease I were added to digest any DNA that was not protected by Cpf1. The lambda exonuclease and exonuclease I were then heat inactivated at 80° C. for 20 minutes before adding Proteinase K to degrade the Cpf1:crRNA complex as well as the exonucleases. The remaining amount of dsDNA was determined on a Fragment Analyzer™ Automated CE System (FIG. 10, lane 11). Using these conditions, we were able to recover more than 80% of the target region, comprising the adjacent region located between the two Cpf1 sites on the PCR fragment.

Example 11: Multiplex Isolation of a Target Region Using the dCas9 Type II Cas Protein 5 μg of *E. coli* genomic DNA was digested with the non-palindromic restriction enzyme BsaI, to create 4-base 5' overhangs for each targeted region for isolation. This step also served to linearize the gDNA. A synthetic hairpin adaptor (PS421, SEQ ID NO: 20) was ligated to the complementary 5' overhang of the nucleic acid fragments comprising the targeted region to be enriched. The resulting DNA was then incubated into a single reaction tube with two dCas9:gRNA complexes specific for the two targets. The gRNA-*Ecoli*#1 was designed for target #1 (5 kb, comprised in sequence SEQ ID NO: 31) and the gRNA-*Ecoli*#3 for target #2 (1.2 kb, comprised in sequence SEQ ID NO: 34). Sequences of gRNA-*Ecoli*#1 and gRNA-*Ecoli*#3 are shown in SEQ ID NOs: 6 and 10, respectively. The ratio of DNA:dCas9:gRNA used was 1:100:250 for each target.

After 60 min at 37° C., λ exonuclease was added to the same reaction tube to remove the 5'-strand of DNA, followed by heat inactivated at 80° C. for 20 minutes. Then, RNase A and proteinase K were added to the same reaction tube to degrade the DNA:dCas9:gRNA complex. To produce a hairpin from these fragments, oligonucleotides PS645 and PS648 (SEQ ID NO: 27 and 32, respectively) were hybridized and ligated to each *E. coli* target. Both targets were successfully identified in the preparation by using a fingerprinting oligonucleotide of 4 bases (5'-CAAG-3') on the SIMDEQ platform (platform precision: +/−12 bases), as shown in FIGS. 11A and 11B. The extra peak observed in FIG. 11A was not seen in subsequent replicates performed on this target region.

The same bead tested with the fingerprinting oligonucleotide of 4 bases (5'-CAAG-3') in FIG. 11B was also tested with the monoclonal antibody clone which is specific for the modified base 5-methylcytosine (5-mC) (ICC/IF from Diagenode, used at a dilution of 1/1000). Target #2 contains three predicted 5-mC, all of which were successfully detected on the DNA hairpin attached to this bead at the expected locations.

Example 12: Multiplex Isolation of a Target Region Using the Cpf1 Type II Cas Protein Multiple nucleic acid target sequences were isolated simultaneously by multiplex using Cpf1-crRNA complexes. Briefly, we incubated 1 ug of *E. coli* genomic DNA with various Cpf1-crRNA complexes (SEQ ID NO: 49 to 56) to isolate 4 different target regions (with each target region comprising two target regions recognized by Cpf1-crRNA complexes and a central adjacent region) of various sizes (from 700 bp to 5000 bp, comprised within SEQ ID NOs: 31, 34, 47 and 48). We used a ratio of 1:1400:2800 (DNA:Cpf1:crRNA) and incubated the genomic DNA with these complexes for 30 minutes, after which both lambda exonuclease (40 units) and ExoI exonuclease (40 units) was added to the tube. After an incubation of 30 more minutes, the reaction was stopped with either proteinase K or EDTA and the fragments purified. The isolated fragments were resolved on a Fragment Analyzer® (AATI©) with the High Sensitivity NGS Fragment Analysis Kit (1 bp-6,000 bp) and all 4 expected fragments were observed (FIG. 5D).

Example 13: Isolation of the Human FmrI Region Using Cpf1 and Cas9 Type II Cas Proteins To determine if our protection assay also works on human genomic DNA, we performed an enrichment experiment for the 5' UTR region of FmrI, which contains both a repeat element and a CpG island, both implicated in Fragile X-related syndromes. We first contacted the FmrI region with Cpf1-crRNA-FmrI #2 and Cpf1-crRNA-FmrI #3 (SEQ ID NOs: 61 and 62, respectively) by incubating these complexes with 5 ug of human genomic DNA. After 30 minutes of incubation, we added lambda exonuclease as well as ExoI exonuclease (40 units of each per pg of DNA). After inactivation by proteinase K, we incubated the purified fragment with dCas9-gRNA-Fmr1 #1 and dCas9-gRNA-Fmr1 #2(SEQ ID NOs: 3 and 4, respectively) for 30 minutes, followed by lambda exonuclease treatment. The reaction was stopped with either proteinase K or EDTA and the fragments purified.

The hairpin structure was constructed as illustrated in FIG. 9D. Briefly, using the Cpf1-crRNA cleavage position, we hybridized an oligonucleotide specific for hairpin surface attachment with a 3' phosphate to prevent elongation (PS1161, SEQ ID NO: 63) at one end, and an oligonucleotide creating the loop structure (PS1162, SEQ ID NO: 65) on the other end. An oligonucleotide labelled with biotin was also hybridized to the ssDNA overhang at a position adjacent to the oligonucleotide specific for hairpin surface attachment (PS601, SEQ ID NO: 64), as illustrated in FIG. 9D (middle panel). The gap fill-in reaction was performed at 50° C. in Buffer (20 mM Tris-HCl, 10 mM $(NH_4)2SO_4$, 10 mM KCl, 2 mM $MgSO_4$, 0.1% Triton® X-100, pH 8.8, 25° C.) with 0.2 μM of each oligonucleotide, 0.25 U of the Bst DNA Polymerase, Full Length along with 40 U of Taq DNA Ligase supplemented with 1 mM NAD for 10 min. The elimination of single-stranded DNA oligonucleotides was achieved by adding 20U of Exonuclease I for 30 min at 37° C. The reaction was then purified using magnetic beads.

Figure 12A:
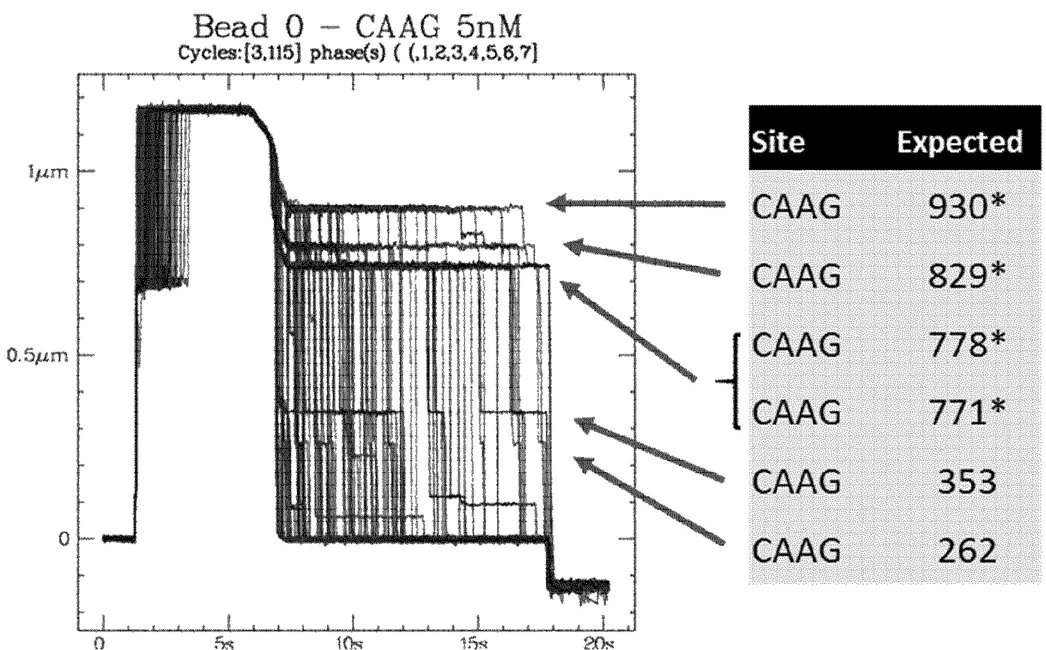
Figure 12B:
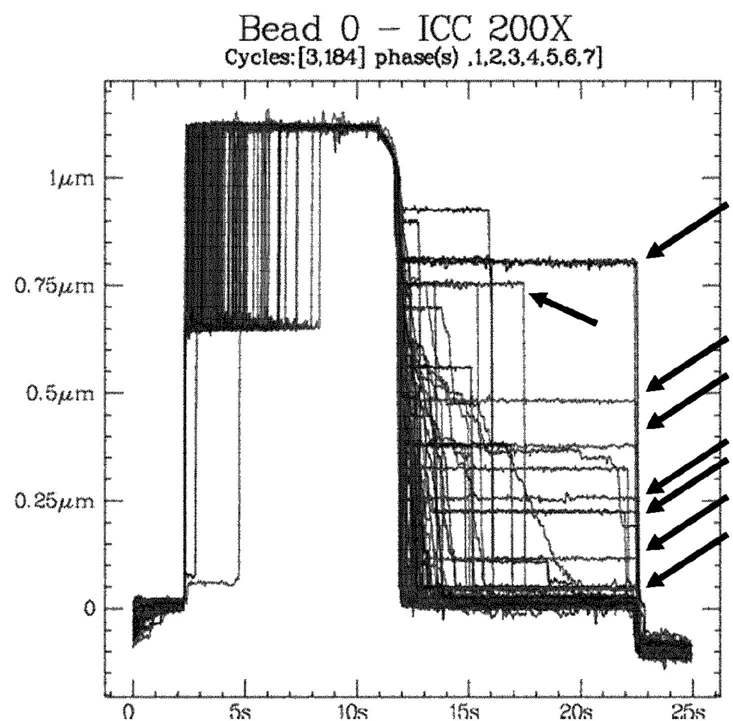

FMR1 DNA molecules were successfully identified in the preparation by using a fingerprinting oligonucleotide of 4 bases (5'-CAAG-3') on the SIMDEQ platform (platform precision: +/−12 bases), as shown in FIG. 12A. 5mC base modifications were also successfully identified within the molecule (using specific antibodies against 5mC, clone ICC/IF from Diagenode), as shown in FIG. 12B (base modifications indicated by the arrows).

Example 14. Production of a Sequencing Library from Human Genomic DNA for 15 Different Targets from 13 Different Samples In addition to FMR1 (described in example 13 above), 14 human genomic regions known to be either epigenetic markers for cancer or composed of STR (Short-tandem repeats) known to cause diseases in humans were selected (see FIG. 13A; sequences of these regions correspond to SED ID NOs: 66 to 80). As described in example 4, gRNA binding and protection efficiency are tightly linked to the efficiency of cleavage of the wild-type enzyme. For each target, two Cpf1 guide RNAs were designed wherein the PAM sequence was located within the target (one on each side of the central target region having the sequence of SEQ ID NO: 66 to 80, with the crRNAs having the sequences of SEQ ID NO: 81 to 108) and four different Cas9 guide RNAs were designed at least 100 bp from the Cpf1 cleavage site (2 sites flanking each side of the central target region, Cas9 gRNAs having the sequences of SEQ ID NO: 137 to 192, with gRNAs #1 and #2 located on one side of the central target region and gRNAs #3 and #4 located on the other side of the central target region). In all cases, the sites recognized by the Cas9 gRNAs were located within the region flanked by the Cpf1 gRNAs, as illustrated in FIG. 9B. Cleavage efficiency of each guide RNA was determined on a PCR product. PCR primers were designed to amplify each target region along with an additional flanking 200 bp to 800 bp outside the Cpf1 cleavage site, and were used to validate the cleavage efficiency of the Type II Cas protein-gRNA complexes (PCR primers corresponding to SEQ ID NO: 109 to 136). The PCR fragments of 2000 to 3000 base pairs were obtained using a GC-rich polymerase (PrimeSTAR GXL DNA Polymerase from Takara bio).

Figure 13B:
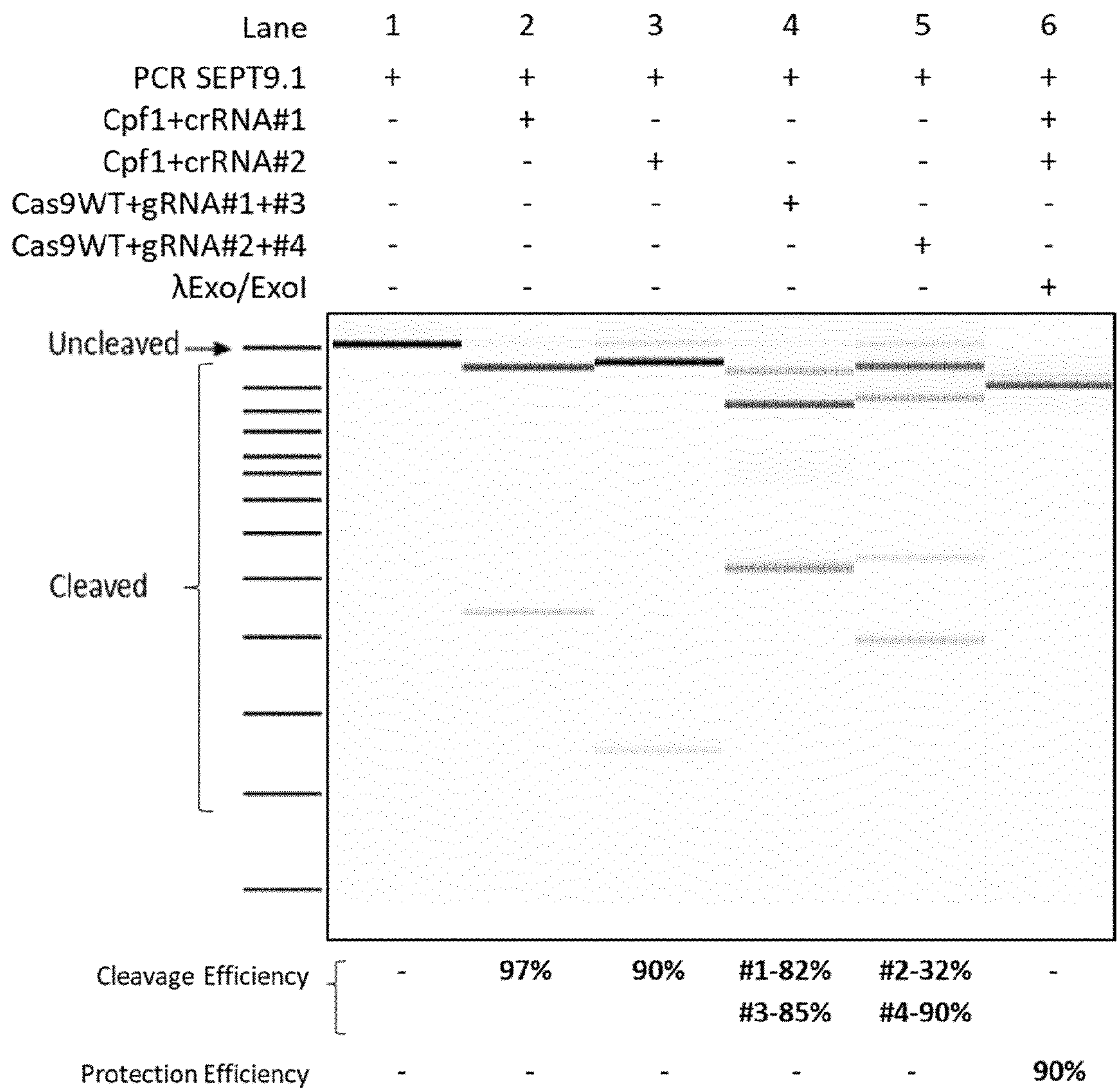

FIG. 13B shows an example of quantification of the cleavage and protection efficiency of Cpf1-crRNA and Cas9-gRNA for one target (SEPT9.1). The PCR fragment was incubated separately with Cpf1-crRNA complex #1 (left side of the target) or #2 (right side of the target) (FIG. 13B, lane 2 and lane 3). To test Cas9-gRNA complex efficiency, we tested the two guides simultaneously (one on each side of the target) as they produced different fragment sizes that allowed us to determine their corresponding efficiency. Lane 4 showed the testing of Cas9-gRNA #1 and #3 and lane 5 corresponds to Cas9-gRNA #2 and #4. Efficiency was calculated according to the quantity cleaved divided by the total amount of PCR (Control sample, lane 1). Finally, we also tested Cpf1-crRNA protection by incubating the Septin 9 PCR fragment with both Cpf1-crRNA for 30 minutes followed by a treatment with lambda exonuclease as well as exonuclease I (lane 6).

The cleavage efficiency of all Cpf1-crRNA and Cas9-gRNA complexes is listed in FIG. 13C. The efficiency of almost all Cpf1-cRNA is more than 90%, although this is not the case for all Cas9-gRNA. With the exception of the NDRG4.2 CpG island, it was possible to find a good Cas9 guide on each side of the targeted region. Optimization to improve efficiency for all those gRNAs is still possible (for example, by increasing the quantity of Cas9:gRNA complex as observed in FIG. 5C). It is also possible to use two gRNAs on each side of the target to increase efficiency of the protection from exonuclease, as shown in FIG. 1C.

Once the most efficient Cpf1 and Cas9 guide RNAs were determined, we pooled the Cpf1:crRNA as well as dCas9:gRNA for all the targets into a single tube. Genomic DNA from 13 different samples (5 ug of DNA for 5 different FmrI samples with various numbers of repeat, 5 ug of DNA of 5 different DMPK samples with various numbers of repeat and 1, 5 and 10 ug of control HEK DNA) was incubated with Cpf1:crRNA pools at a ratio of target DNA:Cpf1:crRNA of 1:12000:24000 for 30 minutes followed by the addition of lambda exonuclease and ExoI. After inactivation using proteinase K, the sample was purified and incubated with the pool of dCas9:gRNA at a ratio of target DNA:dCas9:gRNA of 1:10000:20000 for 30 minutes followed by the addition of lambda exonuclease, thereby producing fragments with single stranded DNA 3' overhangs as shown in FIG. 9B. Following inactivation with proteinase K and purification, adapters were ligated specifically to each isolated target region for downstream sequencing. In the present case, adaptors appropriate for sequencing using a Pacific Biosciences instrument were ligated, said adaptors containing a barcode on one side for each experimental condition (an example of the sequence of the adapters with a barcode is provided in SEQ ID NO: 193, while a sequence without a barcode for the other side is provided in SEQ ID NO: 194, with the gene specific sequences corresponding to SEQ ID NO: 195 to 224 and SEQ ID NO: 225 to 240 for the barcodes).

The invention claimed is:

1. A method of isolating a target region of a nucleic acid molecule, said method comprising the steps of:

a. contacting a population of nucleic acid molecules with at least one Type II Cas protein-gRNA complex, wherein said gRNA comprises a guide segment that is complementary to a sequence comprised in the target region of at least one nucleic acid molecule, thereby forming a Type II Cas protein-gRNA-nucleic acid complex, b. contacting the population of nucleic acid molecules comprising the Type II Cas protein-gRNA-nucleic acid complex of step a) with at least one enzyme having exonuclease activity, thus degrading nucleic acid molecules that are not comprised in the Type II Cas protein-gRNA-nucleic acid complex, and c. isolating said target region from the Type II Cas protein-gRNA-nucleic acid complex formed in step a) after step b).

2. The method of claim 1, wherein said Type II Cas protein is Cas9 or Cpf1.

3. The method of claim 1, wherein said enzyme having exonuclease activity is a lambda exonuclease and/or exonuclease I (Exo I).

4. The method of claim 1, wherein at least one site-specific endonuclease cleaving outside of the target region is added prior to step b).

5. The method of claim 1, wherein step c) comprises the addition of EDTA and/or at least one protease.

6. The method of claim 1, further comprising linearization and/or fragmentation of said population of nucleic acid molecules prior to step b).

7. The method of claim 1, wherein the target region comprises a repeat region, a rearrangement, a duplication, a translocation, a deletion, or a modified base.

8. The method of claim 1, wherein the ratio of target nucleic acid:Type II Cas protein:gRNA is at least 1:10:10.

9. The method of claim 1, further comprising step d) wherein at least one single-stranded nucleic acid molecule is hybridized to a single-stranded region of the target molecule of step c).

10. The method of claim 9, wherein said single-stranded nucleic acid molecule hybridizes at least 50 nucleotides from a Type II Cas protein protospacer adjacent motif (PAM).

11. The method of claim 9, further comprising step e), wherein strand displacement is performed from said at least one single-stranded nucleic acid molecule.

12. The method of claim 9 further comprising step e), wherein said single-stranded nucleic acid molecule is extended by polymerization and is ligated to a double-stranded nucleic acid molecule.

13. The method of claim 1, wherein prior to isolation the nucleic acid target region comprises less than 10% of the total initial nucleic acid in a sample.

14. The method of claim 1, wherein at least two target regions are isolated.

15. The method of claim 1, further comprising a step of contacting the population of nucleic acid molecules of step a) with at least one protector molecule prior to step b).

16. The method of claim 15, wherein said protector molecule is a hairpin adaptor or a site-specific endonuclease.

17. The method of claim 16, wherein said site-specific endonuclease is selected from the group consisting of a transcription activator-like effector nuclease, a zinc-finger protein, and at least one additional Type II Cas protein-gRNA complex.

18. The method of claim 1, wherein step b) further comprises contacting the population of nucleic acid molecules with at least one site-specific endonuclease.

19. The method of claim 6, wherein linearization and/or fragmentation of said population of nucleic acid molecules is performed by contacting said population with at least one site-specific endonuclease.

20. The method of claim 9, wherein said single-stranded region of the target molecule of step c) is a 3' overhang.

* * * * *